US006867237B1

(12) United States Patent
Taylor et al.

(10) Patent No.: US 6,867,237 B1
(45) Date of Patent: Mar. 15, 2005

(54) DNA ENCODING APOPTOSIS-INDUCED EUCARYOTIC INITIATION FACTOR-5A AND DEOXYHYPUSINE SYNTHASE AND A METHOD FOR CONTROLLING APOPTOSIS IN ANIMALS AND HUMANS

(75) Inventors: Catherine Taylor, Waterloo (CA); Tzann-Wei Wang, Waterloo (CA); Larry Petrov, Kitchener (CA); John C. Carlson, Waterloo (CA); Richard Narayansingh, Kitchner (CA); John E. Thompson, Waterloo (CA)

(73) Assignee: Senesco Technologies, Inc., New Brunswick, NJ (US)

( * ) Notice: Subject to any disclaimer, the term of this patent is extended or adjusted under 35 U.S.C. 154(b) by 0 days.

(21) Appl. No.: 09/909,796

(22) Filed: Jul. 23, 2001

(51) Int. Cl.$^7$ .......................... A61K 31/32; A61K 31/13

(52) U.S. Cl. ...................... 514/674; 514/646; 435/180

(58) Field of Search ...................... 514/2, 44; 530/300, 530/329; 435/375, 325, 366, 6; 536/23.1, 24.5

(56) References Cited

U.S. PATENT DOCUMENTS

| | | | |
|---|---|---|---|
| 5,328,999 | A | 7/1994 | Bennett et al. |
| 5,849,587 | A | 12/1998 | Hanauske-Abel et al. |
| 6,020,139 | A | 2/2000 | Schwartz et al. |
| 6,124,091 | A | 9/2000 | Petryshyn |
| 6,214,572 | B1 | 4/2001 | Yuan et al. |
| 6,258,845 | B1 * | 7/2001 | Gerner et al. |

OTHER PUBLICATIONS

Schipper et al. Cancer Biology, vol. 0, 2000, pp. 55–68.*
Monti et al. Life Sciences, vol. 62, No. 9, 1998, pp. 799–806.*
Monti et al. Biochemical and Biophysical Research Communications, vol. 257, 1999, pp. 460–465.*
Lopez et al. Biocell, vol. 23, No. 3, 1999, pp. 223–228.*
Sakagami et al., Anticancer Research, vol. 20, 2000, pp. 265–270.*
Ha et al. Biochemical and Biophysical Research Communications, vol. 244, 1998, pp. 298–303.*
Ratasirayakorn et al., J. Periodontol, vol. 70, No. 2, Feb. 1999, pp. 179–184.*
Camon et al., Neuro Toxicology, vol. 15, No. 3, 1994, pp. 759–764.*
Tome et al., Biochem. J., vol. 328, 1997, pp. 847–854.*
Tome et al., Biol Signals, vol. 6, 1997, pp. 150–156.*
Pfeffer et al. (J. Biol. Chem. v276(49)45909–45913.*
Hannun, "Apoptosis and the Dilemma of Cancer Chemotherapy," Blood, vol. 89 (1997), pp. 1845–1853.
Bevec, Dorian et al., "Eukaryotic Initiation Factor 5A Activity and HIV–1 Rev Function," Biological Signals vol. 6:124–133 (1997).

Chen, Kuang Yu et al., "Biochemistry and Function of Hypusine Formation on Eukaryotic Initiation Factor 5A," Biological Signals vol. 6:105–109 (1997).
Gallie, Danierl R., "A tale of two termini: A functional interaction between the termini of an mRNA is a prerequisite for efficient translation initiation," Gene vol. 216:1–11 (1998).
Goyns, M. H., "The Role of Polyamines in Animal Cell Physiology," J. theor. Biol. vol. 97:577–589 (1982).
Igarashi, Kazuei et al., "Increase of Fidelity of Polypeptide Synthesis by Spermidine in Eukaryotic Cell–Free Systems," Eur. J. Biochem vol. 128:597–604 (1982).
Klein, T. M. et al., "Factors Influencing Gene Delivery into Zea Mays Cells by High–Velocity Microprojectiles," Bio/Technology vol. 6:559–563 (1988).
Murphey, Roberta J. et al., "Hypusine Formation in Protein by a Two–step Process in Cell Lysates," The Journal of Biological Chemistry vol. 262, No. 31:15033–15036 (1987).
Murphey, Robert J. et al., "Hypusine Biosynthesis in Protein and its Biological Consequences".
Park, Myung Hee et al., "The Biosynthesis of Hypusine (N$^e$–(4–Amino–2–hydroxybutyl)lysines); Alighment of the Butylamine Segment and Source of the Secondary Amino Nitrogen," The Journal of Biological Chemistry vol. 259, No. 19:12123–12127 (1984).
Park, M. H. et al., "Is hypusine essential for eukaryotic cell proliferation?" TIBS vol. 18:475–479 (1993).
Park, Myung Hee et al., "Cell–free Synthesis of Deoxyhypusine; Separation of Protein Substrate and Enzyme and Identification of 1, 3–Diaminopropane as a Product of Spermidine Cleavage," The Journal of Biological Chemistry vol. 263, No. 30:15264–15269 (1988).
Park, Myung Hee et al., "Comparison of the Activities of Variant Forms of eIF–4D," The Journal of Biological Chemistry, vol. 266, No. 13:7988–7994 (1991).
Park, Myung Hee et al., "The Biosynthesis of Protein–bound Hypusine (N$^e$–(4–Amino–2–hydroxybutyl)Lysine); Lysine as the Amino Precursor and the Intermediate Role of Deoxyhypusine (H$_e$–(4–amino–z–hydroxybutyl)Lysine), " The Journal of Biological Chemistry; vol. 257; No. 142:7217–7222 (1982).

(List continued on next page.)

Primary Examiner—John L. LeGuyader
Assistant Examiner—J D Schultz
(74) Attorney, Agent, or Firm—Kenyon & Kenyon

(57) ABSTRACT

Genes encoding an apoptosis-induced eukaryotic initiation Factor-5A (eIF-5A) and an apoptosis-induced deoxyhypusine synthase (DHS), whose expressions are induced by the onset of apoptosis, are identified. The DHS gene and the eIF-5A gene, alone or in combination, as well as inhibitors of the DHS reaction, are used to modulate apoptosis in animals and humans. For example, modulation of apoptosis in cells of animals and humans is achieved by introduction of a gene or gene fragment encoding apoptosis-induced eIF-5A, apoptosis-induced DHS, or both into the animal or human cell in antisense orientation.

4 Claims, 21 Drawing Sheets

OTHER PUBLICATIONS

Park, Myung Hee et al., "Identification of hypusine, an unusual amino acid, in a protein from human lymphocytes and of spermidine as its biosynthetic precursor," Proc. Natl. Acad. Sci. USA vol. 78, No. 5:2869–2873 (1981).

Pena, A. de la et al., "Transgenic rye plants obtained by injecting DNA into young floral tillers, " Nature vol. 325:274–276 (1987).

Rhoads, Robert E., "Regulation of Eukaryotic Protein Synthesis by Initiation Factors," The Journal of Biological Chemistry vol. 268, No. 5.3017–3020 (1993).

Tome, Margaret E. et al., "Cellular Eukaryotic Initiation Factor 5A Content as a Mediator of Polyamine Effects on Growth and Apoptosis," Biological Signals vol. 6:150–156 (1997).

Wolff, Edith C. et al., "Cleavage of Spermidine as the First Step in Deoxyhypusine Sythesis,, the Role of Nad[+]," The Journal of Biological Chemistry vol. 265, No. 9:4793–4799 (1990).

Zuk, Dorit et al., "A single amino acid substitution in yeast eIF–5A results in mRNA stabilization," The EMBO Journal vol. 17, No. 10:2914–2925 (1998).

Bevec, D. et al., "Molecular characterization of cDNA encoding functional human deoxhypusine synthase and chromosomal mapping of the corresponding gene locus," FEB Lett. vol. 378:195–198 (1996).

Brach, Marion A., "The Mitogenic Response to Tumor Necrosis Factor Alpha Requires c–Jun/AP–1," Molecular and Cellular Biology vol. 13, No. 7 4284–4290 (1993).

Cohen, Seymour S., "Growth of studies on Hypusine in Biological Systems," Biol Signals vol. 6:110–114 (1997).

Corpet, Florence, "Multiple sequence alignment of hierarchial clustering," Nucleic Acids Research vol. 16, No. 22:10880–10890 (1988).

Joe, Young Ae et al., "Cloning and Expression of Human Deoxyhypusine Synthase cDNA: Structure–Function Studies with the Recombinant Enzyme and Mutant Proteins," The Journal of Biological Chemistry vol. 270, No. 38:22386–22392 (1995).

Morton, R. et al., "Gene replacement," Molecular Breeding vol. 1:123–132 (1995).

Nierlich, Donald P. et al., "Molecular Mechanisms in the Control of Gene Expression," ICN–UCLA Sumposia on Molecular and Cellular Biology vol. 5 (1976).

Park, Myung Hee et al., "Hypusine Is Essential for Eukaryotic Cell Proliferation," Biological Signals vol. 6:115–123 (1997).

Park, Myung Hee et al., "Deoxyhypusine Synthase activity Is Essential for Cell Viability in the Yeast Saccharomyces cerevisiae," The Journal of Biological Chemistry vol. 273, No. 3:1677–1683 (1998).

Park, Myung Hee et al., "Hypusine: its post–translation formation in eukaryotic initiation factor 5A and its potential role in cellular regulation," BioFactors vol. 4, No. 2:95–104 (1993).

Ranu, Rajinder Singh et al., "Regulation of Protein Synthesis in Rabbit Reticulocyte Lysates: Preparation of Efficient Protein Synthesis Lysates and the Purification and Characterization of the Heme–Regulated Translational Inhibitory Protein Kinase[1]," Methods in Enzymology, vol. LX:459–484 (1979).

Reich, T. J. et al., "Efficient Transformation of Alfalfa Protoplasts by the Intranuclear Microinijection of Ti Plasmids," Bio/Technology vol. 4:1001–1004 (1986).

Tome, Margaret E. et al., "Excess putrescine accumulation inhibits theformation of modified eukaryotic initiation factor 5A (eIf–5A) and induces apoptosis," Biochem J. vol. 328:847–854 (1997).

Wolff, Edith C. et al., "Enzyme–Substrate Intermediate Formation at Lysine 329 of Human Deoxyhypusine Synthase," The Journal of Biological Chemistry vol. 272, No. 25:15865–15871 (1997).

Yan, Yong Ping et al., "Molecular cloning and functional expression of human deoxuhypusine synthasa cDNA based on expressed sequence tag information," Biochem. J. vol. 315 429–434 (1996).

Bold, Richard J. et al., "Apoptosis, cancer and cancer therapy," Surgical Oncology, vol. 6, No.3:pp. 133–142 (1997).

Caraglia, M. et al., "The role of eukaryotic initiation factor 5A in the control of cell proliferation and apoptosis," Amino Acids, vol. 20: pp. 91–104 (2001).

Chang, Howard Y., "Proteases for Cell Suicide. Functions and Regulation of Caspases," Microbiology and Molecular Biology Review, vol. 64, No. 4, pp. 821–846 (2000).

Chen, Zong Ping et al., "Effects of inhibitors of deoxyhypusine synthase on the differentiation of mouse neuroblastoma and erythroleukemia cells," Cancer Letters, vol. 105, pp. 233–239 (1996).

Creagh, E.M. et al., "Caspases: Cellular demolition experts," Biochemical Society Transactions, vol. 29, part 6, (2000).

Evan, Gerard et al., "Apoptosis and the cell cycle," Current Opinion Cell Biology, vol. 7, pp. 825–834 (1995).

Hickman, J.A., "Apoptosis Chemotherapy Resistance," European Journal of Cancer, vol. 32A, No. 6, pp. 921–926 (1996).

Lowe, Scott W. et al, "Apoptosis in Cancer", Carcinogenesis, vol. 21, No. 3, 485–495, (Mar. 2000).

Lu, Jiebo et al., "Aminohexanoic hydroxamate is a potent inducer of the differentiation of mouse neuroblastoma cells," Cancer Letters, vol. 160, pp. 59–66 (2000).

Müllauer, Leonhard et al, "Mutations in apoptosis genes: a pathogenetic factor for human disease," Mutation Research, vol. 488, pp. 211–231 (2000).

O'Connor, Liam et al., "Apoptosis and cell division" Current in Cell Biology, vol. 12., pp. 257–263 (2000).

Park, Myung Hee et al., "The polyamine–derived amino acid hypusine: its post–translational formation in eIF–5A and its role in cell proliferation," Amino Acids, vol. 10, pp. 109–121 (1996).

Reed, John C. et al., "Drug discovery opportunities from apoptosis research," Current Opinion in Biotechnology, vol. 11, pp. 586–592 (2000).

Reed, John C., "Bcl–2 family proteins regulators of chemoresistance in cancer," Toxicology Letters, vols. 82/83, pp. 155–158 (1995).

Ryan Kevin M. et al., "Regulation and function of the p23 tumor suppressor protein," Current Opinion in Cell Biology, vol. 13, 332–337 (2001).

Salomons, Gaija S. et al., "The Baxα: Bcl–2 Tario Modulates the Response to Dexamethasone in Leukaemic Cells and is Highly Variable in Childhood Acute Leukaemia", Interanational Journal Cancer, vol. 71, pp. 959–965 (1997).

Schmitt, Clemens A. et al., "Apoptosis and Therapy," Journal of Pathology, vol. 187, pp. 127–137 (1999).

Schuler, M., "Mechanisms of p53–dependent apopotosis," Biochemical Society Transactions, vol. 29, part 6 (2001).

Shi, Xiao–Ping et al., "Effects on $N^1$–guanyl–1,7–diaminoheptane, an inhibitor of deoxyhypusine synthase, on the growth of tumorigenic cell lines in culture," *Biochemic et Biophisica Acta*, vol. 1310, pp. 119–126 (1996).

Wall, Nathan R. et al., "Bax:Bcl–2 ration modulation by bryostatin 1 and novel antitubulin agents is important for susceptibility to drug induced apoptosis in the human early pre–B acute lymphoblastic leukemia cell line, Reh," *Leukemia Research*, vol. 23, pp. 881–888 (1999).

Wallace–Brodeur, R.R. et al., "Clinical Implications of p53 mutations," *CMLS Cellular and Molecular Life Sciences*, vol. 54, pp. 64–75 (1999).

Zörnig, Martin et al., "Apoptosis regulators and their role in tumorigenesis," *Biochica et Biophysica Acta*, vol. 1551, pp. F1–F37 (2001).

* cited by examiner

```
TCGAAGACCGGTAAGCACGGCCATGCCAAGGTCCATCTGGTTGGTATTGATATTTTTACTGGGAAGAAATAT
 S  K  T  G  K  H  G  H  A  K  V  H  L  V  G  I  D  I  F  T  G  K  K  Y
GAAGATATCTGCCCGTCGACTCATAACATGGATGTCCCCAACATCAAAAGGAATGATTTCCAGCTGATTGGC
 E  D  I  C  P  S  T  H  N  M  D  V  P  N  I  K  R  N  D  F  Q  L  I  G
ATCCAGGATGGGTACCTATCCCTGCTCCAGGACAGTGGGGAGGTACGAGAGGACCTTCGTCTGCCTGAGGGA
 I  Q  D  G  Y  L  S  L  L  Q  D  S  G  E  V  R  E  D  L  R  L  P  E  G
GACCTTGGCAAGGAGATTGAGCAGAAGTATGACTGTGGAGAAGAGATCCTGATCACAGTGCTGTCCGCCATG
 D  L  G  K  E  I  E  Q  K  Y  D  C  G  E  E  I  L  I  T  V  L  S  A  M
ACAGAGGAGGCAGCTGTTGCAATCAAGGCCATGGCAAAATAACTGGCTTCCAGGGTGGCGGTGGTGGCAGCA
 T  E  E  A  A  V  A  I  K  A  M  A  K
GTGATCCATGAGCCTACAGAGGCCCCTCCCCCAGCTCTGGCTGGGCCCTTGGCTGGACTCCTATCCAATTTA
TTTGACGTTTTATTTTGGTTTTCCTCACCCCTTCAAACTGTCGGGGAGACCCTGCCCTTCACCTAGCTCCCT
TGGCCAGGCATGAGGGAGCCATGGCCTTGGTGAAGCTACCTGCCTCTTCTCTCGCAGCCCTGATGGGGGAAA
GGGAGTGGGTACTGCCTGTGGTTTAGGTTCCCCTCTCCCTTTTTCTTTTTAATTCAATTTGGAATCAGAAAG
CTGTGGATTCTGGCAAATGGTCTTGTGTCCTTTATCCCACTCAAACCCATCTGGTCCCCTGTTCTCCATAGT
CCTTCACCCCCAAGCACCACTGACAGACTGGGGACCAGCCCCCTTCCCTGCCTGTGTCTCTTCCCAAACCCC
TCTATAGGGGTGACAAGAAGAGGAGGGGGGGAGGGGACACGATCCCTCCTCAGGCATCTGGGAAGGCCTTGC
CCCCATGGGCTTTACCCTTTCCTGTGGGCTTTCTCCCTGACACATTTGTTAAAAATCAAACCTGAATAAAAC
TACAAGTTTAATATGAAAAAAAAAAAAAAAAAAAAA
(972 NT, 109 aa)
```

FIG.3

```
CAGGTCTAGAGTTGGAATCGAAGCCTCTTAAAATGGCAGATGATTTGGACTTCGAGACAGGAGATGCAGGGG
                                    M  A  D  D  L  D  F  E  T  G  D  A  G
CCTCAGCCACCTTCCCAATGCAGTGCTCAGCATTACGTAAGAATGGTTTTGTGGTGCTCAAGGGCCGGCCAT
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I
ATATTTTTACTGGGAAGAAATATGAAGATATCTGCCCGTCGACTCATAACATGGATGTCCCCAACATCAAAA
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R
AGGACCTTCGTCTGCCTGAGGGAGACCTTGGCAAGGAGATTGAGCAGAAGTATGACTGTGGAGAAGAGATCC
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCTCGAG
 L  I  T  V  L  S  A  M  T  E  E  A  A  V  A  I  K  A
```

```
CAGGTCTAGAGTTGGAATCGAAGCCTCTTAAAATGGCAGATGATTTGGACTTCGAGACAGGAGATGCAGGGG
                              M  A  D  D  L  D  F  E  T  G  D  A  G       13
CCTCAGCCACCTTCCCAATGCAGTGCTCAGCATTACGTAAGAATGGTTTTGTGGTGCTCAAGGGCCGGCCAT  144
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I   61
ATATTTTTACTGGGAAGAAATATGAAGATATCTGCCCGTCGACTCATAACATGGATGTCCCCAACATCAAAA  288
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R  109
AGGACCTTCGTCTGCCTGAGGGAGACCTTGGCAAGGAGATTGAGCAGAAGTATGACTGTGGAGAAGAGATCC  432
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCCATGGCAAAATAACTGGCTT
 L  I  T  V  L  S  A  M  T  E  E  A  A  V  A  I  K  A  M  A  K  *        154
CCAGGGTGGCGGTGGTGGCAGCAGTGATCCATGAGCCTACAGAGGCCCCTCCCCCAGCTCTGGCTGGGCCCT  576
TGGCTGGACTCCTATCCAATTTATTTGACGTTTTATTTTGGTTTTCCTCACCCCTTCAAACTGTCGGGGAGA
CCCTGCCCTTCACCTAGCTCCCTTGGCCAGGCATGAGGGAGCCATGGCCTTGGTGAAGCTACCTGCCTCTTC  720
TCTCGCAGCCCTGATGGGGGAAAGGGAGTGGGTACTGCCTGTGGTTTAGGTTCCCCTCTCCCTTTTTCTTTT
TAATTCAATTTGGAATCAGAAAGCTGTGGATTCTGGCAAATGGTCTTGTGTCCTTTATCCCACTCAAACCCA  864
TCTGGTCCCCTGTTCTCCATAGTCCTTCACCCCCAAGCACCACTGACAGACTGGGGACCAGCCCCCTTCCCT
GCCTGTGTCTCTTCCCAAACCCCTCTATAGGGGTGACAAGAAGAGGAGGGGGGAGGGGACACGATCCCTCC  1008
TCAGGCATCTGGGAAGGCCTTGCCCCCATGGGCTTTACCCTTTCCTGTGGGCTTTCTCCCTGACACATTTGT
TAAAAATCAAACCTGAATAAAACTACAAGTTTAATATGAAAAAAAAAAAAAAAAAAAAAA              1139
```

(1139 NT. 154 aa)

FIG. 5 rat vs. human(BC000751 or NM_001970) 96.5% identity (coding)

```
             10        20        30        40        50        60
rat   ATGGCAGATGATTTGGACTTCGAGACAGGAGATGCAGGGGCCTCAGCCACCTTCCCAATG
      ::::::::::: ::::::::::::::::::::::::::::::::::::::::::::::::
human ATGGCAGATGACTTGGACTTCGAGACAGGAGATGCAGGGGCCTCAGCCACCTTCCCAATG
             10        20        30        40        50        60

70        80        90       100       110       120
rat   CAGTGCTCAGCATTACGTAAGAATGGTTTTGTGGTGCTCAAGGGCCGGCCATGTAAGATC
      :::::::::::::::::::::::::::::: :::::::::::: ::::::::::::::::
human CAGTGCTCAGCATTACGTAAGAATGGCTTTGTGGTGCTCAAAGGCCGGCCATGTAAGATC
             70        80        90       100       110       120

130       140       150       160       170       180
rat   GTCGAGATGTCTACTTCGAAGACTGGCAAGCATGGCCATGCCAAGGTCCATCTGGTTGGT
      :::::::::::::::::::::::::::::::: ::::: :::::::::::::::::::::
human GTCGAGATGTCTACTTCGAAGACTGGCAAGCACGGCCACGCCAAGGTCCATCTGGTTGGT
            130       140       150       160       170       180

190       200       210       220       230       240
rat   ATTGATATTTTTACTGGGAAGAAATATGAAGATATCTGCCCGTCGACTCATAACATGGAT
      ::::: ::  :::::::::::::::::::::::::::::::::: ::::::::  :::::
human ATTGACATCTTTACTGGGAAGAAATATGAAGATATCTGCCCGTCAACTCATAATATGGAT
            190       200       210       220       230       240

250       260       270       280       290       300
rat   GTCCCCAACATCAAAAGGAATGATTTCCAGCTGATTGGCATCCAGGATGGGTACCTATCC
      ::::::::::::::::::::::::: :::::::::::::::::::::::::::::::::
human GTCCCCAACATCAAAAGGAATGACTTCCAGCTGATTGGCATCCAGGATGGGTACCTATCA
            250       260       270       280       290       300

310       320       330       340       350       360
rat   CTGCTCCAGGACAGTGGGGAGGTACGAGAGGACCTTCGTCTGCCTGAGGGAGACCTTGGC
      ::::::::::::::: :::::::::::::::::::::::::: :::::::::::::::::
human CTGCTCCAGGACAGCGGGGAGGTACGAGAGGACCTTCGTCTCCCTGAGGGAGACCTTGGC
            310       320       330       340       350       360

370       380       390       400       410       420
rat   AAGGAGATTGAGCAGAAGTATGACTGTGGAGAAGAGATCCTGATCACAGTGCTGTCCGCC
      :::::::::::::::::::: ::::::::::::::::::::::::::::: ::::: :::
human AAGGAGATTGAGCAGAAGTACGACTGTGGAGAAGAGATCCTGATCACGGTGCTGTCTGCC
            370       380       390       400       410       420

430       440       450       460
rat   ATGACAGAGGAGGCAGCTGTTGCAATCAAGGCCATGGCAAAA
      :::::::::::::::::::::::::::::::::::::::::
human ATGACAGAGGAGGCAGCTGTTGCAATCAAGGCCATGGCAAAA
            430       440       450       460
```

FIG.6 rat vs. human(NM_020390) 72.5% identity (coding)

```
                 10        20        30        40        50        60
rat     ATGGCAGATGATTTGGACTTCGAGACAGGAGATGCAGGGGCCTCAGCCACCTTCCCAATG
        :::::::::  ::  :  ::  :::     ::  ::::::  ::::: ::      :::  :  :::  :::
human   ATGGCAGACGAAATTGATTTCACTACTGGAGATGCCGGGGCTTCCAGCACTTACCCTATG
                 10        20        30        40        50        60

70        80        90       100       110       120
rat     CAGTGCTCAGCATTACGTAAGAATGGTTTTTGTGGTGCTCAAGGGCCGGCCATGTAAGATC
        ::::::::::  ::  ::  ::  ::  ::  ::  ::::::::::::  ::  ::::::  ::
human   CAGTGCTCGGCCTTGCGCAAAAACGGCTTCGTGGTGCTCAAAGGACGACCATGCAAAATA
                 70        80        90       100       110       120

130       140       150       160       170       180
rat     GTCGAGATGTCTACTTCGAAGACTGGCAAGCATGGCCATGCCAAGGTCCATCTGGTTGGT
        ::  :::::::::  ::::::  ::  :::::  :::::::::::::::::::::  ::  :::  :::::
human   GTGGAGATGTCAACTTCCAAAACTGGAAAGCATGGTCATGCCAAGGTTCACCTTGTTGGA
                130       140       150       160       170       180

190       200       210       220       230       240
rat     ATTGATATTTTTACTGGGAAGAAATATGAAGATATCTGCCCGTCGACTCATAACATGGAT
        ::::::::::::  ::  ::  :::::::::::::::  ::  ::  ::::::  ::::::::::
human   ATTGATATTTTTCACGGGCAAAAAATATGAAGATATTTGTCCTTCTACTCACAACATGGAT
                190       200       210       220       230       240

250       260       270       280       290       300
rat     GTCCCCAACATCAAAAGGAATGATTTCCAGCTGATTGGCATCCAGGATGGGTACCTATCC
        ::  ::  ::  ::  ::  ::  ::::::::  ::  :::::  ::  :::::  :::::  :::
human   GTTCCAAATATTAAGAGAAATGATTATCAACTGATATGCATTCAAGATGGTTACCTTTCC
                250       260       270       280       290       300

310       320       330       340       350       360
rat     CTGCTCCAGGACAGTGGGGAGGTACGAGAGGACCTTCGTCTGCCTGAGGGGAGACCTTGGC
        :::::       ::  :  :::  ::  ::  ::::::  :::      :::::  ::  ::  ::: :::
human   CTGCTGACAGAAACTGGTGAAGTTCGTGAGGATCTTAAACTGCCAGAAGGTGAACTAGGC
                310       320       330       340       350       360

370       380       390       400       410       420
rat     AAGGAGATTGAGCAGAAGTATGACTGTGGAGAAGAGATCCTGATCACAGTGCTGTCCGCC
        ::  ::  ::  :::      ::  ::   :    ::  :::::  :  :  :  :   :::  ::
human   AAAGAAATAGAGGGGAAAATACAATGCAGGTGAAGATGTACAGGTGTCTGTCATGTGTGCA
                370       380       390       400       410       420

430       440       450       460
rat     ATGACAGAGGAGGCAGCTGTTGCAATCAAGGCCATGGCAAAA
        ::::  ::  ::         ::::::  ::  ::  ::      ::::::
human   ATGAGTGAAGAATATGCTGTAGCCATAAAACCCT--GCAAAT
                430       440       450       460
```

FIG.7 rat vs. mouse (BC003889) 98.3% identity (coding)

```
              10        20        30        40        50        60
rat   ATGGCAGATGATTTGGACTTCGAGACAGGAGATGCAGGGGCCTCAGCCACCTTCCCAATG
      ::::::::::::::::::::::::::::::::::::::::::::::::::::::::::::
mouse ATGGCAGATGATTTGGACTTCGAGACAGGAGATGCAGGGGCCTCAGCCACCTTCCCAATG
              10        20        30        40        50        60

70        80        90       100       110       120
rat   CAGTGCTCAGCATTACGTAAGAATGGTTTTGTGGTGCTCAAGGGCCGGCCATGTAAGATC
      ::::::::::::::::::::::::::::::::::::::::: ::::::::::::::::::
mouse CAGTGCTCAGCATTACGTAAGAATGGTTTTGTGGTGCTCAAAGGCCGGCCATGTAAGATC
              70        80        90       100       110       120

130       140       150       160       170       180
rat   GTCGAGATGTCTACTTCGAAGACTGGCAAGCATGGCCATGCCAAGGTCCATCTGGTTGGT
      :::::::::::::::::::::::::::::::::::::::::::::::::::::::::::
mouse GTCGAGATGTCTACTTCGAAGACTGGCAAGCATGGCCATGCCAAGGTCCATCTGGTTGGC
             130       140       150       160       170       180

190       200       210       220       230       240
rat   ATTGATATTTTTACTGGGAAGAAATATGAAGATATCTGCCCGTCGACTCATAACATGGAT
      ::::: :::::::::::::::::::::::::::::::::::::::::::::::: ::::::
mouse ATTGACATTTTTACTGGGAAGAAATATGAAGATATCTGCCCGTCGACTCATAATATGGAT
             190       200       210       220       230       240

250       260       270       280       290       300
rat   GTCCCCAACATCAAAAGGAATGATTTCCAGCTGATTGGCATCCAGGATGGGTACCTATCC
      :::::::::::::::: ::::::: ::::::::::::::::::::::::::::::::::
mouse GTCCCCAACATCAAACGGAATGACTTCCAGCTGATTGGCATCCAGGATGGGTACCTATCC
             250       260       270       280       290       300

310       320       330       340       350       360
rat   CTGCTCCAGGACAGTGGGGAGGTACGAGAGGACCTTCGTCTGCCTGAGGGAGACCTTGGC
      ::::::::::::::::::::::::::::::::::::::::::::::::: ::::::::::
mouse CTGCTCCAGGACAGTGGGGAGGTACGAGAGGACCTTCGTCTGCCTGAAGGAGACCTTGGC
             310       320       330       340       350       360

370       380       390       400       410       420
rat   AAGGAGATTGAGCAGAAGTATGACTGTGGAGAAGAGATCCTGATCACAGTGCTGTCCGCC
      :::::::::::::::::::::::::::::::::::::::::::::::::::::::: :::
mouse AAGGAGATTGAGCAGAAGTATGACTGTGGAGAAGAGATCCTGATCACAGTGCTGTCTGCC
             370       380       390       400       410       420

430       440       450       460
rat   ATGACAGAGGAGGCAGCTGTTGCAATCAAGGCCATGGCAAAA
      :::::::::::::::::::::::::::::::::::::::::
mouse ATGACAGAGGAGGCAGCTGTTGCAATCAAGGCCATGGCAAAA
             430       440       450       460
```

FIG.8 rat vs. human(BC000751 or NM_001970) 100.0% identity

```
           10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
human  MADDLDFETGDAGASATFPMQCSALRKNGFVVLKGRPCKIVEMSTSKTGKHGHAKVHLVG
           10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
human  IDIFTGKKYEDICPSTHNMDVPNIKRNDFQLIGIQDGYLSLLQDSGEVREDLRLPEGDLG
           70        80        90       100       110       120

130       140       150
rat    KEIEQKYDCGEEILITVLSAMTEEAAVAIKAMAK
       :::::::::::::::::::::::::::::::::
human  KEIEQKYDCGEEILITVLSAMTEEAAVAIKAMAK
          130       140       150
```

FIG.9 rat vs. human(NM_020390) 82.5% identity

```
              10         20         30         40         50         60
rat    MADDLDFETGDAGASATFPMQCSALRKNGFVVLKGRPCKIVEMSTSKTGKHGHAKVHLVG
       :::...:: :::::::::.:.::::::::::::::::::::::::::::::::::::::
human  MADEIDFTTGDAGASSTYPMQCSALRKNGFVVLKGRPCKIVEMSTSKTGKHGHAKVHLVG
              10         20         30         40         50         60

70         80         90        100        110        120
rat    IDIFTGKKYEDICPSTHNMDVPNIKRNDFQLIGIQDGYLSLLQDSGEVREDLRLPEGDLG
       ::::::::::::::::::::::::::::: ::::::::::::: ..:::::::.:::::
human  IDIFTGKKYEDICPSTHNMDVPNIKRNDYQLICIQDGYLSLLTETGEVREDLKLPEGELG
              70         80         90        100        110        120

130        140        150
rat    KEIEQKYDCGEEILITVLSAMTEEAAVAIKAMAK
       ::::  ::.  ::...  ...:  ::.:: :::::   :
human  KEIEGKYNAGEDVQVSVMCAMSEEYAVAIKP-CK
              130        140        150
```

FIG. 10 rat vs. mouse (BC003889)100.0% identity

```
              10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
mouse  MADDLDFETGDAGASATFPMQCSALRKNGFVVLKGRPCKIVEMSTSKTGKHGHAKVHLVG
              10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
mouse  IDIFTGKKYEDICPSTHNMDVPNIKRNDFQLIGIQDGYLSLLQDSGEVREDLRLPEGDLG
              70        80        90       100       110       120

130       140       150
rat    KEIEQKYDCGEEILITVLSAMTEEAAVAIKAMAK
       :::::::::::::::::::::::::::::::::
mouse  KEIEQKYDCGEEILITVLSAMTEEAAVAIKAMAK
             130       140       150
```

FIG. 11

SOUTHERN BLOT OF RAT GENOMIC DNA
Rat eIF-5A 1139 bp
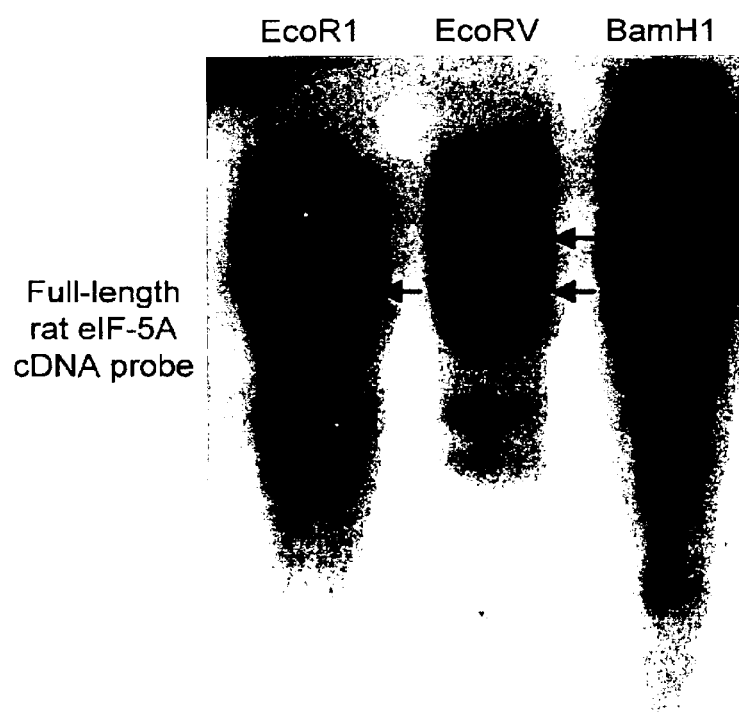
FIG.13

```
GCTGTGTATTATTGGGCCCATAAGAACCACATACCTGTGCTGAGTCCTGCACTCACAGACGGCTCACTGGGT
  A  V  Y  Y  W  A  H  K  N  H  I  P  V  L  S  P  A  L  T  D  G  S  L  G
GACATGATCTTTTTCCATTCCTATAAAAACCCAGGCTTGGTCCTGGACATCGTTGAAGACCTGCGGCTCATC
  D  M  I  F  F  H  S  Y  K  N  P  G  L  V  L  D  I  V  E  D  L  R  L  I
AACATGCAGGCCATTTTTCGCCAAGCGCACTGGGATGATCATCCTGGGTGGAGGCGTGGTCAAGCACCACATC
  N  M  Q  A  I  F  A  K  R  T  G  M  I  I  L  G  G  G  V  V  K  H  H  I
GCCAATGCTAACCTCATGCGGAATGGAGCTGACTACGCTGTTTATATCAACACAGCCCAGGAGTTTGATGGC
  A  N  A  N  L  M  R  N  G  A  D  Y  A  V  Y  I  N  T  A  Q  E  F  D  G
TCAGACTCAGGAGCCCGGCCAGATGAGGCTGTCTCCTGGGGCAAGATCCGGATGGATGCACAGCCAGTAAAG
  S  D  S  G  A  R  P  D  E  A  V  S  W  G  K  I  R  M  D  A  Q  P  V  K
GTCTATGCTGATGCATCTCTGGTTTTCCCCTTGCTGGTGGCTGAGACATTCGCCCAAAAGGCAGATGCCTTC
  V  Y  A  D  A  S  L  V  F  P  L  L  V  A  E  T  F  A  Q  K  A  D  A  F
AGAGCTGAGAAGAATGAGGACTGAGCAGATGGGTAAAGACGGAGGCTTCTGCCACACCTTTATTTATTATTT
  R  A  E  K  N  E  D
GCATACCAACCCCTCCTGGGCCCTCTCCTTGGTCAGCAGCATCTTGAGAATAAATGGCCTTTTTGTTGGTTT
CTGTAAAAAAAGGACTTTAAAAAAAAAAAAA
```

(606 NT, 151 aa)

FIG.15 rat vs. human (BC000333) 87.4% identity (coding)

```
            10         20         30         40         50         60
rat     GCTGTGTATTATTGGGCCCATAAGAACCACATACCTGTGCTGAGTCCTGCACTCACAGAC
        :  ::::::::  :::::::: ::::::::::::: ::::::  :  ::::: ::::: :::::::
human   TCCGTGTATTACTGGGCCCAGAAGAACCACATCCCTGTGTTTAGTCCCGCACTTACAGAC
            10         20         30         40         50         60

70         80         90        100        110        120
rat     GGCTCACTGGGTGACATGATCTTTTTTCCATTCCTATAAAAACCCAGGCTTGGTCCTGGAC
        ::::: ::::: :::::::::::::: :::::::::::  ::::: :::  ::::::::::::
human   GGCTCGCTGGGCGACATGATCTTCTTCCATTCCTACAAGAACCCGGGCCTGGTCCTGGAC
            70         80         90        100        110        120

130        140        150        160        170        180
rat     ATCGTTGAAGACCTGCGGCTCATCAACATGCAGGCCATTTTTCGCCAAGCGCACTGGGATG
        :::::::::  ::::::: :::::::::::: :::::::::: ::  ::::::: :::::::::::
human   ATCGTTGAGGACCTGAGGCTCATCAACACACAGGCCATCTTTGCCAAGTGCACTGGGATG
           130        140        150        160        170        180

190        200        210        220        230        240
rat     ATCATCCTGGGTGGAGGCGTGGTCAAGCACCACATCGCCAATGCTAACCTCATGCGGAAT
        :::::  :::::::  :::::::::::::::::::::::::: :::::::: :::::::::::::::
human   ATCATTCTGGGCGGGGGCGTGGTCAAGCACCACATTGCCAATGCCAACCTCATGCGGAAC
           190        200        210        220        230        240

250        260        270        280        290        300
rat     GGAGCTGACTACGCTGTTTATATCAACACAGCCCAGGAGTTTGATGGCTCAGACTCAGGA
        ::  :: ::::::::::::::::: :::::::::::::::::::::::::::::::  ::::::::
human   GGGGCCGACTACGCTGTTTACATCAACACAGCCCAGGAGTTTGATGGCTCTGACTCAGGT
           250        260        270        280        290        300

310        320        330        340        350        360
rat     GCCCGGCCAGATGAGGCTGTCTCCTGGGGCAAGATCCGGATGGATGCACAGCCAGTAAAG
        :::::  :::::: :::::::::::::::::::::::::::::: :::::::::::::  :  :::
human   GCCCGACCAGACGAGGCTGTCTCCTGGGGCAAGATCCGGGTGGATGCACAGCCCGTCAAG
           310        320        330        340        350        360

370        380        390        400        410        420
rat     GTCTATGCTGATGCATCTCTGGTTTTCCCCTTGCTGGTGGCTGAGACATTCGCCCAAAAG
        ::::::::::::::  ::  :::::  ::::::: ::::  ::::::::::: ::  ::  :::  :::
human   GTCTATGCTGACGCCTCCCTGGTCTTCCCCCTGCTTGTGGCTGAAACCTTTGCCCAGAAG
           370        380        390        400        410        420

430        440        450
rat     GCAGATGCCTTCAGAGCTGAGAAGAATGAGGAC
        :::::::::::    ::::::::::::  ::::::
human   ATGGATGCCTTCATGCATGAGAAGAACGAGGAC
           430        440        450
```

FIG.18

DNA ENCODING APOPTOSIS-INDUCED EUCARYOTIC INITIATION FACTOR-5A AND DEOXYHYPUSINE SYNTHASE AND A METHOD FOR CONTROLLING APOPTOSIS IN ANIMALS AND HUMANS

FIELD OF THE INVENTION

The present invention relates to polynucleotides which encode animal polypeptides that exhibit apoptosis-induced expression. The invention also relates to methods for modulating apoptosis in animals and humans. More particularly, the present invention relates to an apoptosis-induced eukaryotic initiation Factor-5A (eIF-5A) and an apoptosis-induced deoxyhypusine synthase (DHS) whose expressions are induced by the onset of apoptosis, and the use of the DHS gene and the eIF-5A gene, alone or in combination, as well as inhibitors of the DHS reaction, to modulate apoptosis in animals and humans.

BACKGROUND OF THE INVENTION

Apoptosis is the highly regulated process of programmed cell death that is essential for normal tissue development and homeostasis. It occurs in animals, humans and plants. In humans, for example, de-regulation of apoptotic processes contributes to a wide range of diseases, including disorders caused by loss of cells (e.g., neurodegenerative diseases, tissue damage from stroke or heart failure, and AIDS). Reed, J. C. and Tomaselli, K. J. (2000) *Curr. Opin. Biotech.*, 11, 586–592. In plants, the formation of water-conducting xylem vessels, a developmental process termed xylogenesis, entails programmed cell death that appears to be a plant counterpart of animal apoptosis. Specifically, apoptosis during xylogenesis features fragmentation of nuclear DNA, recruitment of cysteine proteases and the formation of apoptotic bodies, which are distinctive and characteristic features of animal apoptosis. Roberts, K. and McCann, M. C. (2000) *Current Opinion in Plant Biology*, 3, 517–522; Mittler R. and Lam E. (1995) *Plant Physiol*, 108, 489–493; Ye. Z.-H and Varner, J. E. (1996) *Plant Mol Biol.*, 30, 1233–1246; Minami, A. and Fukuda, H. (1995) *Plant Cell Physiol*, 36, 1599–1606; Beers, E. P. and Freeman, T. B. (1997) *Plant Physiol.*, 113, 873–880; Iliev, I and Savidge R. (11999) *Phytochemistry*, 50, 953–960; Yu, F.-X. and Chye, M.-L. (1999) *Plant J.*, 17, 321–327; Groover, A. and Jones, A. M. (1999) *Plant Physiol.*, 119, 375–384; Groover, A., DeWitt, N. G., Heidel, A. and Jones, A. M. (1997) *Protoplasma* 196, 197–211. Inhibitors and elicitors of apoptosis have been cloned from a variety of species, but much of the apoptotic signaling pathway remains to be elucidated.

Cells undergoing apoptosis identified by morphological changes which include cell shrinkage, condensation of chromatin, nuclear fragmentation, and the formation of apoptotic bodies (Reed and Tomaselli, 2000). One of the hallmarks of apoptotic cell death is the appearance of DNA fragmentation in multiples of 200 base pairs, which results from the activation of an endonuclease that cleaves the DNA between nucleosomes. Caspases, a family of proteases, are the main executors of the apoptotic program. Two major pathways to caspase induction include activation by molecules released from mitochondria, such as cytochrome c, and activation of death receptors by extracellular signals. Newmeyer, D. D., Farschon, D. M. and Reed, J. C. (1994) *Cell*, 79, 353–364; O'Connor, I. Huang, D.C., O'Reilly, L. A. and Strasser, A. (2000) *Curr. Opin. Cell Biol.*, 24, 49–52.

The unique amino acid, hypusine, is found in all examined eukaryotes and archaebacteria, but not in eubacteria, and eukaryotic initiation factor 5A (eIF-5A) is the only known hypusine-containing protein. Park, M. H. (1988) *J. Biol. Chem.*, 263, 7447–7449; Schumann. H. and Klink, F. (1989) *System Appl. Microbiol.*, 11, 103–107; Bartig, D., Scümann, H., and Klink, F. (1990) *System. Appl. Microbiol.*, 13, 112–116; Gordon, E. D., Mora, R., Meredith, S.C., Lee, C. and Lindquist, S. L. (1987a) *J. Biol. Chem.* 262, 16585–16589. Active eIF-5A is formed in two post-translational steps: the first step is the formation of a deoxyhypusine residue by the transfer of the 4-aminobutyl moiety of spermidine to the c-amino group of a specific lysine of the precursor eIF-5A catalyzed by deoxyhypusine synthase; the second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIF-5A which suggests that this modification may be important for survival. Park, M. H., Wolff, E. C., and J. E. Folk (1993) *Biofactors*, 4, 95–104. This assumption is further supported by the observation that inactivation of both of the eIF-5A's found to date in yeast, or inactivation of the deoxyhypusine synthase gene which catalyzes the first step in their activation, blocks cell division. Schnier, J. Schwelberger, H., Smit-McBride, Z., Kang, H. A., and Hershey, J. W. B. (1991) *Mol. Cell. Biol.*, 11, 3105–3114; Sasaki, K, Abid, M. R. and Miyazaki, M. (1996) FEBS Lett., 384, 151–154; Park, M. H., Joe, Y. A. and Kang, K. R. (1998) *J. Biol. Chem.*, 273, 1677–1683. However, depletion of eIF-5A protein in yeast resulted in only a small decrease in total protein synthesis suggesting that eIF-5A may be required for the translation of specific subsets of mRNA's rather than for protein global synthesis. Kang, H. A., Schwelberger, H. G., and Hershey, J. W. B. (1993) Effect of initiation factor eIF-5A depletion on cell proliferation and protein synthesis, in Tuite, M. (ed.), *Protein Synthesis and Targeting in Yeast*, NATO Series H. This view is supported by the recent finding that ligands which bind eIF-5A share highly conserved motifs. Xu, A. and Chen, K. Y. (2001) *J. Biol. Chem.*, 276, 2555–2561. The hypusine residue of modified eIF-5A was found to be essential for sequence-specific binding to RNA, and binding did not provide protection from ribonucleases. In addition, intracellular depletion of eIF-5A resulted in a significant accumulation of specific mRNAs in the nucleus, indicating that eIF-5A may be responsible for shuttling specific classes of mRNAs from the nucleus to the cytoplasm. Liu, Y. and Tartakoff, A. (1997) *Supplement to Molecular Biology of the Cell*, 8, 426a. Abstract no. 2476, 37th American Society for Cell Biology Annual Meeting. The accumulation of eIF-5A at nuclear pore-associated intranuclear filaments and its interaction with a general nuclear export receptor further suggest that eIF-5A is a nucleocytoplasmic shuttle protein rather than a component of polysomes. Rosorius, O., Reichart, B., Kratzer, F., Heger, P., Dabauvalle, M.-C. and Hauber, J. (1999) *J. Cell Science*, 112, 2369–2380.

The first cDNA for eIF-5A was cloned from human in 1989 by Smit-McBride et al., and since then cDNA's or genes for eIF-5A have been cloned from various eukaryotes including yeast, rat, chick embryo, alfalfa, and tomato. Smit-McBride, Z., Dever, T. E., Hershey, J. W. B. and Merrick, W. C. (1989a) *J. Biol. Chem.*, 264, 1578–1583; Schnier et al. (1991) (yeast); Sano, A. (1995) in Imahori, M. et al. (eds), *Polyamines, Basic and Clinical Aspects*, VNU Science Press, The Netherlands, 81–88 (rat); Rinaudo, M. S., and Park, M. H. (1992) FASEB J, 6, A453 (chick embryo); Pay, M. H., Wolff, E. C., Smit-McBride, Z., Hershey, J. W. B., and Folk, J. E. (1991) *Plant Mol. Biol.,* 17, 927–929 (alfalfa); Wang, T. W., Lu, L., Wang, D., and Thompson J. E. (2001) *J. Biol. Chem.,* 276, 17541–17549 (tomato).

Expression of eIF-5A mRNA has been explored in various human tissues and mammalian cell lines. For example, changes in eIF-5A expression have been observed in human fibroblast cells after addition of serum following serum deprivation. Pang, J. H. and Chen, K. Y. (1994) *J. Cell Physiol.,* 160, 531–538. Age-related decreases in deoxyhypusine synthase activity and abundance of precursor eIF-5A have also been observed in senescing fibroblast cells, although the possibility that this reflects averaging of differential changes in isoforms was not determined. Chen, Z. P. and Chen, K. Y. (1997b) *J. Cell Physiol.,* 170, 248–254.

Studies have shown that eIF-5A may be the cellular target of viral proteins such as the human immunodeficiency virus type 1 Rev protein and human T cell leukemia virus type 1 Rex protein. Ruhl, M., Himmelspach, M., Bahr, G. M., Himmerschmid, F., Jaksche, H., Wolff, B., Aschauer, H., Farrington, G. K., Probst, H., Bevec, D. and Hauber, J. (1993) *J. Cell Biol.,* 123, 1309–1320; Katahira, J., Ishizaki, T., Sakai, H., Adachi, A., Yamamoto, K. and Shida, H. (1995) *J. Virol,* 69, 3125–3133. Preliminary studies indicate that eIF-5A may interact both with other RNA-binding proteins such as Rev, and also with Rev target RNA, suggesting that these viral proteins may recruit eIF-5A for viral RNA processing. Liu, Y. P., Nemeroff, M., Yan, Y. P. and Chen, K. Y. (1997) *Biol. Signals,* 6, 166–174.

Spermidine, analogs have been successfully used to inhibit deoxyhypusine synthase in vitro, as well as to inhibit the formation of hypusine in vivo, which is accompanied by an inhibition of protein synthesis and cell growth. Jakus, J., Wolff, E. C., Park, M. H., and Folk, J. E. (1993) *J. Biol. Chem.,* 268, 13151–13159; Park, M. H., Wolff, E. C., Lee, Y. B., and Folk, J. E. (1994) J. Biol. Chem., 269, 27827–27832. Polyamines themselves, in particular putrescine and spermidine, also appear to play important roles in cellular proliferation and differentiation. Tabor, C. W. and Tabor, H. (1984) *Annu. Rev. Biochem.,* 53, 749–790; Pegg, A. E. (1988) *Cancer Res.,* 48, 759–774. For example, yeast mutants in which the polyamine biosynthesis pathway has been blocked are unable to grow unless provided with exogenous polyamines. Cohn, M. S., Tabor, C. W., and Tabor, H. (1980) *J. Bacteriol.,* 134, 208–213.

Polyamines have also been shown to protect cells from the induction of apoptosis. For example, apoptosis of thymocytes has been blocked by exposure to spermidine and spermine, the mechanism of which appears to be the prevention of endonuclease activation. Desiderio, M. A., Grassilli. E., Bellesia, E., Salomoni, P. and Franceschi, C. (1995) *Cell Growth Differ.,* 6, 505–513; Brune, B., Hartzell, P., Nicotera, P. and Orrenius, S. (1991) *Exp. Cell Res.,* 195, 323–329. In addition, exogenous polyamines have been shown to repress B cell receptor-mediated apoptosis as well as apoptosis in the unicellular parasite, Trypanosoma cruzi. Nitta, T., Igarashi, K., Yamashita, A., Yamamoto, M., and Yamamoto, N., (2001) *Exptl. Cell Res.,* 265, 174–183; Piacenza, L., Peluffo, G. and Radi, R. (2001) *Proc. Natl. Acad. Sci.,* USA, 98, 7301–7306. Low concentrations of spermine and spermidine have also been observed to reduce the number of nerve cells lost during normal development of newborn rats as well as protect the brain from neuronal damage during cerebral ischaemia. Gilad, G. M., Dornay, M. and Gilad, V. H. (1985) *Brain Res.,* 348, 363–366; Gilad, G. M. and Gilad, V. H. (1991) *Exp. Neurol.,* 111, 349–355.

Polyamines also inhibit senescence, a form of programmed cell death, of plant tissues. Spermidine and putrescine have been shown to delay post-harvest senescence of carnation flowers and detached radish leaves. Wang, C. Y. and Baker, J. E. (1980) *HortScience,* 15, 805–806 (carnation flowers); Altman, A. (1982) *Physiol. Plant.,* 54, 189–193 (detached radish leaves).

In other studies, however, induction of apoptosis has been observed in response to exogenous polyamines. For example, human breast cancer cell lines responded to a polyamine analogue by inducing apoptosis, and excess putrescine has been shown to induce apoptosis in DH23A cells. McCloskey, D. E., Casero, R. A., Jr., Woster, P. M. and Davidson, N. E. (1995) *Cancer Res.,* 55, 3233–3236; Tome, M. E., Fiser, S. M., Payne, C. M. and E. W. Gerner (1997) *Biochem. J,* 328, 847–854.

Apoptosis is currently a field of intense study, and many techniques which may be useful in the control of the apoptotic process are being explored. A great deal of this research has been focused on inducing apoptosis in cancer models, but the prevention of unwanted apoptosis in disease processes is also under investigation. Activation of Jun kinase has been shown to be protective against nitric oxide-induced apoptosis in cardiac myocyte cells. Andreka, P., Zang, J., Dougherty, C., Slepak, T. I., Webster, K. A. and Bishopric, N. H. (2001) *Circul. Res.,* 88, 305–312. Overexpression of anti-apoptotic proteins such as Bcl-2 in T and B lymphocytes has been shown to reduce apoptosis in lymphoid organs following cecal ligation and puncture, and decreased liver apoptosis has been observed in Bcl-2-overexpressing hepatocytes. Hotchkiss, R. S., Swanson, P. E., Knudson, C. M., Chang, K. C., Cobb, J. P., Osborne, D. F., Zollner, K. M., Buchman, T. G., Korsmeyer, S. J. and Karl, I. E. (1999) *J. Immunol.,* 162, 4148–4156; Rodriguez, I., Matsuura, K., Khatib, K., Reed, J. C., Nagata, S. and Vassalli, P. (1996a) *J. Exp. Med.,* 183, 1031–1036. Inhibitors of caspases have also been used to block Fas-mediated apoptosis in the liver. Rodriguez, I., Matsuura, K., Ody, C., Nagata, S. and Vassalli, P. (1996b) *J. Exp. Med.,* 184, 2067–2072.

Inhibition of caspase 1 has also been observed to slow the progression neurodegenerative disease in a mouse model of Huntington's disease. Ona, V. O., Li, M., Vonsattel, J. P., Andrews, L. I., Khan, S. Q., Chung, W. M., Frey, A. S., Menon, A. S., Li, X. J. and Stieg, P. E. et al. (1999) *Nature,* 399, 263–267. Animal models have also been used to demonstrate the efficacy of peptidyl caspase inhibitors in stroke, myocardial infarction, sepsis, and amylotrophic lateral sclerosis. Endres, M., Namura, S., Shimizu-Sasamata, M., Waeber, C., Zhang. L., Gomez-Isla, T., Hyman, B. T. and Moskowitz, M. A. (1998) *J. Cereb. Blood Flow Metab.,* 18, 238–247 (stroke); Wiessner, C., Sauer, D., Alaimo, D. and Allegrini, P. R. (2000) *Cell. Mol. Biol.,* 46, 53–62 (stroke: caspase inhibitor z-VAD-tmk decreased cortical infarct by 45% after permanent middle cerebral artery occlusion in rat); Rabufetti, M., Sciorati, C., Taroxxo. G., Clementi, E., Manfredi, A. A. and Beltramo, M. (2000) *J. Neurosci.,* 20, 4398–4404 (stroke: caspase inhibitor Ac-YVAD-cmk reduced infarct volume and decreased apoptosis, as measured by nucleosome quantitation, by approximately 50% after permanent middle cerebral artery occulusion in rats); Holly, T. A., Drincic, A., Byun, Y., Nakamura, S., Harris, K., Klocke, F. J. and Cryns, V. L. (1999) *J. Mol. Cell. Cardiol.,* 31, 1709–1715 (myocardial infarction: systemic administration of caspase inhibitor YVAD-cmk reduced myocardial infarct size by 31% and reduced the number of apoptotic cells by approximately 70% in rabbits following coronary artery occlusion and reperfusion); Jaeschke, H., Fisher, M. A., Lawson, J. A., Simmons, C. A., Farhood, A. and Jones, D. A. (1998) *J. Immunol.*, 160, 3480–3486 (sepsis: caspase inhibitor z-VAD attenuated apoptosis by 81 to 88% and prevented liver cell necrosis in mice experiencing endotoxin-induced liver damage); Li, M., Ona, V. O., Guegan, C., Chen, M., Jackson-Lewis, V., Andrews, L. J., Olszewski, A. J., Stieg, P. E., Lee, J. P., Predborski, S. and Friedlander, R. M. (2000) *Science,* 288, 335–339 (amylotrophic lateral sclerosis). These studies indicate that apoptosis can be controlled to some degree by targeting the core components of the cell-death machinery. Reed, J. C. and Tomaselli, K. J. (2000).

However, methods for controlling apoptosis and for treating disease by controlling apoptosis are still a largely unexplored area. Failures in the precise regulation of apoptosis are believed to cause or exacerbate such diverse diseases and disorders as neurological neurodegenerative disorders (e.g. Alzheimer's, Parkinson's, Huntington's. Amyotrophic Lateral Sclerosis (Lou Gehrig's), stroke, autoimmune disorders (e.g., rheumatoid arthritis, systemic lupus erythematosus (SLE), multiple sclerosis), Duchenne Muscular Dystrophy (DMD), motor neuron disorders, ischemia, chronic heart failure, infantile spinal muscular atrophy, cardiac arrest, renal failure, atopic dermatitis, sepsis and septic shock, AIDS, hepatitis, glaucoma, diabetes (type I and type 2), asthma, retinitis pigmentosa, osteoporosis, xenograft rejection, and burn injury. Thus, methods of controlling apoptosis are needed.

SUMMARY OF INVENTION

This invention is based, in part, on the discovery and cloning of a full length cDNA encoding a novel apoptosis-induced eIF-5A from rat corpus luteum. The nucleotide sequence and corresponding amino acid sequence arc disclosed herein.

The invention is also based, in part, on the discovery and cloning of a partial length cDNA clone encoding a novel apoptosis-induced deoxyhypusine synthase from rat corpus luteum. The nucleotide sequence and corresponding amino acid sequence are disclosed herein.

The invention provides an eIF-5A cDNA which is up-regulated immediately before the induction of apoptosis. This apoptosis-induced eIF-5A is a suitable target for regulation of apoptosis, including apoptosis underlying disease processes, since it acts in the post-transcriptional regulation of downstream effectors and transcription factors involved in the apoptotic pathway.

The present invention also provides methods for modulating or altering apoptosis, and thus controlling diseases attributable to the induction of apoptosis, by gene therapy. In one embodiment of the invention, apoptosis-induced eIF-5A nucleotide sequences of the invention, fragments thereof, or combinations of such fragments, are introduced into animal/human cells or tissue in reverse orientation to inhibit expression of the endogenous apoptosis-induced eIF-5A gene, thereby reducing the level of endogenous apoptosis-induced eIF-5A protein, and thereby reducing and/or preventing expression of the genes that mediate apoptosis.

In another embodiment of the invention, the apoptosis-induced DHS nucleotide sequence of the invention, fragments thereof, or combinations of such fragments, are introduced into animal/human cells or tissue in reverse orientation to inhibit expression of the endogenous apoptosis-induced DHS gene, and thereby reduce the level of endogenous apoptosis-induced DHS protein, and thereby reducing and/or preventing activation of apoptosis-induced eIF-5a and the ensuing expression of the genes that mediate apoptosis.

In yet another embodiment of the present invention, both the apoptosis-induced DHS sequence and the apoptosis-induced eIF-5A sequence can be used together to reduce the levels of endogenous apoptosis-induced DHS and eIF-5A proteins.

Using the methods of the invention, a vector, such as a viral vector, can be used to achieve transient expression of the apoptosis-induced eIF-5A nucleotide sequence, fragments thereof, and/or combinations of such fragments, or the apoptosis-induced DHS nucleotide sequence, fragments thereof, or combinations of such fragments in the antisense orientation in animal/human cells and tissues.

In one embodiment, the present invention is directed to an isolated DNA molecule encoding apoptosis-induced eIF-5A, wherein the DNA molecule hybridizes with SEQ ID NO:1, or a functional derivative of the isolated DNA molecule which hybridizes with SEQ ID NO:1. In one embodiment of this aspect of the invention, the isolated DNA molecule has the nucleotide sequence of SEQ ID NO:1, i.e., 100% complementarity (sequence identity) to SEQ ID NO:1.

The present invention also is directed to an isolated DNA molecule encoding apoptosis-induced eIF-5A, wherein the DNA molecule hybridizes with SEQ ID NO:3, SEQ ID NO:4 or SEQ ID NO:5, or functional derivatives of the isolated DNA molecule which hybridize with SEQ ID NO:3, SEQ ID NO:4 or SEQ ID NO:5.

The present invention also is directed to an isolated DNA molecule encoding the 3 end of apoptosis-induced DHS, wherein the DNA molecule hybridizes with SEQ ID NO:6, or a functional derivative of the isolated DNA molecule which hybridizes with SEQ ID NO:6. In one embodiment of this aspect of the invention, the isolated DNA molecule has the nucleotide sequence of SEQ ID NO:6, i.e., 100% complementarity (sequence identity) to SEQ ID NO:6.

The present invention also is directed to an isolated DNA molecule encoding the 3' end of apoptosis-induced DHS, wherein the DNA molecule hybridizes with SEQ ID NO:8, or functional derivatives of the isolated DNA molecule which hybridize with SEQ ID NO:8.

In another embodiment of the invention, there is provided an isolated protein encoded by a DNA molecule as described herein above, or a functional derivative thereof. A preferred protein has the amino acid sequence of SEQ ID NO:2, or is a functional derivative thereof. Another preferred protein has the amino acid sequence of SEQ ID NO:7, or is a functional derivative thereof.

Also provided herein is an oligonucleotide or polynucleotide encoding an antisense RNA molecule which is complementary to a corresponding portion of an RNA transcript of a DNA molecule described herein above, wherein the oligonucleotide or polynucleotide hybridizes with the RNA transcript such that expression of endogenous apoptosis-induced eIF-5A is altered in a cell, tissue or organism. In another embodiment of this aspect of the invention, the antisense oligonucleotide or polynucleotide is an RNA molecule that hybridizes to a corresponding portion of an RNA transcript of a DNA molecule described herein above, such that expression of endogenous apoptosis-induced eIF-5A is altered in a cell, tissue or organism. The antisense oligonucleotide or polynucleotide can be full length or preferably has about six to about 100 nucleotides, more preferably about 8 to about 50 nucleotides, even more preferably about 8 to about 30 nucleotides.

The antisense oligonucleotide or polynucleotide may be substantially complementary to a corresponding portion of one strand of a DNA molecule encoding apoptosis-induced eIF-5A, wherein the DNA molecule encoding apoptosis-induced eIF-5A hybridizes with SEQ ID NO:1, SEQ ID NO:3, SEQ ID NO:4, SEQ ID NO:5 or with a combination thereof, or is substantially complementary to at least a corresponding portion of an RNA sequence encoded by the DNA molecule encoding apoptosis-induced eIF-5A. In one embodiment of the invention, the antisense oligonucleotide or polynucleotide is substantially complementary to a corresponding portion of one strand of the nucleotide sequence SEQ ID NO:1, SEQ ID NO:3, SEQ ID NO:4, SEQ ID NO:5 or with a combination thereof, or the RNA transcript transcribed from SEQ ID NO:1, SEQ ID NO:3, SEQ ID NO:4, SEQ ID NO:5 or with a combination thereof. In another embodiment, the antisense oligonucleotide is substantially complementary to a corresponding portion of the 5' non-coding portion or 3' non-coding portion of one strand of a DNA molecule encoding apoptosis-induced eIF-5A, wherein the DNA molecule hybridizes with SEQ ID NO:1, SEQ ID NO:3, SEQ ID NO:4, SEQ ID NO:5 or with a combination thereof.

Alternatively, the antisense oligonucleotide or polynucleotide may be substantially complementary to a corresponding portion of one strand of a DNA molecule encoding apoptosis-induced DHS, wherein the DNA molecule encoding apoptosis-induced DHS hybridizes with SEQ ID NO:6, SEQ ID NO:8, or any combination thereof, or is substantially complementary to at least a corresponding portion of an RNA sequence transcribed from SEQ ID NO:6. SEQ ID NO:8. In one embodiment of the invention, the antisense oligonucleotide or polynucleotide is substantially complementary to a corresponding portion of one strand of the nucleotide sequence SEQ ID NO:6, SEQ ID NO: 8 or a combination thereof, or the RNA transcript encoded is substantially complementary to a corresponding portion of an RNA sequence encoded by a DNA molecule encoding apoptosis-induced DHS. In another embodiment, the antisense oligonucleotide is substantially complementary to a corresponding portion of the 5' non-coding region or 3' non-coding region of one strand of a DNA molecule encoding apoptosis-induced DHS, wherein the DNA molecule hybridizes with SEQ ID NO:6, SEQ ID NO:8 or a combination thereof.

In another embodiment of the invention, a vector for transient expression in animal human cells, comprising (a) an antisense oligo- or polynucleotide substantially complementary to (1) a corresponding portion of one strand of a DNA molecule encoding apoptosis-induced eIF-5A, wherein the DNA molecule encoding apoptosis-induced eIF-5A hybridizes with SEQ ID NO:1, SEQ ID NO:3, SEQ ID NO:4, SEQ ID NO:5, or (2) a corresponding portion of an RNA sequence encoded by the DNA molecule encoding apoptosis-induced eIF-5A; and (b) regulatory sequences operatively linked to the antisense oligo- or polynucleotide such that the antisense oligo- or polynucleotide is transiently expressed in animal/human cells is provided.

In another embodiment of the invention, a vector for transient expression in animal/human cells, comprising (a) an antisense oligo- or polynucleotide substantially complementary to (I) a corresponding portion of one strand of a DNA molecule encoding apoptosis-induced DHS, wherein the DNA molecule encoding apoptosis-induced DHS hybridizes with SEQ ID NO:6, SEQ ID NO:8 or (2) a corresponding portion of an RNA sequence encoded by the DNA molecule encoding apoptosis-induced DHS; and (b) regulatory sequences operatively linked to the antisense oligo- or polynucleotide such that the antisense oligo- or polynucleotide is transiently expressed in animal/human cells is provided.

The invention also provides an animal/human cell, tissue or organ expressing a vector or combination of vectors as described above.

In yet another embodiment, the present invention provides a method of producing an animal human cell, tissue, or organ having a reduced level of apoptosis-induced DHS, apoptosis-induced eIF-5A, or both compared to an unmodified animal/human cell, tissue or organ, comprising: (I) introducing into the animal/human cell, tissue or organ a vector or combination of vectors as described above; (2) allowing transient expression of said vector or combination of vectors; (3) assaying said animal/human cell, tissue or organ for reduced apoptosis-induced DHS activity and/or eIF-5A activity and/or amelioration of the symptoms of apoptosis-induced disease.

Animals/humans or animal/human cells, tissues or organs treated or altered according to the methods of the present invention preferably exhibit reduced apoptosis-induced DHS expression, reduced apoptosis-induced eIF-5A activity, or both, and reduction or elimination of apoptosis-induced disease states.

In another embodiment, the present invention provides a method of modulating expression of endogenous apoptosis-induced eIF-5A in animal/human cells, tissues and organs, said method comprising: (I) introducing into animal/human cells, tissues or organs a vector comprising (a) an antisense oligo- or polynucleotide complementary to (i) at least a portion of one strand of a DNA molecule encoding endogenous apoptosis-induced eIF-5A, wherein the DNA molecule encoding the endogenous apoptosis-induced eIF-5A hybridizes with SEQ ID NO:1, SEQ ID NO:3, SEQ ID NO:4, SEQ ID NO:5, or (ii) at least a portion of an RNA sequence encoded by the endogenous apoptosis-induced eIF-5A gene; and (b) regulatory sequences operatively linked to the antisense oligo- or polynucleotide such that the antisense oligo- or polynucleotide is expressed; and (2) transiently transcribing said antisense oligo- or polynucleotide whereby said transcript binds to said endogenous RNA and expression of said apoptosis-induced eIF-5A gene is modulated, preferably reduced.

In yet another embodiment, the present invention provides a method of modulating, preferably reducing, expression of endogenous apoptosis-induced DHS in animal/human cells, tissues and organs, said method comprising: (1) introducing into animal/human cells, tissues or organs a vector comprising (a) an antisense oligo- or polynucleotide complementary to (i) at least a portion of one strand of a DNA molecule encoding endogenous apoptosis-induced DHS, wherein the DNA molecule encoding the endogenous apoptosis-induced DHS hybridizes with SEQ ID NO:6, SEQ ID NO:8, or (ii) at least a portion of an RNA sequence encoded by the endogenous apoptosis-induced DHS gene; and (b) regulatory sequences operatively linked to the antisense oligo- or polynucleotide such that the antisense oligo- or polynucleotide is expressed; and (2) transiently transcribing said antisense oligo- or polynucleotide whereby said transcript binds to said endogenous RNA and expression of said apoptosis-induced DHS gene is modulated, preferably reduced.

BRIEF DESCRIPTION OF THE DRAWINGS

FIG. 3 depicts the nucleotide sequence and derived amino acid sequence of the 3' end of rat apoptosis-induced eIF-5A cDNA obtained by RT-PCR using as a template total RNA isolated from apoptosing rat corpus luteum 24 hours after the induction of apoptosis by treatment with prostaglandin $F_{2\alpha}$. This partial—length sequence was used for Northern blot analyses. The cDNA sequence is SEQ ID NO.11. The amino acid sequence is SEQ ID NO. 12.

FIG. 4 depicts the nucleotide sequence and derived amino acid sequence of the 5' end of rat apoptosis-induced eIF-5A cDNA obtained by RT-PCR using as a template total RNA isolated from rat corpus luteum 24 hours after the induction of apoptosis by treatment with prostaglandin F2α. The cDNA sequence is SEQ ID NO. 15. The amino acid sequence is SEQ ID NO. 16.

FIG. 5 depicts the nucleotide sequence of rat corpus luteum apoptosis-induced eIF-5A full-length cDNA and the derived amino acid sequence obtained by RT-PCR of total RNA isolated from apoptosing rat corpus luteum. The cDNA sequence is SEQ ID NO. 1. The amino acid sequence is SEQ ID NO. 2.

FIG. 6 is an alignment of the full-length nucleotide sequence of rat corpus luteum apoptosis-induced eIF-5A cDNA with the nucleotide sequence of human eIF-5A (Accession number BC000751 or NM_001970). Human nucleotide sequence (Accession number BC000751 or NM_001970) is SEQ ID NO. 3.

FIG. 7 is an alignment of the full-length nucleotide sequence of rat corpus luteum apoptosis-induced eIF-5A cDNA with the nucleotide sequence of human eIF-5A (Accession number NM-020390). Human nucleotide sequence (Accession number NM-020390) is SEQ ID NO. 4.

FIG. 8 is an alignment of the full-length nucleotide sequence of rat corpus luteum apoptosis-induced eIF-5A cDNA with the nucleotide sequence of mouse eIF-5A (Accession number BC003889). Murine nucleotide sequence (Accession number BC003889) is SEQ ID NO. 5.

FIG. 9 is an alignment of the derived full-length amino acid sequence of rat corpus luteum apoptosis-induced eIF-5A with the derived amino acid sequence of human eIF-5A (Accession number BC000751 or NM_001970).

FIG. 10 is an alignment of the derived full-length amino acid sequence of rat corpus luteum apoptosis-induced eIF-5A with the derived amino acid sequence of human eIF-5A (Accession number NM_020390).

FIG. 11 is an alignment of the derived full-length amino acid sequence of rat corpus luteum apoptosis-induced eIF-5A with the derived amino acid sequence of mouse eIF-5A (Accession number BC003889).

FIG. 13 is a Southern blot of rat genomic DNA probed with $^{32}$P-dCTP-labeled full-length rat corpus luteum apoptosis-induced eIF-5A cDNA. Genomic DNA was cut with restriction enzymes as indicated. Several isoforms of eIF-5A are detectable. The restriction fragment corresponding to the apoptosis-induced isoform of eIF-5A is indicated by a single arrow in the lanes labeled EcoR1 and BamH1, restriction enzymes for which there are no cut sites within the open reading frame. The two restriction fragments of the apoptosis-induced isoform of eIF-5A obtained when genomic DNA is cut with EcoRV, a restriction enzyme for which there is a cut site within the open reading frame, are indicated by double arrows. The data indicate that the apoptosis-induced eIF-5A is a single copy gene.

FIG. 15 depicts the nucleotide sequence and derived amino acid sequence of the 3' end of rat apoptosis-induced DHS cDNA obtained by RT-PCR using as a template total RNA isolated from apoptosing rat corpus luteum 24 hours after the induction of apoptosis by treatment with prostaglandin $F_{2\alpha}$. The cDNA sequence is SEQ ID NO. 6. The amino acid sequence is SEQ ID NO. 7.

FIG. 18 is an alignment of the partial-length nucleotide sequence of rat corpus luteum apoptosis-induced DHS cDNA with the nucleotide sequence of human DHS (Accession number BC000333). Human nucleotide sequence (Accession number BC000333) is SEQ ID NO. 8.

DETAILED DESCRIPTION OF THE INVENTION

Figure 1:
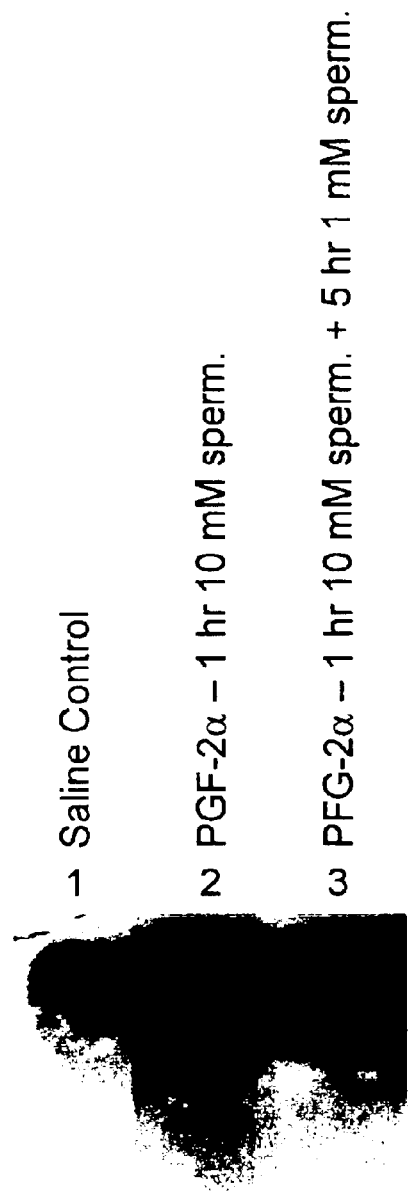
FIG. 1 depicts a DNA laddering experiment in which the degree of apoptosis in dispersed cells of superovulated rat corpora lutea was examined. Superovulation was induced by subcutaneous injection with 500 µg of prostaglandin F2α. Control rats were treated with an equivalent volume of saline solution. Fifteen to thirty minutes later, the ovaries were removed and minced with collagenase. The dispersed cells from rats treated with prostaglandin $F_{2\alpha}$ were incubated in 10 mm glutamine—10 mm spermidine for 1 hour and for a further 5 hours in 10 mm glutamine without spermidine (lane 2) or in 10 mm glutamine+10 mm spermidine for 1 hour and for a further 5 hours in 10 mm glutamine+1 mm spermidine (lane 3). Control cells from rats treated with saline were dispersed with collagenase and incubated for 1 hour and a further 5 hours in glutamine only (lane 1). 500 ng of DNA from each sample was labeled with [$\alpha$-$^{32}$P]-dCTP using klenow enzyme, separated on a 1.8% agarose gel, and exposed to film for 24 hours.

Methods and compositions are provided for altering the expression of apoptosis-induced DHS gene(s), apoptosis-induced eIF-5A gene(s) or both in animal cells. Reduction of expression of apoptosis-induced DHS and apoptosis-induced eIF-5A, either alone or in combination, in animals results in reduced apoptosis and gives rise to novel methods and compositions for the treatment and prevention of diseases caused by, causing, or otherwise having an etiology associated with inappropriate, excessive, or premature apoptosis. As non-limiting examples, the methods and compositions of the present invention may be used to prevent or treat the following apoptosis-associated diseases and disorders: neurological neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, chronic heart failure, stroke, infantile spinal muscular atrophy, cardiac arrest, renal failure, atopic dermatitis, sepsis and septic shock, AIDS, hepatitis, glaucoma, diabetes (type I and type 2), asthma, retinitis pigmentosa, osteoporosis, xenograft rejection, and burn injury.

Animals, preferably mammals, and more preferably humans may be treated using the compositions and methods of the present invention.

Methods and compositions are provided for modulating the expression of apoptosis-induced DHS gene(s), apoptosis-induced eIF-5A gene(s), or both in animal/human cells, tissues, and organs. Modulating expression of apoptosis-induced DHS and apoptosis-induced eIF-5A, either alone or in combination, in animal/human cells, tissues, or organs results in reduction or elimination of the symptoms of diseases attributable to inappropriate, premature, or excess apoptosis.

The general approach to modulating apoptosis, according to the present invention, will be to reduce the amount of active apoptosis-induced eIF-5A in a cell, thereby modulating the apoptotic pathways triggered by active apoptosis-induced eIF-5A.

The incidence of apoptosis may be inhibited, substantially decreased, or delayed by preventing transcription of the gene encoding apoptosis-induced eIF-5A, translation of apoptosis-induced eIF-5A RNA, and/or activation of apoptosis-induced eIF-5A. Activation of apoptosis-induced eIF-5A may be inhibited, substantially decreased, or delayed by preventing transcription of the gene encoding apoptosis-induced DHS and/or translation of apoptosis-induced DHS mRNA. Activation of apoptosis-induced eIF-5A may also be inhibited, substantially decreased, or delayed by blocking the action of apoptosis-induced DHS on apoptosis-induced eIF-5A.

In certain embodiments, the present invention provides methods and compositions for modulating or altering apoptosis, and thus controlling diseases associated with the induction of apoptosis, by gene therapy.

In certain preferred embodiments, the present invention employs antisense constructs, particularly oligonucleotides, for use in modulating the function of nucleic acid molecules encoding apoptosis-induced DHS and or apoptosis-induced eIF-5A, ultimately modulating the amount of apoptosis-induced DHS and or apoptosis-induced eIF-5A produced and or the amount of activated apoptosis-induced eIF-5A produced. This is accomplished by providing antisense compounds which specifically hybridize with one or more nucleic acids encoding apoptosis-induced DHS and or apoptosis-induced eIF-5A.

Thus, in one embodiment of the invention, apoptosis-induced eIF-5A nucleotide sequences of the invention, fragments thereof, or combinations of such fragments, are introduced into animal/human cells or tissue in reverse orientation to modulate expression of the endogenous apoptosis-induced eIF-5A gene, thereby reducing the level of endogenous apoptosis-induced eIF-5A protein, and thereby reducing and/or preventing expression of the genes that mediate apoptosis.

In another embodiment of the invention, apoptosis-induced DHS nucleotide sequence of the invention, fragments thereof, or combinations of such fragments, are introduced into animal/human cells or tissue in reverse orientation to reduce expression of the endogenous apoptosis-induced DHS gene, and thereby reduce the level of endogenous apoptosis-induced DHS protein, and thereby reducing and/or preventing activation of apoptosis-induced eIF-5a and the ensuing expression of the genes that mediate apoptosis.

In yet another embodiment of the present invention, both the apoptosis-induced DHS sequence and the apoptosis-induced eIF-5A sequence can be used together to reduce the levels of endogenous apoptosis-induced DHS and apoptosis-induced eIF-5A proteins.

Apoptosis in cells, tissues, organs, and organisms can also be controlled through the use of other gene therapy methods, such as cosuppression of apoptosis-induced eIF-5A and/or apoptosis-induced DHS. Additional methods include the use of homologous recombination to mutate endogenous apoptosis-induced eIF-5A and or apoptosis-induced DHS, such that fewer copies of functional, active apoptosis-induced eIF-5A and/or apoptosis-induced DHS proteins are produced.

Figure 2:
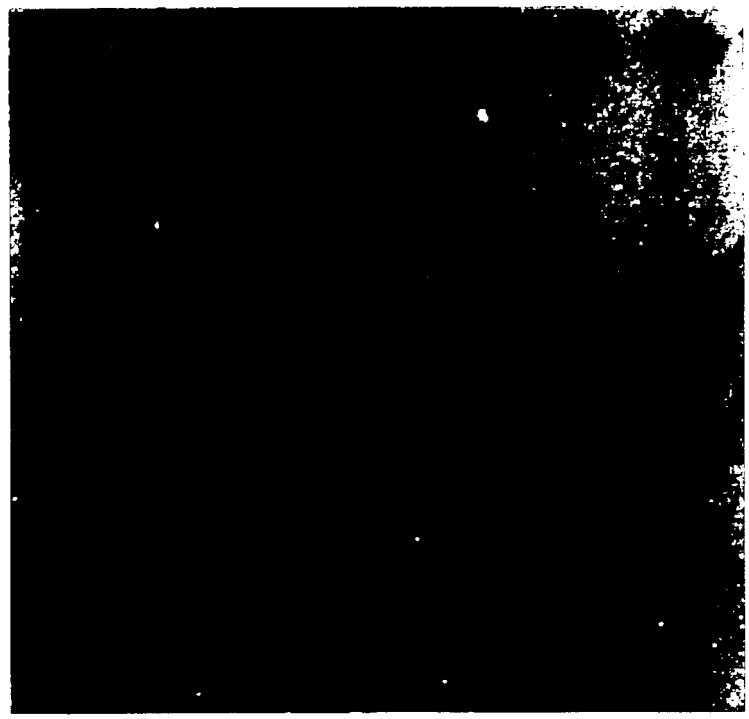
FIG. 2 depicts a DNA laddering experiment in which the degree of apoptosis in superovulated rat corpus lutea was examined in rats treated with spermidine prior to exposure to prostaglandin $F_{2\alpha}$. Superovulated rats were injected subcutaneously with 1 mg/100 g body weight of spermidine, delivered in three equal doses of 0.333 mg/100 g body weight, 24, 12, and 2 hours prior to a subcutaneous injection with 500 µg prostaglandin $F_{2\alpha}$. Control rats were divided into three sets, those which received no injections, those which received three injections of spermidine but no prostaglandin $F_{2\alpha}$, and those which received three injections with an equivalent volume of saline prior to prostaglandin F-,,× treatment. Ovaries were removed front the rats either 1 hour and 35 minutes or 3 hours and 45 minutes after prostaglandin treatment and used for the isolation of DNA. 500 ng of DNA from each sample was labeled with [$\alpha$-$^{32}$P]-dCTP using Klenow enzyme, separated on a 1.8% agarose gel, and exposed to film for 24 hours. Lane 1, no injections (animals were sacrificed at the same time as for lanes 3–5); lane 2, three injections with spermidine (animals were sacrificed at the same time as for lanes 3–5); lane 3, three injections with saline followed by injection with prostaglandin $F_{2\alpha}$(animals were sacrificed 1 h and 35 min after treatment with prostaglandin $F_{2\alpha}$); lane 4, three injections with spermidine followed by injection with prostaglandin $F_{2\alpha}$, (animals were sacrificed 1 h and 35 min after treatment with prostaglandin $F_{2\alpha}$); lane 5, three injections with spermidine followed by injection with prostaglandin $F_{2\alpha}$, (animals were sacrificed 1 h and 35 min after treatment with prostaglandin $F_{2\alpha}$); lane 6, three injections with spermidine followed by injection with prostaglandin $F_{2\alpha}$ (animals were sacrificed 3 h and 45 min after treatment with prostaglandin $F_{2\alpha}$); lane 7, three injections with spermidine followed by injection with prostaglandin $F_{2\alpha}$, (animals were sacrificed 3 h and 45 min after treatment with prostaglandin $F_{2\alpha}$).

Alternatively, the activation of apoptosis-induced eIF-5A by apoptosis-induced DHS can be reduced or blocked by administering chemical inhibitors of the DHS enzymatic reaction. For example, the onset of DNA laddering reflecting apoptosis is delayed in rat corpus luteum when the animals are treated with spermidine, an inhibitor of the DHS reaction after induction of apoptosis by injection of prostaglandin F2, (FIGS. 1 and 2). Jakus, J., Wolff, E. C., Park, M. H., Folk, J. E., "Features of the spermidine binding site of deoxyhypusine synthase as derived from inhibition studies," *Journal of Biological Chemistry* 268: 13151–13159 (1993).

Apoptosis also may be inhibited, substantially decreased, or delayed by adding agents that degrade apoptosis-induced eIF-5A DNA, RNA, or protein, or that degrade apoptosis-induced DHS DNA, RNA, or protein, thereby preventing the activation of apoptosis-induced eIF-5A by apoptosis-induced DHS. In another embodiment of the invention, inhibition of expression of endogenous mammalian apoptosis-induced DHS, apoptosis-induced eIF-5A, or both is affected through the use of ribozymes.

Genetically modified animal/human cells, tissues or organs are defined herein as animal/human cells, tissues or organs containing incorporated heterologous or homologous apoptosis-induced DHS DNA or modified DNA or some portion of heterologous apoptosis-induced DHS DNA or homologous apoptosis-induced DHS DNA that is being transiently expressed. Alternatively, genetically modified animal/human cells, tissues or organs may contain incorporated heterologous or homologous apoptosis-induced eIF-5A DNA or modified DNA or some portion of heterologous apoptosis-induced eIF-5A DNA or homologous apoptosis-induced eIF-5A DNA that is being transiently expressed. The altered genetic material may encode a protein, comprise a regulatory or control sequence, or may be or include an antisense sequence or encode an antisense RNA which is antisense to the endogenous apoptosis-induced DHS or eIF-5A DNA or mRNA sequence or portion thereof of the animal/human cells, tissue or organ.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, e.g., Sambrook, J. et al., Molecular Cloning: A Laboratory Manual, 2nd edition, Cold Spring Harbor Press, Cold Spring Harbor, N.Y., 1989.

The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68° C. for about 3 to 4 hours for fragments of cloned DNA and for about 12 to about 16 hours for total eukaryotic DNA. For lower stringencies, the temperature of hybridization is reduced to about 42° C. below the melting temperature ($T_m$) of the duplex. The $T_m$ is known to be a function of the G-C content and duplex length as well as the ionic strength of the solution.

As used herein, the term "substantial sequence identity" or "substantial homology" is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or in the case of proteins, immunological crossreactivity, similar enzymatic activity, etc. Each of these characteristics can readily be determined by the skilled practitioner by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

As used herein, the phrase "hybridizes to a corresponding portion" of a DNA or RNA molecule means that the molecule that hybridizes, e.g., oligonucleotide, polynucleotide, or an ~nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long antisense molecule from the 3' coding or non-coding region of rat DHS will recognize and hybridize to an approximately 100 nucleotide portion of a nucleotide sequence within the 3' coding or non-coding region, respectively of human DHS gene or any other animal DHS gene so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20–30% larger or smaller, preferably no more than about 12–15% larger or smaller.

The term "functional derivative" of a nucleic acid (or poly- or oligonucleotide) is used herein to mean a fragment, variant, homolog, or analog of the gene or nucleotide sequence encoding apoptosis-induced DHS or apoptosis-induced eIF-5A. A functional derivative may retain at least a portion of the function of the apoptosis-induced DHS or eIF-5A encoding DNA which permits its utility in accordance with the invention. Such function may include the ability to hybridize under low stringency conditions with native human apoptosis-induced DHS or eIF-5A or substantially homologous DNA from another animal which encodes apoptosis-induced DHS or eIF-5A or with an mRNA transcript thereof, or, in antisense orientation, to inhibit the transcription and/or translation of animal/human apoptosis-induced DHS or eIF-5A mRNA, or the like.

A "fragment" of the gene or DNA sequence refers to any subset of the molecule, e.g., a shorter polynucleotide or oligonucleotide. A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different animal genus or species. An "analog" refers to a non-natural molecule substantially similar to or functioning in relation to either the entire molecule, a variant or a fragment thereof.

In the context of the present invention. "modulation" or "alteration" means a decrease or reduction (inhibition) in the expression of a gene. In the context of the present invention, inhibition (reduction) is the preferred form of modulation of gene expression and mRNA is a preferred target. By "altered expression" or "modified expression" of a gene, e.g., the apoptosis-induced DHS gene or apoptosis-induced eIF-5A gene, is meant any process or result whereby the normal expression of the gene, for example, that expression occurring in an unmodified animal/human cell, tissue or organ, is changed in some way. As intended herein, modification or alteration in gene expression preferably is complete or partial reduction in the expression of the apoptosis-induced DHS gene or apoptosis-induced eIF-5A gene or both, but may also include a change in the timing of expression, or another state wherein the expression of the apoptosis-induced DHS gene or apoptosis-induced eIF-5A gene or both differs from that which would be most likely to occur naturally in an unmodified animal/human cell, tissue or organ. A preferred modulation or alteration is one which results in reduction of apoptosis-induced DHS production, apoptosis-induced eIF-5A production, or both by the animal human cell, tissue or organ compared to production in an unmodified animal/human cell, tissue or organ.

The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to the interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of DHS and or eIF-5A and or the amount of activated eIF-5A produced.

In the particular context of antisense, as understood in the present invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

As used herein, the term "target cells" refers to cells undergoing or predicted to undergo excessive, premature, and or inappropriate apoptosis.

As used herein, the terms "target nucleic acid" and "target oligonuccotide" describe an oligonucleotide, preferably within a cell, to which an antisense oligonucleotide of the present invention hybridizes. As used herein, the terms "target nucleic acid" and "target oligonucleotide" also describe an oligonucleotide, preferably within a cell, the expression of which is suppressed by cosuppression techniques, as described herein. Further as used herein, the terms "target nucleic acid" and "target oligonucleotide" also describe an oligonucleotide, preferably within a cell, which are mutated by homologous recombination techniques described herein. Target nucleic acids and target oligonucleotides preferably comprise genomic DNA, pre-RNA, cDNA, or mRNA.

As used herein, the terms, "nucleic acid encoding apoptosis-induced DHS", and "nucleic acid encoding apoptosis-induced eIF-5A" encompass DNA encoding apoptosis-induced DHS, DNA encoding apoptosis-induced eIF-5A, RNA (including pre-mRNA and mRNA) transcribed from such DNA, and also cDNA derived from such RNA.

A full length cDNA sequence encoding a rat eIF-5A gene exhibiting apoptosis-induced expression has been isolated by reverse transcriptase mediated polymerase chain reaction (RT-PCR) using RNA isolated from apoptosing corpus luteum as a template. Polynucleotide probes corresponding to selected regions of the isolated rat corpus luteum cDNA sequence as well as the full length rat corpus luteum cDNA were used to determine the presence of mRNA encoding eIF-5A in apoptosing rat corpus luteum.

The apoptosis-induced eIF-5A gene of the present invention was isolated by using RT-PCR. The 3' end of the gene was isolated first using primers designed according to the yeast, fungi, and human eIF-5A cDNA sequences. The upstream primer used to isolate the 3' end of the rat eIF-5A gene is a 20 nucleotide degenerate primer: 5'TCSAARACHGGNAAGCAYGG 3' (SEQ ID NO. 9), wherein S is selected from C and G; R is selected from A and G; H is selected from A, T, and C; Y is selected from C and T; and N is any nucleic acid.

The downstream primer used to isolate the 3'end of the rat eIF-5A gene contains 42 nucleotides:

```
                                              (SEQ ID NO.10)
5' GCGAAGCTTCCATGGCTCGAGTTTTTTTTTTTTTTTTTTTTT 3'.
                 XhoI
```

Using 5 μg of the downstream primer, a first strand of cDNA was isolated using standard RT-PCR. The first strand was then used as a template in a RT-PCR using both the upstream and downstream primers.

The PCR conditions were 94° C., 5 min, (94° C. 1 min, 48° C. 1 min, 72° C. 2 min for 45 cycles), and 72° C. 15 min. Separation of the RT-PCR products on an agarose gel revealed the presence a 900 bp fragment, which was subcloned into pBluescript™(Stratagene Cloning Systems, LaJolla, Calif.) using blunt end ligation and sequenced (SEQ ID NO. 11).

The 5' end of the rat apoptosis-induced eIF-5A gene was isolated using an upstream primer designed according to human eIF-5A cDNA sequences and a downstream primer designed according to the 3' end of the RT-PCR fragment. The upstream primer is a 24 nucleotide primer:

```
5' CAGGTCTAGAGTTGGAATCGAAGC 3'  (SEQ ID NO.13).
       XhoI
```

The downstream primer contains 30 nucleotides:

```
                                              (SEQ ID NO.14)
5' ATATCTCGAGCCTTGATTGCAACAGCTGCC 3'.
       XhoI
```

Using 5 μg of the downstream primer, a first strand of cDNA was isolated using standard RT-PCR. The first strand was then used as a template in a RT-PCR using both the upstream and downstream primers.

The PCR conditions were 94° C., 5 min, (94° C. 1 min, 48° C. 1 min. 72° C. 2 min for 45 cycles), and 72° C. 15 min. Separation of the RT-PCR products on an agarose gel revealed the presence a 500 bp fragment, which was subcloned into pBluescript™ (Stratagene Cloning Systems, LsJolla, Calif.) using XbaI and XhoI cloning sites present in the upstream and downstream primers, respectively, and sequenced (SEQ ID NO. 15).

The sequences of the 3' and 5' ends of the rat apoptosis-induced eIF-5A (SEQ ID NO. 11 (see also, FIG. 3) and SEQ ID NO. 15 (see also, FIG. 4), respectively) overlapped and gave rise to the full-length cDNA sequence (SEQ ID NO. 1 (see also, FIG. 5)). This full-length sequence was aligned and compared with sequences in the GeneBank data base. The results showed that the rat full-length cDNA sequence encodes eIF-5A. The rat apoptosis-induced eIF-5A cDNA also aligned with human and mouse eIF-5A sequences. See FIGS. 6 through 11.

The nucleotide sequence of the rat apoptosis-induced cDNA clone is shown in SEQ ID NO:1 The cDNA clone encodes a 154 amino acid polypeptide (SEQ ID NO:2) having a calculated molecular mass of 16.8 KDa.

Based on the expression pattern of the identified gene in developing and regressing rat corpus luteum, it is involved in apoptosis. Thus, the cDNA sequence of the invention encoding rat apoptosis-induced eIF-5A can be used as a probe to isolate apoptosis-induced genes from other animal/human cells, tissues and organs, using guidance provided herein and techniques well known to those skilled in the art.

Figure 12:
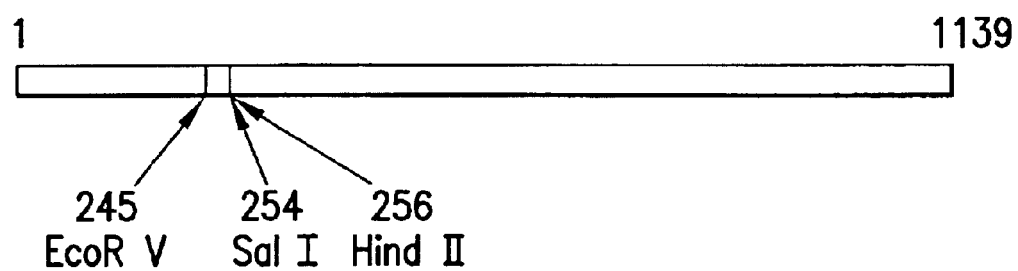
FIG. 12 is a restriction map of rat corpus luteum apoptosis-induced eIF-5A cDNA.

The rat apoptosis-induced eIF-5A gene is a member of an eIF-5A gene family. Genomic Southern blot analysis of rat DNA was carried out using genomic DNA extracted from corpus luteum. The DNA was cut with various restriction enzymes that recognize a single site within the coding region of the eIF-5A gene or which do not recognize any sites within the open reading frame of the eIF-5A gene. A restriction map for rat apoptosis eIF-5A is shown in FIG. 12.

Restriction enzyme digested rat corpus luteum genomic DNA was probed with $^{32}$P-dCTP-labeled full length eIF-5A cDNA. Hybridization under high stringency conditions revealed hybridization of the full length cDNA probe to several restriction fragments for each restriction enzyme digested DNA sample indicating the presence of several isoforms of eIF-5A. Of particular note, when rat genomic DNA was digested with EcoRV, which has a restriction site within the open reading frame of apoptosis-induced eIF-5A (FIG. 12), two restriction fragments of the apoptosis-induced isoform of eIF-5A were detectable in the Southern blot (FIG. 13). These results suggest that the apoptosis-induced eIF-5A is a single copy gene in rat. As shown in FIGS. 6 through 11, the eIF-5A gene is highly conserved across species, and so it would be expected that there is a significant amount of conservation between isoforms within any species.

Figure 14:
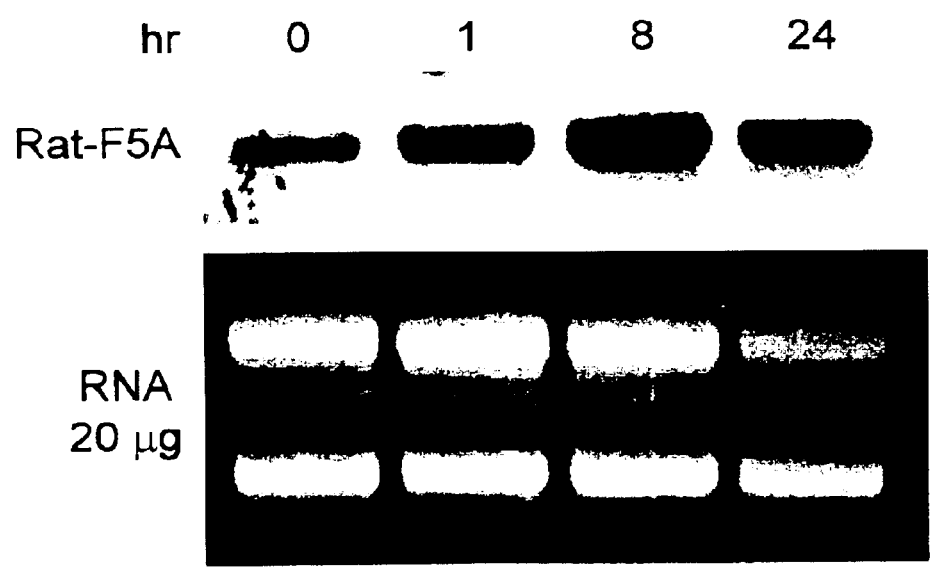
FIG. 14 is a Northern blot of total RNA isolated from apoptosing rat corpus luteum at 0 hours, 1 hour, 8 hours and 24 hours after the induction of apoptosis by treatment with prostaglandin $F_{2\alpha}$c. The top panel is an autoradiograph of the Northern blot probed with the $^{32}$P-dCTP-labeled 3'-end of rat corpus luteum apoptosis-induced eIF-5A cDNA. The lower panel is the ethidium bromide stained gel of total RNA. Each lane contains 20 µg RNA.

Northern blots of apoptosing rat corpus luteum total RNA probed with full length rat apoptosis-induced eIF-5A cDNA show that the expression of apoptosis-induced eIF-5A is significantly enhanced after induction of apoptosis by treatment with prostaglandin $F_{2\alpha}$. Expression of eIF-5A was low at time zero, increased substantially within 1 hour of treatment, increased still more within 8 hours of treatment and decreased again slightly within 24 hours of treatment (FIG. 14).

Apoptosis-induced eIF-5A is a suitable target for regulation of apoptosis, including apoptosis underlying disease processes, since it likely acts in the post-transcriptional regulation of downstream effectors and transcription factors involved in the apoptotic pathway. Thus, it is expected that by substantially repressing the expression of the apoptosis-induced eIF-5A gene in animal/human cells, tissues or organs, diseases attributable to apoptosis can be controlled.

Alternatively, it is expected that by substantially enhancing the expression of the apoptosis-induced eIF-5A gene in animal/human cells, tissues or organs, diseases attributable to an inability to induce apoptosis (e.g cancer) can be controlled.

A partial-length cDNA corresponding to another gene, DHS, which is involved in the induction of apoptosis in animal/human cells, tissues, and organs, has also been isolated and sequenced herein and, like eIF-5A, it can be used to alter apoptosis and control apoptosis-related diseases. The partial-length apoptosis-induced DHS cDNA clone was isolated from apoptosing rat corpus luteum by RT-PCR using primers designed from the human DHS sequence. The upstream primer is a 20 nucleotide primer: 5' GTCTGTGTATTATTGGGCCC 3' (SEQ ID NO. 17). The downstream primer contains 42 nucleotides:

(SEQ ID NO.18)
5'GCGAAGCTTCCATGG<u>CTCGAG</u>TTTTTTTTTTTTTTTTTTTTT 3'.
              XhoI

Using 5 µg of the downstream primer, a first strand of cDNA was isolated using standard RT-PCR. The first strand was then used as a template in a RT-PCR using both the upstream and downstream primers.

The PCR conditions were 94° C., 5 min, (94° C. 1 min, 48° C. 1min, 72° C. 2 min for 45 cycles), and 72° C. 15 min. Separation of the RT-PCR products on an agarose gel revealed the presence a 606 bp fragment, which was subcloned into pBluescript™ (Stratagene Cloning Systems, LaJolla, Calif.) using blunt end ligation and sequenced (SEQ ID NO. 6).

Figure 16:
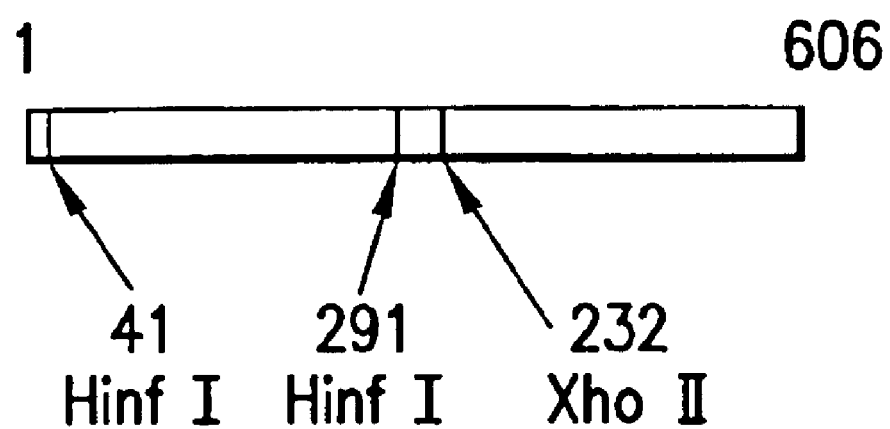
FIG. 16 is a restriction map of partial-length rat apoptosis-induced DHS cDNA.
Figure 17:
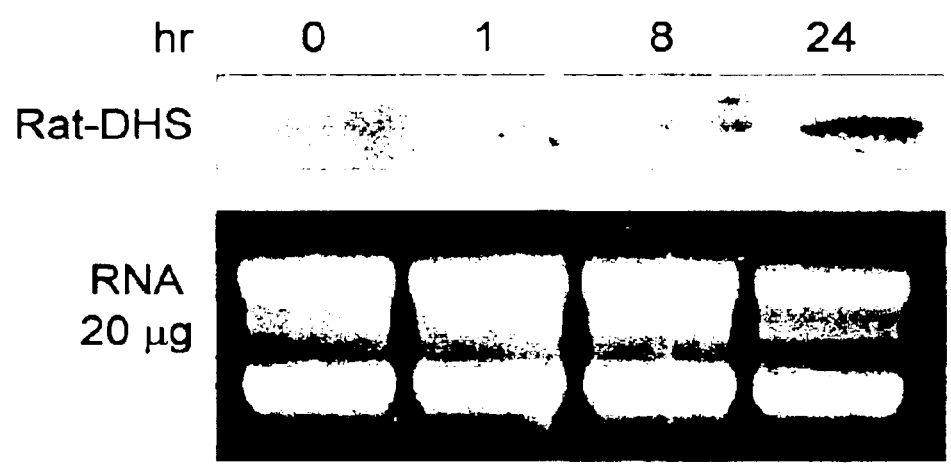
FIG. 17 is a Northern blot of total RNA isolated from apoptosing rat corpus luteum at 0 hours, 1 hour, 8 hours and 24 hours after the induction of apoptosis by treatment with prostaglandin $F_{2\alpha}$. The top panel is an autoradiograph of the Northern blot probed with the $^{32}$P-dCTP-labeled 3'-end of rat corpus luteum apoptosis-induced DHS cDNA. The lower panel is the ethidium bromide stained gel of total RNA. Each lane contains 20 μg RNA.

The nucleotide and derived amino acid sequences for the 3' end of rat apoptosis-induced DHS (SEQ ID NO. 6 and SEQ ID NO. 7, respectively) are shown in FIG. 15. A restriction map of partial-length rat apoptosis-induced DHS cDNA is shown in FIG. 16. As is the case with the eIF-5A gene sequence described herein, the DHS sequence of the present invention can be used to isolate apoptosis-induced DHS genes from other animals, including humans. Isolation of DHS sequences from animals and human can be achieved using art known methods and guidance provided herein, based on sequence similarities of at least 80% across species. The eIF-5A and DHS genes of the invention are up-regulated during apoptosis. Northern blot analyses demonstrate that apoptosis-induced eIF-5A and DHS are both up-regulated in rat corpus luteum over a 24 hour period following induction of corpus luteum apoptosis by treatment with prostaglandin $F_{2\alpha\alpha}$ (FIGS. 14 and 17). For the identification and isolation of the apoptosis-induced DHS gene and eIF-5A gene, in general, preparation of plasmid DNA, restriction enzyme digestion, agarose gel electrophoresis of DNA, polyacrylamide gel electrophoresis of protein, PCR, RT-PCR, Southern blots, Northern blots, DNA ligation and bacterial transformation were carried out using conventional methods well-known in the art. See, e.g., Sambrook, J. et al., Molecular Cloning: A Laboratory Manual, 2nd ed., Cold Spring Harbor Press, Cold Spring Harbor, N.Y., 1989. Techniques of nucleic acid hybridization are disclosed by Sambrook.

In certain embodiments, methods and compositions are provided for modulating apoptosis, and thus controlling diseases associated with apoptosis, by gene therapy. The cloned apoptosis-induced eIF-5A gene, fragment(s) thereof, or cloned apoptosis-induced DHS gene or fragment(s) thereof, or combinations of apoptosis-induced eIF-5A and apoptosis-induced DHS sequences, when introduced in reverse orientation (antisense) into animal/human cells, tissues, organs, or organisms and transiently expressed under the control of a promoter can be used to reduce or prevent apoptosis in said cells, tissues, organs, or organisms and, further, to control apoptosis related diseases in said cells, tissues or organs. Selected antisense sequences from other animals and human which share sufficient sequence identity with the rat apoptosis-induced DHS gene or rat apoptosis induced eIF-5A gene can be us ed to achieve similar genetic modification.

Using methods of the invention, antisense oligonucleotides corresponding to regions of the apoptosis-induced eIF-5A nucleotide sequence, fragments thereof, or combinations of such fragments, and or the apoptosis-induced DHS nucleotide sequence, fragments thereof, or combinations of such fragments can be used to inhibit the expression of apoptosis-induced eIF-5A protein and or apoptosis-induced DHS protein in animal/human cells and tissues.

It is also possible to inhibit expression of apoptosis-induced eIF-5A by inactivating the gene coding for apoptosis-induced eIF-5A in a cell. Such inactivation can occur by deleting the gene in the cell or by introducing a deletion or mutation into the gene thereby inactivating the gene. The gene may also be inactivated by inserting into the gene another DNA fragment such that expression of the endogenous apoptosis-induced eIF-5A protein does not occur. Likewise, it is possible to inhibit activation of apoptosis-induced eIF-5A by inactivating the gene coding for apoptosis-induced DHS in a cell. Methods for introducing mutations, such as deletions and insertions, into genes in eukaryotic cells are known in the art. See, for example, U.S. Pat. No. 5,464,764, which is incorporated herein in its entirety. Oligonucleotides and expression vectors useful for mutation of genes in cells may be made according to methods known in the art and guidance provided herein; for example, methods useful for making and expressing antisense oligonucleotides may be used to make oligonucleotides and expression vectors useful for mutating genes in cells.

It is also possible to inhibit expression of apoptosis-induced eIF-5A by suppressing expression of the gene coding for apoptosis-induced eIF-5A in a cell. Such inactivation can be accomplished via cosuppression, e.g., by introducing nucleotide sequence(s) coding for apoptosis-induced eIF-5A into a cell such that cosuppression occurs. Likewise, it is possible to inhibit activation of apoptosis-induced eIF-5A by suppressing the expression of the gene coding for apoptosis-induced DHS in a cell via cosuppression. Oligonucleotides and expression vectors useful for cosuppression may be made according to methods known in the art and guidance provided herein; for example, methods useful for making and expressing antisense oligonucleotides may be used to make oligonucleotides and expression vectors useful for cosuppression. Methods for cosuppression are known in the art. See, for example, U.S. Pat. No. 5,686,649, which is incorporated herein in its entirety.

One result of the genetic modification (through, e.g., antisense, mutation, or cosuppression) is a reduction in the amount of endogenous translatable apoptosis-induced DHS-encoding mRNA. Consequently, the amount of apoptosis-induced DHS protein produced is reduced, thereby reducing the amount of activated eIF-5A, which in turn reduces translation of apoptosis-induced proteins. Apoptosis is thus inhibited or delayed, since de novo protein synthesis is required for the onset of apoptosis.

Another result of the genetic modification is a reduction in the amount of endogenous translatable apoptosis-induced eIF-5A-encoding mRNA. Consequently, the amount of apoptosis-induced eIF-5A protein is reduced, which in turn reduces translation of apoptosis-induced proteins. Apoptosis is thus inhibited or delayed, since de novo protein synthesis is required for the onset of apoptosis.

Alternatively, the activation of apoptosis-induced eIF-5A by apoptosis-induced DHS can be reduced or blocked by administering chemical inhibitors of the DHS enzymatic reaction. For example, the onset of DNA laddering reflecting apoptosis is delayed in rat corpus luteum when the animals are treated with spermidine, an inhibitor of the DHS reaction after induction of apoptosis by injection of prostaglandin $F_{2\alpha}$ (FIGS. 1 and 2). Jakus, J., Wolff, E. C., Park, M. H., Folk, J. E., "Features of the spermidine binding site of deoxyhypusine synthase as derived from inhibition studies," *Journal of Biological Chemistry* 268: 13151–13159 (1993).

Apoptosis also may be inhibited or substantially decreased by adding agents that degrade apoptosis-induced eIF-5A DNA, RNA, or protein, or that degrade apoptosis-induced DHS DNA, RNA, or protein, thereby preventing the activation of apoptosis-induced eIF-5A by apoptosis-induced DHS. In another embodiment of the invention, inhibition of expression of endogenous mammalian apoptosis-induced DHS, apoptosis-induced eIF-5A, or both is affected through the use of ribozymes.

Thus, in certain embodiments, the present invention is directed to methods for modulating apoptosis in animal/human cells or tissues, and thus controlling diseases attributable to the induction of apoptosis, by drug therapy. Examples of suitable drugs include those that inhibit the activation of eIF-5A by DHS, those that inhibit the activation of eIF-5A by deoxyhypusine hydroxylase, those that inhibit transcription and/or translation of apoptosis-induced DHS, those that inhibit transcription and or translation of apoptosis-induced deoxyhypusine hydroxylase, and those that inhibit transcription or translation of apoptosis-induced eIF-5A. Examples of drugs that inhibit the activation of eIF-5A by DHS are provided in Table 1. Toxicity and irritation data are also provided. Chemicals (drugs) that inhibit either the reaction catalyzed by deoxyhypusine synthase or the reaction catalyzed by deoxyhypusine hydroxylase (which reactions lead to the formation of apoptosis-induced eIF-5A protein) can be administered to animal/human tissues or organs by direct injection or using Alzet osmotic minipumps (e.g., DUROS). A minipump can be surgically implanted near the target tissue or organ and left in place for days to months. This implant can then be used to deliver small volumes of drug into the site immediately surrounding the target tissue, and the drug diffuses into the target tissue or organ along a concentration gradient. Information on controlled drug delivery methods and devices is known in the art, and appropriate devices are commercially available. See, e.g., Marshall J W, et al., Stroke 32(1): 190–8 (2001); Urquhart J, et al., J. Intern. Med. 248(5): 357–76 (2000).

TABLE 1

| Drug | Toxicity | Irritation |
|---|---|---|
| Spermidine | IPR-mouse LD50: 870 mg/kg | Irritant |
| 1,3-Diamino-propane | ORL-rat LD50: 350 μg/kg<br>IPR-mouse LD50: 296 mg/kg<br>SKN-rabbit LD50: 200 μg/kg | SKN-rabbit 50 mg<br>EYE-rabbit 1 mg |
| 1,4-Diamino-butane (putrescine) | ORL-rat LD50: 463 mg/kg<br>IPR-mouse LD50: 1750 mg/kg<br>SKN-rabbit LD50: 1576 μg/kg | Data not available |
| 1,7-Diamino-heptane | Data not available | Irritant |
| 1,8-Diamino-octane | Data not available | SKN-rabbit 500 mg<br>EYE-rabbit 100 mg |

Drugs can also be administered to target cells, tissues, and organs of mammals using liposomes. Liposomes occluding the drug are administered intravenously. Targeting can be achieved by incorporating ligands to specific cell receptors into the liposomes. See, e.g., Kaneda, *Adv Drug Delivery Rev* 43: 197–205 (2000).

In one embodiment, the present invention is directed to an isolated DNA molecule encoding apoptosis-induced eIF-5A, wherein the DNA molecule hybridizes with SEQ ID NO:1, or a functional derivative of the isolated DNA molecule which hybridizes with SEQ ID NO:1. In one embodiment of this aspect of the invention, the isolated DNA molecule has the nucleotide sequence of SEQ ID NO:1, i.e., 100% complementarity (sequence identity) to SEQ ID NO:1.

The present invention also is directed to an isolated DNA molecule encoding apoptosis-induced eIF-5A, wherein the DNA molecule hybridizes with SEQ ID NO:3 (see also, FIG. 6, human sequence), SEQ ID NO:4 (see also, FIG. 7, human sequence), or SEQ ID NO:5 (see also, FIG. 8, mouse sequence), or functional derivatives of the isolated DNA molecule which hybridize with SEQ ID NO:3, SEQ ID NO:4 or SEQ ID NO:5.

The present invention also is directed to an isolated DNA molecule encoding the 3' end of apoptosis-induced DHS, wherein the DNA molecule hybridizes with SEQ ID NO:6, or a functional derivative of the isolated DNA molecule which hybridizes with SEQ ID NO:6. In one embodiment of this aspect of the invention, the isolated DNA molecule has the nucleotide sequence of SEQ ID NO:6, i.e., 100% complementarity (sequence identity) to SEQ ID NO:6.

The present invention also is directed to an isolated DNA molecule encoding the 3' end of apoptosis-induced DHS, wherein the DNA molecule hybridizes with SEQ ID NO:8 (see also, FIG. 18, human sequence), or functional derivatives of the isolated DNA molecule which hybridize with SEQ ID NO:8.

In another embodiment of the invention, there is provided an isolated protein encoded by a DNA molecule as described herein above, or a functional derivative thereof. A preferred protein has the amino acid sequence of SEQ ID NO:2, or is a functional derivative thereof. Another preferred protein has the amino acid sequence of SEQ ID NO:7, or is a functional derivative thereof.

Also provided herein is an antisense oligonucleotide or polynucleotide encoding an RNA molecule which is complementary to a corresponding portion of an RNA transcript of a DNA molecule described herein above, wherein the oligonucleotide or polynucleotide hybridizes with the RNA transcript such that expression of endogenous apoptosis-induced eIF-5A is altered in cells, tissues, and or organisms. In another embodiment of this aspect of the invention, the antisense oligonucleotide or polynucleotide is an RNA molecule that hybridizes to a corresponding portion of an RNA transcript of a DNA molecule described herein above, such that expression of endogenous apoptosis-induced eIF-5A is altered in cells, tissues, and/or organisms. The antisense oligonucleotide or polynucleotide can be full length or preferably has about six to about 100 nucleotides.

The antisense oligonucleotide or polynucleotide may be substantially complementary to a corresponding portion of one strand of a DNA molecule encoding apoptosis-induced eIF-5A, wherein the DNA molecule encoding apoptosis-induced eIF-5A hybridizes with SEQ ID NO:1, SEQ ID NO:3, SEQ ID NO:4, SEQ ID NO:5 or with a combination thereof, or is substantially complementary to at least a corresponding portion of an RNA sequence encoded by the DNA molecule encoding apoptosis-induced eIF-5A. In one embodiment of the invention, the antisense oligonucleotide or polynucleotide is substantially complementary to a corresponding portion of one strand of the nucleotide sequence SEQ ID NO:1, SEQ ID NO:3, SEQ ID NO:4, SEQ ID NO:5 or with a combination thereof, or the RNA transcript transcribed from SEQ ID NO:1, SEQ ID NO:3, SEQ ID NO:4, SEQ ID NO:5 or with a combination thereof. In another embodiment, the antisense oligonucleotide is substantially complementary to a corresponding portion of the 5' non-coding portion or 3' non-coding portion of one strand of a DNA molecule encoding apoptosis-induced eIF-5A, wherein the DNA molecule hybridizes with SEQ ID NO:1, SEQ ID NO:3, SEQ ID NO:4, SEQ ID NO:5 or with a combination thereof.

Alternatively, the antisense oligonucleotide or polynucleotide may be substantially complementary to a corresponding portion of one strand of a DNA molecule encoding apoptosis-induced DHS, wherein the DNA molecule encoding apoptosis-induced DHS hybridizes with SEQ ID NO:6, SEQ ID NO:8, or any combination thereof, or is substantially complementary to at least a corresponding portion of an RNA sequence transcribed from SEQ ID NO:6, SEQ ID NO:8. In one embodiment of the invention, the antisense oligonucleotide or polynucleotide is substantially complementary to a corresponding portion of one strand of the nucleotide sequence SEQ ID NO:6, SEQ ID NO:8 or a combination thereof, or the RNA transcript encoded is substantially complementary to a corresponding portion of an RNA sequence encoded by a DNA molecule encoding apoptosis-induced DHS. In another embodiment, the antisense oligonucleotide is substantially complementary to a corresponding portion of the 5' non-coding region or 3' non-coding region of one strand of a DNA molecule encoding apoptosis-induced DHS, wherein the DNA molecule hybridizes with SEQ ID NO:6, SEQ ID NO:8 or a combination thereof.

In another embodiment of the invention, a vector for transient expression in animal/human cells, comprising (a) an antisense oligo- or polynucleotide substantially complementary to (I) a corresponding portion of one strand of a DNA molecule encoding apoptosis-induced eIF-5A, wherein the DNA molecule encoding apoptosis-induced eIF-5A hybridizes with SEQ ID NO:1, SEQ ID NO:3, SEQ ID NO:4, SEQ ID NO:5, or (2) a corresponding portion of an RNA sequence encoded by the DNA molecule encoding apoptosis-induced eIF-5A; and (b) regulatory sequences operatively linked to the antisense oligo- or polynucleotide such that the antisense oligo- or polynucleotide is transiently expressed in animal/human cells is provided.

In another embodiment of the invention, a vector for transient expression in animal/human cells, comprising (a) an antisense oligo- or polynucleotide substantially complementary to (1) a corresponding portion of one strand of a DNA molecule encoding apoptosis-induced DHS, wherein the DNA molecule encoding apoptosis-induced DHS hybridizes with SEQ ID NO:6, SEQ ID NO:8 or (2) a corresponding portion of an RNA sequence encoded by the DNA molecule encoding apoptosis-induced DHS; and (b) regulatory sequences operatively linked to the antisense oligo- or polynucleotide such that the antisense oligo- or polynucleotide is transiently expressed in animal/human cells is provided.

The regulatory sequences may include a promoter functional in the animal/human cell, which promoter may be inducible or constitutive. Optionally, the regulatory sequences include a polyadenylation signal.

The invention also provides an animal/human cell, tissue or organ expressing a vector or combination of vectors as described above.

In yet another embodiment, the present invention provides a method of producing an animal/human cell, tissue, or organ having a reduced level of apoptosis-induced DHS, apoptosis-induced eIF-5A, or both compared to an unmodified animal/human cell, tissue or organ, comprising: (1) introducing into the animal/human cell, tissue or organ a vector or combination of vectors as described above; (2) allowing transient expression of said vector or combination of vectors; (3) assaying said animal/human cell, tissue or organ for reduced apoptosis-induced DHS activity and/or eIF-5A activity and/or amelioration of the symptoms of apoptosis-induced disease.

Animals/humans or animal/human cells, tissues or organs treated or altered according to the methods of the present invention preferably exhibit reduced apoptosis-induced DHS expression, reduced apoptosis-induced eIF-5A activity, or both, and reduction or elimination of apoptosis-induced disease states.

In another embodiment, the present invention provides a method of inhibiting expression of endogenous apoptosis-induced eIF-5A in animal/human cells, tissues and organs, said method comprising: (1) introducing into animal/human cells, tissues or organs a vector comprising (a) an antisense oligo- or polynucleotide complementary to (i) at least a portion of one strand of a DNA molecule encoding endogenous apoptosis-induced eIF-5A, wherein the DNA molecule encoding the endogenous apoptosis-induced eIF-5A hybridizes with SEQ ID NO:1, SEQ ID NO:3, SEQ ID NO:4, SEQ ID NO:5, or (ii) at least a portion of an RNA sequence encoded by the endogenous apoptosis-induced eIF-5A gene; and (b) regulatory sequences operatively linked to the antisense oligo- or polynucleotide such that the antisense oligo- or polynucleotide is expressed; and (2) transiently transcribing said anti sense oligo- or polynucleotide whereby said transcript binds to said endogenous RNA and expression of said apoptosis-induced eIF-5A gene is inhibited.

In yet another embodiment, the present invention provides a method of inhibiting expression of endogenous apoptosis-induced DHS in animal/human cells, tissues and organs, said method comprising: (1) introducing into animal/human cells, tissues or organs a vector comprising (a) an antisense oligo- or polynucleotide complementary to (i) at least a portion of one strand of a DNA molecule encoding endogenous apoptosis-induced DHS, wherein the DNA molecule encoding the endogenous apoptosis-induced DHS hybridizes with SEQ ID NO:6, SEQ ID NO:8, or (ii) at least a portion of an RNA sequence encoded by the endogenous apoptosis-induced DHS gene; and (b) regulatory sequences operatively linked to the antisense oligo- or polynucleotide such that the antisense oligo- or polynucleotide is expressed; and (2) transiently transcribing said antisense oligo- or polynucleotide whereby said transcript binds to said endogenous RNA and expression of said apoptosis-induced DHS gene is inhibited.

In order for a newly inserted gene or DNA sequence to be expressed, resulting in production of the protein which it encodes, or in the case of antisense DNA, to be transcribed, resulting in an antisense RNA molecule, the proper regulatory elements should be present in proper location and orientation with respect to the gene or DNA sequence. The regulatory regions may include a promoter, a 5'-non-translated leader sequence and a 3'-polyadenylation sequence as well as enhancers and other regulatory sequences.

Expression levels from a promoter which is useful for the present invention can be tested using conventional expression systems, for example by measuring levels of a reporter gene product, e.g., protein or mRNA in extracts of animal/human cells, tissues or organs into which the promoter/reporter gene have been introduced.

The present invention provides antisense oligonucleotides and polynucleotides complementary to the gene encoding rat apoptosis-induced eIF-5A or complementary to a gene or gene fragment from other animal/human cells, tissues or organs, which hybridize with the rat apoptosis-induced eIF-5A gene under low to high stringency conditions. The present invention also provides antisense oligonucleotides and polynucleotides complementary to the gene encoding rat apoptosis-induced DHS or complementary to a gene or gene fragment from other animal/human cells, tissues or organs, which hybridize with the rat apoptosis-induced DHS gene under low to high stringency conditions. Such antisense oligonucleotides should be at least about six nucleotides in length to provide minimal specificity of hybridization and may be complementary to one strand of DNA or mRNA encoding the apoptosis-induced gene or a portion thereof, or to flanking sequences in genomic DNA which are involved in regulating apoptosis-induced DHS or eIF-5A gene expression. The antisense oligonucleotide may be as large as 100 nucleotides or more and may extend in length up to and beyond the full coding sequence for which it is antisense. The antisense oligonucleotides can be DNA or RNA or chimeric mixtures or derivatives or modified versions thereof, single stranded or double stranded.

The action of the antisense oligonucleotide may result in alteration, primarily inhibition, of apoptosis-induced DHS expression, apoptosis-induced eIF-5A expression or both in cells, tissues or organs. For a general discussion of antisense see: Alberts, et al., Molecular Biology of the Cell, 2nd ed., Garland Publishing, Inc. New York, N.Y., 1989 (in particular pages 195–196, incorporated herein by reference).

Preferred antisense oligonucleotides are substantially complementary to a portion of the mRNA encoding apoptosis-induced DHS or apoptosis-induced eIF-5A, the portion of the mRNA being approximately the same size as the antisense oligonucleotide. For example, introduction of the full length cDNA clone encoding apoptosis-induced DHS or eIF-5A in an antisense orientation into an animal/human cell, tissue or organ is expected to result in successfully altered apoptosis-induced DHS and/or eIF-5A gene expression. Introduction of partial sequences, targeted to specific portions of the apoptosis-induced DHS gene or apoptosis-induced eIF-5A gene or both, can be equally effective. The effectiveness of suppression of gene expression can be tested using art-known methods. For example, the effectiveness of suppression of gene expression can be tested ill vitro by Northern blotting or western blotting; and the effectiveness of suppression of gene expression can be tested in situ by immunohistochemistry.

The minimal amount of homology required by the present invention is that sufficient to result in sufficient complementarity to provide recognition of the specific target RNA or DNA and inhibition or reduction of its translation or function while not affecting function of other RNA or DNA molecules and the expression of other genes. While the antisense oligonucleotides of the invention comprise sequences complementary to a corresponding portion of an RNA transcript of the apoptosis-induced DHS gene or apoptosis-induced eIF-5A gene, absolute complementarity, although preferred, is not required. The ability to hybridize may depend on the length of the antisense oligonucleotide and the degree of complementarity. Generally, the longer the hybridizing nucleic acid, the more base mismatches with the apoptosis-induced DHS target sequence or apoptosis-induced eIF-5a target sequence it may contain and still form a stable duplex. One skilled in the art can ascertain a tolerable degree of mismatch by use of standard procedures to determine the melting temperature of the hybridized complex, for example.

The antisense RNA oligonucleotides may be generated intracellularly by transcription from exogenously introduced nucleic acid sequences. The antisense molecule may be delivered to a cell by transformation or transfection or infection with a vector, such as a plasmid or virus into which is incorporated DNA encoding the antisense apoptosis-induced DHS sequence apoptosis-induced eIF-5A sequence or operably linked to appropriate regulatory elements, including a promoter. Within the cell the exogenous DNA sequence is expressed, producing an antisense RNA of the apoptosis-induced DHS gene or the apoptosis-induced eIF-5A gene.

Vectors can be plasmids, preferably, or may be viral or other vectors known in the art to replicate and express genes encoded thereon in animal/human cells or bacterial cells. The vector is transcribed to produce the desired antisense apoptosis-induced DHS RNA or apoptosis-induced eIF-5A RNA. Such plasmid or viral vectors can be constructed by recombinant DNA technology methods that are standard in the art. For example, the vector may be a plasmid vector containing a replication system functional in a prokaryotic host and an antisense oligonucleotide or polynucleotide according to the invention.

An oligonucleotide, preferably between about 6 and about 100 (nucleotides in length and complementary to the target sequence of apoptosis-induced DHS or apoptosis-induced eIF-5A, may be prepared by recombinant nucleotide technologies or may be synthesized from mononucleotides or shorter oligonucleotides, for example. Automated synthesizers are applicable to chemical synthesis of the oligo-and polynucleotides of the invention. Procedures for constructing recombinant nucleotide molecules in accordance with the present invention are disclosed in Sambrook, et al., In: Molecular Cloning: A Laboratory Manual, 2nd ed., Cold Spring Harbor Press, Cold Spring Harbor, N.Y. (1989), which is incorporated herein in its entirety. Oligonucleotides which encode antisense RNA complementary to apopotosis-induced DHS sequence can be prepared using procedures well known to those in the art. Details concerning such procedures are provided in Maniatis, T. et al., Molecular mechanisms in the Control of Gene expression, eds., Nierlich, et al., eds., Acad. Press, N.Y. (1976).

In an alternative embodiment of the invention, inhibition of expression of endogenous human/animal apoptosis-induced DHS, apoptosis-induced eIF-5A or both is the result of co-suppression through over-expression of an exogenous apoptosis-induced DHS or eIF-5A gene or gene fragment or both introduced into animal/human cells, tissues or organs. In this embodiment of the invention, a vector encoding apoptosis-induced DHS, apoptosis-induced eIF-5A or both in the sense orientation is introduced into the cells in the same manner as described herein for antisense molecules. Preferably, the apoptosis-induced DHS or apoptosis-induced eIF-5A is operatively linked to a strong promoter.

In another embodiment of the invention, inhibition of expression of endogenous mammalian apoptosis-induced DHS, apoptosis-induced eIF-5A or both is effected through the use of ribozymes. Ribozymes are RNA molecules exhibiting sequence-specific endoribonuclease activity. An example is the hammerhead ribozyme which cleaves at a UH (where H is an A, C or U residue) recognition site in the target RNA and contains base-pairing regions that direct the catalytic domain of the ribozyme to the target site of the substrate RNA. Ribozymes are highly target-specific and can be designed to inactivate one member of a multigene family or targeted to conserved regions of related mRNAs. See, e.g, Merlo et al., The Plant Cell, 10:1603–1621, 1998. The ribozyme molecule may be delivered to a cell by transformation, transfection or infection with a vector, such as a plasmid or virus, into which is incorporated the ribozyme operatively linked to appropriate regulatory elements, including a promoter. Such a ribozyme construct contains base-pairing arms that direct it to a cleavage site within the apoptosis-induced DHS mRNA, or apoptosis-induced eIF-5A mRNA resulting in cleavage of DHS or eIF-5A mRNA and inhibition of apoptosis-induced DHS and/or eIF-5A expression.

"Functional derivatives" of the apoptosis-induced DHS or apoptosis-induced eIF-5A protein as described herein are fragments, variants, analogs, or chemical derivatives of apoptosis-induced DHS or apoptosis-induced eIF-5A, respectively, which retain at least a portion of the apoptosis-induced DHS or eIF-5A activity or immunological cross reactivity with an antibody specific for apoptosis-induced DHS or apoptosis-induced eIF-5A, respectively. A fragment of the apoptosis-induced DHS or apoptosis-induced eIF-5A protein refers to any subset of the molecule. Variant peptides may be made by direct chemical synthesis, for example, using methods well known in the art. An analog of apoptosis-induced DHS or apoptosis-induced eIF-5A refers to a non-natural protein substantially similar to either the entire protein or a fragment thereof. Chemical derivatives of apoptosis-induced DHS or apoptosis-induced-eIF-5A contain additional chemical moieties not normally a part of the peptide or peptide fragment. Modifications may be introduced into peptide or fragment thereof by reacting targeted amino acid residues of the peptide with an organic derivatizing agent that is capable of reacting with selected side chains or terminal residues.

Oligonucleotide molecules encoding derivatives of apoptosis-induced eIF-5A that do not up-regulate the expression of apoptosis-induced genes and/or apoptosis-induced DHS that do not activate eIF-5A may be produced and used to interfere with transcription and/or translation of endogenous apoptosis-induced eIF-5A and/or apoptosis-induced DHS. Oligonucleotides encoding such non-functional derivatives of apoptosis-induced eIF-5A and/or apoptosis-induced DHS proteins may be produced by art-known methods of producing mutations, and their function may be tested in cell-free systems or in cells. Such oligonucleotides may be delivered to a cell by transformation, transfection or infection with a vector, such as a plasmid or virus, into which is incorporated the oligonucleotide, or as naked DNA or DNA associated with liposomes or other delivery systems. Useful oligonucleotides retain enough similarity to the sequences encoding endogenous apoptosis-induced eIF-5A and/or apoptosis-induced DHS proteins that they knock out the corresponding endogenous gene, or portion thereof, via homologous recombination.

An apoptosis-induced DHS or apoptosis-induced eIF-5A protein or peptide according to the invention may be produced by culturing a cell transformed with a nucleotide sequence of this invention (in the sense orientation), allowing the cell to synthesize the protein and then isolating the protein, either as a free protein or as a fusion protein, depending on the cloning protocol used, from either the culture medium or from cell extracts. Alternatively, the protein can be produced in a cell-free system. Ranu, et al., Meth. Enzymol., 60:459–484, (1979).

In certain preferred embodiments, the present invention employs antisense oligonucleotides, for use in modulating the function of nucleic acid molecules encoding apoptosis-induced DHS and/or apoptosis-induced eIF-5A, ultimately modulating the amount of apoptosis-induced DHS and/or apoptosis-induced eIF-5A produced and/or the amount of activated apoptosis-induced eIF-5A produced. This is accomplished by providing antisense compounds which specifically hybridize with one or more nucleic acids encoding apoptosis-induced DHS and/or apoptosis-induced eIF-5A.

The term "antisense oligonucleotide" is intended to refer to nucleic acids, preferably oligonucleotides, that are complementary to the base sequences of a target DNA or RNA. Thus, the term "antisense apoptosis-induced eIF-5A oligonucleotide" refers to oligonucleotides that are complementary to the base sequences of apoptosis-induced eIF-5A DNA or RNA. Similarly, the term "antisense apoptosis-induced DHS oligonucleotide" refers to oligonucleotides that are complementary to the base sequences of apoptosis-induced DHS DNA or RNA. Antisense oligonucleotides, when introduced into a target cell, specifically bind to their target nucleic acid and interfere with transcription, RNA processing, transport, translation and/or stability.

As used herein, the term "antisense oligonucleotide" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. Thus, this term includes oligonucleotides composed of naturally-occurring nucleobases, sugars and covalent internucleoside (backbone) linkages as well as oligonucleotides having non-naturally-occurring portions which function similarly. Such modified or substituted oligonucleotides may be preferred over native forms because of desirable properties such as, for example, enhanced cellular uptake, enhanced affinity for nucleic acid target and increased stability in the presence of nucleases. Modified oligonucleotides, including oligonucleotide mimetics, will be further described herein.

The antisense oligonucleotides of the present invention are designed so as to interfere with transcription or translation of a target gene upon hybridization with the target gene or transcript.

It is preferred to target specific nucleic acids for antisense. Targeting an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, preferred targets are a nucleic acid molecule encoding apoptosis-induced DHS or a nucleic acid molecule encoding apoptosis-induced eIF-5A.

The targeting process also includes determination of a site or sites within this gene for the antisense interaction to occur such that the desired effect, e.g., modulation of expression of the protein, will result. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

Based upon SEQ ID NO:1 and 3–5 and SEQ ID NO:6 and 8, or upon allelic or homologous genomic and/or cDNA sequences, one of skill in the art can easily choose and synthesize any of a number of appropriate antisense molecules for use in accordance with the present invention. Antisense nucleotides will bind to a complementary region of a target mRNA and inhibit its translation.

Antisense oligonucleotides are generally 12 to 18 nucleotides in length. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides. Wagner et al., Nature Biotechnol. 14:840–844, 1996. Preferably, antisense oligonucleotides according to the present invention comprise a complementary sequence of 16–30 bases.

Although oligonucleotides may be chosen which are antisense to any region of the gene or mRNA transcripts, in certain preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected and at which proteins are not expected to bind. See, e.g., Sainio et al., Cell Mol. Neurobiol. 14(5):439–457, 1994.

Within the context of the present invention, one preferred intragenic targeting site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding DHS or eIF-5A, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Within living cells, mRNA transcripts exist in low energy conformations in which the transcript is highly folded and often interacting with proteins. As a result, only partial sequences within the mRNA transcript are actually available for hybridization. The three-dimension folding pattern of known transcripts can be predicted by RNA folding programs in order to design antisense oligonucleotides against accessible regions of the transcript. For example, the mfold version 3.1 software by Zuker and Turner may be used to predict mRNA secondary structure, accessible portions may be chosen, and antisense nucleotides against these regions may be designed. For additional description of mfold version 3.1 software, see, e.g., Zuker M., et al. "Algorithms and Thermodynamics for RNA Secondary Structure Prediction: A Practical Guide In RNA Biochemistry and Biotechnology, 11–43, J. Barciszewski and B. F. C. Clark, eds., NATO ASI Series, Kluwer Academic Publishers (1999); Mathews DH, et al., "Expanded Sequence Dependence of Thermodynamic Parameters Improves Prediction of RNA Secondary Structure," J. Mol. Biol. 288: 911–40 (1999).

Antisense nucleotides according to the present invention are preferably against portions of the targeted mRNA sequence that are predicted to be accessible. However, in some circumstances, antisense nucleotides against portions of the targeted mRNA sequence that are not predicted to be accessible may the desirable. For example, antisense oligonucleotides directed to a sequence spanning the translation start site of an mRNA molecule have a history of successfully inhibiting translation.

Antisense nucleotides can be tested for effectiveness and efficiency in inhibiting translation by inserting a candidate antisense oligonucleotide into a cell, using art-known methods and methods disclosed herein, and testing for translation of the target protein, again using art-known methods and methods disclosed herein, such as Western blotting with antibodies against the target protein, or portions thereof, and testing for the functionality of the target protein. For example, the efficacy of antisense nucleotides against apoptosis-induced eIF-5A may be tested by measuring apoptosis and/or the levels of proteins the translation of which is affected by eIF-5A by cells having the candidate antisense oligonucleotide inserted, as compared to cells not having the candidate antisense oligonucleotide inserted. As another example, the efficacy of antisense nucleotides against apoptosis-induced DHS may be tested by measuring apoptosis, levels of activated eIF-5A, and/or the levels of proteins the translation of which is affected by eIF-5A by cells having the candidate antisense oligonucleotide inserted, as compared to cells not having the candidate antisense oligonucleotide inserted.

Examples of antisense oligonucleotides against rat eIF-5A include the following:

Antisense Oligo 1: bp 618 to 635 of full-length sequence (18 bp) 5' TTG AAG GGG TGA GGA AAA 3' (SEQ ID NO. 19)

Antisense Oligo 2: bp 845 to 859 of full-length sequence (15 bp) 5' TTG AGT GGG ATA AAG 3' (SEQ ID NO. 20)

Antisense Oligo 3: spanning ATG start (−5 to +13) (18 bp) 5' AAT CAT CTG CCA TTT TAA 3' (SEQ ID NO. 21).

Once one or more target sites have been identified, oligonucleotides are chosen which are sufficiently complementary to the target, i.e., hybridize sufficiently well and with sufficient specificity, to give the desired effect.

Finally, although, SEQ ID Nos: 1, 3, 4, and 5 and SEQ ID Nos: 6 and 8 disclose cDNA sequences, one of ordinary skill in the art may easily derive the genomic DNA corresponding to these sequences. Thus, the present invention also provides for antisense oligonucleotides which are complementary to the genomic DNA corresponding to SEQ ID NOs: 1, 3, 4, 5 and/or SEQ ID NO:6 and 8. Similarly, antisense to allelic or homologous DHS or eIF-5A cDNAs and genomic DNAs are enabled without undue experimentation.

Antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 6 to about 100 nucleobases.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

However, antisense oligonucleotides containing only phosphodiester linkages may be vulnerable to degradation by nucleases. Thus, in certain preferred embodiments, antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein includes oligonucleotides in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages include phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding DHS or eIF-5A polypeptides, together with pharmaceutically acceptable carriers.

To increase stability of the oligonucleotides, they may be synthesized with one or more phosphorothioate linkages in order to decrease degradation by nucleases and to increase the potential for crossing the lipid bilayer. More preferably, the antisense oligonucleotides can be synthesized with two phosphorothioate linkages at both the 5' and 3 ends of the oligonucleotide in order to increase stability.

Specific examples of preferred antisense oligonucleotides useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In certain embodiments, one may wish to employ antisense oligonucleotides which include other elements, for example, those which include C-5 propyne pyrimidines. Oligonucleotides which contain C-5 propyne analogues of uridine and cytidine have been shown to bind RNA with high affinity and to be potent antisense inhibitors of gene expression. Wagner et al., "Antisense Gene Inhibition by Oligonucleotides Containing C-5 Propyne Pyrimidines," Science, 260:1510–1513, June 1993.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$C_1H_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$ O]$_m$$CH_3$, O($CH_2$)$_n$$OCH_3$, O($CH_2$)$_n$ $NH_2$, O($CH_2$)$_n$ $CH_3$, O($CH_2$) $ONH_2$, and O($CH_2$)$_3$ ON [($CH_2$)$_n$ $CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a O($CH_2$)$_2$ ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'—O—$CH_2$—O—$CH_2$—N($CH_3$)$_2$.

Other preferred modifications include 2'-methoxy (2'-O—$CH_3$), 2'-aminopropoxy (2'-$OCH_2$ $CH_2$ $CH_2$ $NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5'position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural"

nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; and 5,681,941, each of which is herein incorporated by reference, and U.S. Pat. No. 5,750, 692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g. di-hexadecyl-rac-glycerol or triethylammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantine acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241; 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense oligonucleotides which are chimeric compounds. "Chimeric" antisense oligonucleotides or "chimeras," in the context of this invention, are antisense oligonucleotides, which contain two or more chemically distinct regions, each made up of at least one monomer unit, e.g., a nucleotide in the case of an oligonucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense oligonucleotides used in accordance with this invention may be conveniently and routinely made through the well-known technique of solid phase synthesis. Nucleic acids of any desired sequence may be synthesized using, e.g., automated synthesis machines, which are commercially available. Examples of such machines include the Expedite™ 8909 Nucleic Acid Synthesizer from Applied BioSystems and the ÄKTA OligoPilot DNA/RNA Synthesizer from Amersham Pharmacia Biotech.

Any other means for such synthesis known in the art may additionally or alternatively be employed. It is well known to use similar techniques to prepare oligonucleotides such as the phosphorothioates and alkylated derivatives.

The antisense oligonucleotides used in accordance with this invention may also be made through the use of an expression construct. Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense oligonucleotides. Expression constructs can be used to produce gene products, such as mRNA and proteins, in vitro in cell culture, and can also be used to produce gene products ex vivo and in vivo, making them useful for e.g. gene therapy applications.

For in vitro production, cell culture techniques are well documented in the art and are disclosed herein by reference. Freshner, "Animal Cell Culture: A Practical Approach," Second Edition, Oxford/N.Y., IRL Press, Oxford University Press, 1992.

Expression constructs containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (or RNA) encoding DI-IS and/or eIF-5A polypeptide or fragment or variant thereof. That heterologous DNA/RNA is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710–4716, 1996). Still another preferred expression vector is an adenovirus, described by Stratford-Perricaudet, which is defective for E1 and E3 proteins (J. Clin. Invest. 90:626–630, 1992). The use of the adenovirus as an Adeno.P1A recombinant is disclosed by Warnier et al., in intradermal injection in mice for immunization against P1A (Int. J. Cancer, 67:303–310, 1996).

The invention also embraces expression kits", which allow the artisan to prepare a desired expression vector or vectors. Such expression kits include at least separate portions of each of the previously discussed coding sequences. Other components may be added, as desired, as long as the previously mentioned sequences, which are required, are included.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell: Generally speaking, such a promoter might include either a human or viral promoter. For example, promoters include those derived from HSV, including the α4 promoter. Another exemplary promoter is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

A baculovirus system, which would involve high level expression from the powerful polyhedron promoter, may also be used for expression of antisense oligonucleotides in vitro.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements. Bittner et al., Methods in Enzym, 153:516–544, 1987.

Expression constructs may be replicated by, e.g., the use of a cloning vector. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

The antisense oligonucleotides of the invention may be synthesized in vitro or may be produced in vivo via genetic vector constructs designed to direct the in vivo synthesis of antisense molecules.

In order to effect expression of constructs encoding genes of interest, the expression construct must be delivered into a cell. The cell can be in vitro, ex vivo, or in vivo.

Mechanisms for delivery that may be used to transfer expression vectors into cells of interest include vectors such as plasmids, phagemids, and viral systems.

One mechanism for delivery is via viral infection, where the expression construct is encapsidated in a viral particle which will deliver either a replicating or non-replicating nucleic acid. In certain embodiments, the preferred vector is an HSV vector, although virtually any vector would suffice, and vectors known to be more or less appropriate for different purposes are known to the art. Similarly, where viral vectors are used to deliver other therapeutic genes, inclusion in these vectors of a gene or genes according to the present invention advantageously will protect the cell from virally induced apoptosis, thereby facilitating gene therapy using other gene constructs.

The ability of certain viruses to enter cells via receptor-mediated endocytosis and to integrate into host cell genome and express viral genes stably and efficiently have made them attractive candidates for the transfer of foreign genes into mammalian cells. Ridgway, In: Vectors, A Survey of Molecular Cloning Vectors and Their Uses, Rodriquez and Denhardt, (Eds.), Boston: Butterworths, Chapter 24:467–492, 1988; Nicolas and Rubenstein, In: Vectors, A Survey of Molecular Cloning Vectors and Their Uses, Rodriguez and Denhardt (Eds.), Boston: Butterworths, Chapter 25:493–513, 1988; Baichwal and Sugden, In: GENE TRANSFER Kucherlapati, R., ed. New York: Plenum Press, pp. 117–148, 1986; Temin, In: Gene Transfer, Kucherlapati (Ed.), New York: Plenum Press, Chapter 6:149–188, 1986. The first viruses used as vectors were DNA viruses including the papovaviruses (simian virus 40, bovine papilloma virus, and polyoma). Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of producing mRNA and/or proteins of interest or (ii) to transform cells in vitro or in vivo to provide therapeutic mRNA and/or polypeptides in a gene therapy scenario.

In one embodiment, the vector is HSV. Because HSV is neurotrophic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency, make it useful as a vector. And though much attention has focused on the neurotrophic applications of HSV, this vector also can be exploited for other tissues.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al., Annu Rev Microbiol, 49:675–710, 1995.

Adenovirus, adeno-associated virus, herpes virus, vacciniavirus, retroviruses, or other viral vectors may be used as a gene transfer delivery system for a therapeutic genetic construct. Viral vectors which do not require that the target cell be actively dividing, such as adenoviral and adeno-associated vectors, are particularly useful when the target cells are not proliferative. Numerous vectors useful for this purpose are generally known. See, e.g., Miller, Human Gene Therapy 15-14, 1990; Friedman, Science 244: 1275–1281, 1989; Eglitis and Anderson, BioTechniques 6: 608–614, 1988; Tolstoshev and Anderson, Current Opinion in Biotechnology 1: 55–61, 1990; Sharp, The Lancet 337: 1277–1278, 1991; Cornetta et al., Nucleic Acid Research and Molecular Biology 36: 311–322, 1987; Anderson, Science 226: 401–409, 1984; Moen, Blood Cells 17: 407–416, 1991; and Miller and Rosman, Bio Techniques 7: 980–990, 1989; Le Gal La Salle et al., Science 259: 988–990, 1993; and Johnson, Chest 107: 77S–83S, 1995). Retroviral vectors are particularly well developed and have been used in clinical settings (Rosenberg et al., N. Engl. J. Med 323: 370, 1990; Anderson et al., U.S. Pat. No. 5,399,346.

A viral vector can be made target specific by inserting an apoptosis-regulating gene sequence of interest into the viral vector, along with another gene which encodes the ligand for a receptor on a specific target cell. Viral vectors can be made target specific by attaching, for example, a sugar, a glycolipid, or a protein. Targeting may also be accomplished by using an antibody to target the viral vector. Those of skill in the art will know of, or can readily ascertain without undue experimentation, specific polynucleotide sequences which can be inserted into the viral genome or attached to a viral envelope to allow target specific delivery of viral vectors.

Since recombinant viruses used as vectors are defective, they require assistance in order to produce infectious vector particles. This assistance can be provided, for example, by using helper cell lines that contain plasmids encoding all of the structural genes of the virus under the control of regulatory sequences within the viral genome. These plasmids are missing a nucleotide sequence which enables the packaging mechanism to recognize a polynucleotide transcript for encapsidation. These cell lines produce empty virons, since no genome is packaged. If a viral vector is introduced into such cells in which the packaging signal is intact, but the structural genes are replaced by other genes of interest, the vector can be packaged and vector virion produced.

For example, using the methods of the invention, an adenovirus vector [which may be obtained from, e.g., Microbix Biosystems Inc. (Toronto, Canada)] can be used to achieve transient expression of the apoptosis-induced eIF-5A nucleotide sequence, fragments thereof, and/or combinations of such fragment, or the apoptosis-induced DHS nucleotide sequence, fragments thereof, or combinations of such fragment in the antisense orientation in animal/human cells and tissues. Adenoviruses are widely used for transient expression of DNA in both cultured cells and animals due to their ability to infect a wide range of cell types. One example of an appropriate adenovirus vector contains deletions in the E1 and E3 regions to render the adenovirus non-infectious except when introduced into the E1-complementing 293 cells used for propagation of the virus. The adenovirus vector also expresses FLP recombinase to allow introduction of desired DNA by site-specific recombination between the adenovirus and a shuttle vector carrying the DNA of interest. The DNA to be expressed is subcloned downstream of the constitutively expressed murine cytomegalovirus immediate early gene promoter in the pDC516 shuttle vector provided with the adenovirus construction kit. The shuttle vector containing the DNA to be expressed is then cotransfected with the adenovirus vector, pBHGfrtΔE1,3 FLP, into the E1-complementing 293 cell line. Cotransfection of these two plasmids introduces the promoter and the DNA to be expressed into the adenovirus vector while simultaneously removing the recombinase gene. The adenovirus vector is replication-competent in the E1-complementing cells, and plaques containing recombinant adenovirus vector can be isolated and purified by cesium chloride banding approximately 10 days after cotransfection.

Recombinant adenovirus can be delivered to cultured cells by simply adding the virus to the culture media. Infection of host animals/humans can be achieved by directly injecting the viral particles into the bloodstream or into the desired tissue. The half-life of the virus in serum can be extended by complexing the virus with liposomes (e.g. Lipofectin, Life Technologies) or polyethylene glycol. The adenovirus vector normally enters the cell through an interaction between the knob domain of the viral fiber protein and the coxsackievirus and adenovirus receptor, CAR. The viral vector can be directed to specific cells, or to cells which do not express the CAR, by genetically engineering the virus to express a ligand specific to a certain cell receptor.

Non-viral approaches may also be employed for the introduction polynucleotides, e.g., antisense polynucleotides, into cells otherwise predicted to undergo or undergoing excessive, premature, and/or inappropriate apoptosis. For example, an antisense polynucleotide may be introduced into target cell by the techniques of colloidal dispersion; asialorosonucoid-polylysine conjugation; or microinjection under surgical conditions. See, e.g., Felgner et al., Proc. Natl. Acad. Sci. USA 84: 7413, 1987; Ono et al., Neuroscience Lett 117: 259, 1990; Brigham et al., Am. J. Med. Sci. 298: 278, 1989; Staubinger and Papahadjopoulos, Meth. Enz. 101: 512, 1983; Wu and Wu, J. Biol. Chem. 263: 14621, 1988; Wu et al., J. Biol. Chem. 264: 16985, 1989; Wolff et al., Science 247: 1465, 1990. Additional examples include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection. See, e.g., Graham and Van Der Eb, Virology, 52:456–467, 1973 (phosphate precipitation); Chen and Okayama, Molecular and Cellular Biology, 7(8):2745–2752, 1987 (phosphate precipitation); Rippe et al., Mol Cell Biol, 10(2):689–695, 1990 (phosphate precipitation); Gopal, Molecular and Cellular Biology, 5(5): 1188–1190, 1985 (DEAE-dextran); Tur-Kaspa et al., Mo. Cell. Biol. 6(2):716–718, 1986 (electroporation); Potter et al., Proc. Natl. Acad. Sci., USA, 81:7161–7165, 1984 (electroporation); Harland and Weintraub, J. Cell Biol, 101:1094–1099, 1985 (direct microinjection); Nicolau and Sene, Biochimica et Biophysica Acta, 721:185–190, 1982 (DNA-loaded liposomes and lipofectamine-DNA complexes); Fraley et al., Proc. Natl. Acad. Sci., USA, 76(7):3348–3352, 1979 (DNA-loaded liposomes and lipofectamine-DNA complexes); Fechheimer et al., Proc. Natl. Acad. Sci., USA, 84:8463–8467, 1987 (cell sonication); Yang et al., Proc. Natl. Acad. Sci., USA, 87:9568–9572, 1990 (gene bombardment using high velocity microprojectiles); Wu and Wu, J. Biol Chem, 262(10): 4429–4432, 1987 (receptor-mediated transfection); and Wu and Wu, Biochemistry, 27:887–892, 1988 (receptor-mediated transfection).

In another embodiment of the invention, the expression construct may simply consist of naked recombinant DNA or plasmids. Transfer of the construct may be performed by any of the methods discussed herein which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them. Klein et al., Nature, 327:70–73, 1987. Several devices for accelerating small particles have been developed. One such device relies on a high voltage discharge to generate an electrical current, which in turn provides the motive force. Yang et al., Proc. Nat'l Acad. Sci. USA, 87:9568–9572, 1990. The microprojectiles used have consisted of biologically inert substances such as tungsten or gold beads.

Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. In a further embodiment of the invention, the expression construct may be entrapped in a liposome. Liposomes are vesicular structures characterized by a phospholipid bilayer membrane and an inner aqueous medium. These artificial membrane vesicles are useful as delivery vehicles in vitro and in vivo. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Ghosh and Bachhawat, In: Liver Diseases, Targeted Diagnosis and Therapy Using Specific Receptors and Ligands, Wu and Wu (Eds.), New York: Marcel Dekker, Inc., pp. 87–104, 1991. Also contemplated are lipofectamine-DNA complexes.

It has been shown that large unilamellar vesicles (LUV), which range in size from 0.2–4.0 µm, can encapsulate a substantial percentage of an aqueous buffer containing large macromolecules. RNA, DNA and intact virons can be encapsulated within the aqueous interior and be delivered to cells in a biologically active form. Fraley, et al., Trends Biochem. Sci., 6: 77, 1981. In addition to mammalian cells, liposomes have been used for delivery of polynucleotides in plant, yeast and bacterial cells. In order for a liposome to be an efficient gene transfer vehicle, the following characteristics should preferably be present: encapsulation of the genes of interest at high efficiency while not compromising their biological activity; preferential and substantial binding to a target cell in comparison to non-target cells; delivery of the aqueous contents of the vesicle to the target cell cytoplasm at high efficiency; and (Kinoshita, et al., supra) accurate and effective expression of genetic information (Mannino, et al., Bio Techniques, 6: 682, 1988). See, e.g., Zakut and Givol, Oncogene, 11(2): 393, 1995; Fearnhead, et al., Febs Letter, 375(2): 303, 1995; Korsmeyer, S. J., Trends in Genetics, 11(3):101, 1995; Kinoshita, et al., Oncogene, 10(11): 2207, 1995. Additional discussion of the production and use of liposomes is provided herein.

The composition of the liposome is usually a combination of phospholipid, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Liposome-mediated nucleic acid delivery and expression of foreign DNA in vitro has been very successful. Wong et al. demonstrated the feasibility of liposome-mediated delivery and expression of foreign DNA in cultured chick embryo, HeLa, and hepatoma cells. Wong, et al., Gene, 10 (1980) 87–94. In certain embodiments of the invention, the liposome may be complexed with a hemagglutinating virus (HVJ). Such complexing has been shown to facilitate fusion with the cell membrane and promote cell entry of liposome-encapsulated DNA. Kaneda et al., Science, 243:375–378, January 1989. In other embodiments, the liposome may be complexed or employed in conjunction with nuclear non-histone chromosomal proteins (HMG-1). Kato et al., J. Biol Chem, 266(6):3361–3364, February 1991. In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver genes of interest into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific. Wu and Wu, Advanced Drug delivery Reviews, 12: 159–167 (1993) (delivery to liver).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin. Wu and Wu (1987) (ASOR); Wagner et al., Science, 260:1510–1513, 1990 (transferrin). Recently, a synthetic neoglycoprotein, which recognizes the same receptor as ASOR, has been used as a gene delivery vehicle. Ferkol et al., FASEB Journal, 7:1081–1091, 1993; Perales et al., Proc. Natl. Acad. Sci., USA, 91:4086–4090, 1994. Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Gene therapy may also be accomplished by direct administration of the apoptosis-regulating polynucleotide to a cell. The polynucleotide may be produced and isolated by any standard technique. For example, mRNA is most readily produced by in vitro transcription using a cDNA under the control of a high efficiency promoter (e.g., the T7 promoter). Administration of mRNA to accumulated cells is carried out by any of the methods for direct nucleic acid administration described herein and known in the art.

Many of the gene transfer techniques that generally are applied in vitro have been or can be adapted for ex vivo or in vivo use. For example, selected organs including the liver, skin, and muscle tissue of rats and mice have been bombarded in vivo. Yang et al., 1990; Zelenin et al., FEBS Lett., 280:94–96, 1991. Naked DNA also has been used in clinical settings to effect gene therapy. These approaches may require surgical exposure of the target tissue or direct injection into the target tissue. Nicolau et al. (1987) accomplished successful liposome-mediated gene transfer in rats after intravenous injection. Nicolau et al., Methods Enzymol., 149:157–176, 1987.

Dubensky et al. (1984) successfully injected polyomavirus DNA in the form of $CaPO_4$ precipitates into liver and spleen of adult and newborn mice demonstrating active viral replication and acute infection. Dubensky et al, Proc. Nat'l Acad. Sci. USA, 81:7529–7533, 1984. Benvenisty and Neshif (1986) also demonstrated that direct intraperitoneal injection of $CaPO_4$ precipitated plasmids results in expression of the transfected genes. Benvenisty & Neshif, Proc. Nat'l Acad. Sci. USA 83:9551–9555, 1986. Thus, it is envisioned that DNA encoding an antisense oligonucleotides also may be transferred in a similar manner in vivo.

As another example, a procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention. Methods for in vivo gene therapy are known in the art. For example, viral means of introducing DNA into mammalian cells are known in the art. In particular, a number of vector systems are known for the introduction of foreign or native genes into mammalian cells. These include SV4( ) virus (See, e.g., Okayama et al. (1985) Molec. Cell Biol. 5:1136–1142); Bovine papilloma virus (See, e.g., DiMaio et al. (1982) Proc. Natl. Acad. Sci. USA 79:4030–4034); adenovirus (See, e.g., Morin et al. (1987) Proc. Natl. Acad. Sci. USA 84:4626; is Yifan et al. (1995) Proc. Natl. Acad. Sci. USA 92:1401–1405; Yang et al. (1996) Gene Ther. 3:137–144; Tripathy et al. (1996) Nat. Med. 2:545–550; Quantin et al. (1992) Proc. Natl. Acad. Sci. USA 89:2581–2584; Rosenfeld et al. (11991) Science 252:431–434; Wagner (1992) Proc. Natl. Acad. Sci. USA 89:6099–6103; Curiel et al. (1992) Human Gene Therapy 3:147–154; Curiel (1991) Proc. Natl. Acad. Sci. USA 88:8850–8854; LeGal LaSalle et al. (1993) Science 259:590–599); Kass-Eisler et al. (1993) Proc. Natl. Acad. Sci. USA 90:11498–11502); adeno-associated virus (See, e.g., Muzyczka et al. (1994) J. Clin. Invest. 94:1351; Xiao et al. (1996) J. Virol. 70:8098–8108); herpes simplex virus (See, e.g., Geller et al. (1988) Science 241:1667; Huard et al. (1995) Gene Therapy 2:385–392; U.S. Pat. No. 5,501,979); retrovirus-based vectors (See, for example, Curran et al. (1982) J. Virol. 44:674–682; Gazit et al. (1986) J. Virol. 60:19–28; Miller, A. D. (1992) Curr. Top. Microbiol. Immunol. 158:1–24, Cavanaugh et al. (1994) Proc. Natl. Acad. Sci. USA 91:7071–7075; Smith et al. (1990) Molecular and Cellular Biology 10:3268–3271); herein incorporated by reference. See also, Wu et al. (1991) J. Biol. Chem. 266:14338–14342; Wu and Wu (J. Biol. Chem. (1988)) 263:14621–14624; Wu et al. (1989) J. Biol. Chem. 264:16985–16987; Zenke et al. (1990) Proc. Natl. Acad. Sci. USA 87:3655–3659; Wagner et al. (1990) 87:3410–3414, Jolly, Cancer Gene Therapy (1994) 1:51–64.

For any of the above approaches, therapeutic antisense polynucleotide constructs and/or other therapeutic agents are preferably applied to the site where reduction in apoptosis is desirable (e.g., by injection), but may also be applied to tissue in the vicinity of the needed modulation of apoptosis, or, for example, to a blood vessel supplying the cells in which modulation of apoptosis is desirable. Additionally, therapeutic antisense polynucleotide constructs and/or other therapeutic agents may be administered systemically.

In the gene delivery constructs of the instant invention, poly- or oligonucleotide expression may be directed from any suitable promoter (e.g., the human cytomegalovirus, simian virus 40, actin or adenovirus constitutive promoters; or the cytokine or metalloprotease promoters for activated synoviocyte specific expression). Furthermore, poly- or oligonucleotide production may be regulated by any desired mammalian regulatory element or other appropriate regulatory element. Such enhancers include, without limitation, those enhancers which are characterized as tissue or cell specific in their expression.

Drugs, chemicals, liposomes, vectors, naked oligonucleotides, and other compositions according to the present invention mat be formulated with pharmaceutically acceptable carriers for administration in vivo, ex vivo, or in vitro.

The compositions of this invention may be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application. The preferred compositions are in the form of injectable or infusible solutions.

Effective dosages and scheduling regimens of administration of antibodies according to the present invention can be determined by the skilled practitioner using art-known methods, such as clinical trials and animal studies. Concentrations of the administered substances will vary depending upon the therapeutic or preventive purpose.

Formulations according to the present invention may be administered orally, intravenously, intramuscularly, subcutaneously, topically, intratracheally, intrathecally, intraperitoneally, rectally, vaginally, intracerebrospinally, via inhalation, topically, or intrapleurally. A preferred mode of administration is intraperitoneal injection. Another preferred mode of delivery is injection at the site of, near, or into the vasculature surrounding target cells. Yet another preferred mode of delivery is placement of a sustained release or other implant at the site of or near target cells.

If formulations according to the present invention are administered orally, they may be administered in the form of a tablet, a pill, a liquid or a capsule. Liquid formulations comprising compounds according to the present invention may also be formulated as sprays, which may be formulated to be suitable for, e.g., spraying into the mouth or spraying onto a wound and/or the surrounding area.

Compositions according to the present invention may be administered as buccal, lingual, or sublingual tablets, capsules, or lozenges.

A liquid may be administered in the form of a solution or a suspension. The liquid dosage form may comprise, for example, an alcohol-base or may be formulated with a cyclodextrin such as hydroxypropyl-β-cyclodextrin.

Formulations produced in accordance with the invention may comprise conventional pharmaceutically acceptable diluents or carriers. Tablets, pills, liquids and capsules may include conventional excipients such as lactose, starch, cellulose derivatives, hydroxypropyl methylcellulose and magnesium stearate. Conventional enteric coatings may also be used.

Dosage forms such as oral, rectal, vaginal, and internal implants may be formulated for immediate release or for delayed release Likewise, such dosage forms may be in a sustained-release formulation or in a once a day formulation.

Suppositories may include excipients such as waxes and glycerol. Injectable solutions will comprise sterile pyrogen-free media such as saline and may include buffering agents, stabilizing agents, solubilizing agents or preservatives.

Compositions for topical administration may be in the form of creams, ointments, lotions, solutions, transdermal delivery systems, transdermal patches, foams, or gels.

All citations throughout the specification and the references cited therein are hereby expressly incorporated by reference.

Having now generally described the invention, the same will be more readily understood through reference to the following examples which are provided by way of illustration. The Examples are set forth to aid in understanding invention but are not intended to, and should not be construed to, limit its scope in any way. The examples do not include detailed descriptions of conventional methods. Such methods are well known to those of ordinary skill in the art and are described in numerous publications.

EXAMPLE 1

Superovulation and Induction of Apoptosis in Rat Corpus Luteum

Immature (21–30 day old) female rats were superovulated by subcutaneous injection with 50 IU of PMSG (Pregnant Mare Serum Gonadotropin) and, 60 to 65 hours later, with 50 IU of HCG (Human Chorionic Gonadotropin). Seven days after the treatment with HCG, corpus luteum apoptosis was induced by subcutaneous injection with 500 µg of PGF$_{2\alpha}$ (Prostaglandin F$_{2\alpha}$). Rats were sacrificed at various times (e.g 1, 8 and 24 hours) after PGF2α treatment, and the corpora lutea were removed and placed in liquid nitrogen. Control corpus luteum tissue was obtained by sacrificing rats immediately before PGF$_{2\alpha}$ treatment.

Dispersion of Rat Ovarian Corpus Luteum Cells

Six to nine days after superovulation, rats were treated by multisite subcutaneous injection with 500 µg prostaglandin F$_{2\alpha}$. Fifteen to thirty minutes later, the ovaries were removed from the superovulated rats, placed in EBSS (Gibco) on ice, blotted dry and weighed. Connective tissue was trimmed away, and the ovaries were minced finely with a razor blade and washed twice with EBSS 2×. Collagenase solution was prepared by vortexing 6.5 mg of collagenase (Sigma, Catologue # C 5138) in 5 ml of EBSS. Minced tissue from 8 ovaries was added to 5 ml of collagenase in EBSS in a 50 ml Erlenmeyer flask and agitated gently by withdrawing several times into a Diamed pipette. The flask with minced tissue was then placed in a water bath at 37° C. for 20 minutes with gentle shaking (Position 45 on GFL incubator) under 95% air: 5% CO$_2$ Following this incubation, the flask was placed on ice, and the suspension of cells was transferred with a plastic transfer pipet onto a Nitex filter fitted with Swiss Nitex Nylon Mono filament (75 µ). The filtrate was collected into a 15 ml Falcon test tube. A second aliquot (2.5 ml) of collagenase solution (6.5 mg collagenase/5 ml EBSS) was added to the minced tissue remaining in the 50 ml Erlenmeyer flask, agitated gently using a pipette, incubated for 10 minutes and filtered as above. The two filtrates were combined and centrifuged in a clinical centrifuge (~200 g) for 5 minutes at room temperature. All but ~2 ml of the supernatant were removed with a pipet and discarded, and the sedimented cells were resuspended in the remaining 2 ml of supernatant. The cells were washed twice by adding 5 ml of MEM and centrifuging and resuspending as above. The washed cells were resuspended in 30 mls of MEM containing 10 mM glutamine in a 50 ml Erlenmeyer flask and incubated for 1 hour without shaking at 37° C. under 95% air, 5% CO$_2$. The cells were then sedimented by centrifugation as above and resuspended in MEM containing 10 mM glutamine. The concentration of dispersed cells was determined using a hemocytometer, and viability was assessed using trypan blue dye. Aliquots of 2–5×10$^5$ cells were placed in 12×75 mm test tubes and incubated without shaking for 2–5 hours at 37° C. under 95% air: % CO$_2$. The progress of apoptosis during this period was monitored by assessing the degree of DNA laddering.

Visualization of Apoptosis in Rat Corpus Luteum by DNA Laddering

The degree of apoptosis was determined by DNA laddering. Genomic DNA was isolated from dispersed corpus luteal cells or from excised corpus luteum tissue using the QIAamp DNA Blood Kit (Qiagen) according to the manufacturer's instructions. Corpus luteum tissue was excised before the induction of apoptosis by treatment with prostaglandin F$_{2\alpha}$ as well as 1 hour and 24 hours after induction of apoptosis. The isolated DNA was end-labeled by incubating 500 ng of DNA with 0.2 µCi [α-$^{32}$P]dCTP, 1 mM Tris, 0.5 mM EDTA, 3 units of Klenow enzyme, and 0.2 pM each of dATP, dGTP, and dTTP, at room temperature for 30 minutes. Unincorporated nucleotides were removed by passing the sample through a 1-ml Sephadex G-50 column according to the method described by Maniatis et al. The samples were then resolved by Tris-acetate-EDTA (1.8%) gel electrophoresis. The gel was dried for 30 minutes at room temperature under vacuum and exposed to x-ray film at –80° C. for 24 hours.

Figure 19:
FIG. 19 depicts a DNA laddering experiment in which the degree of apoptosis in superovulated rat corpus lutea was examined either 0, 1, or 24 hours after injection with $PGF_{-2\alpha}$. In the 0 hour control, the ovaries were removed without $PGF_{-2\alpha}$ injection. DNA was extracted from isolated ovaries at the indicated time points and 5 μg of DNA from each sample was labeled with [α-$^{32}$P]-dCTP using Klenow enzyme. The labeled DNA was separated on a 1.8% agarose gel and the gel was dried and exposed to film for 24 hours. DNA laddering and increased end labeling of genomic DNA are evident within one hour of $PGF_{2\alpha}$ treatment and to a greater degree by 24 hours after $PGF_{2\alpha}$ treatment.
Figure 20:
FIG. 20 is an agarose gel of genomic DNA isolated from apoptosing rat corpus luteum showing DNA laddering. Apoptosis was induced by treatment of rats with prostaglandin $F_{2\alpha}$. Corresponding control animals were treated with saline instead of prostaglandin $F_{2\alpha}$. Fifteen minutes after treatment with saline or prostaglandin $F_{2\alpha}$, corpora lutea were removed from the animals. Genomic DNA was isolated from the corpora lutea at 3 hours and 6 hours after removal of the tissue from the animals, labeled with $^{32}$P-dCTP, fractionated on an agarose gel and visualized by autoradiography. DNA laddering and increased end labeling of genomic DNA are evident 6 hours after removal of the tissue from the prostaglandin $F_{2\alpha}$-treated animals, but not at 3 hours after removal of the tissue.

Laddering of low molecular weight DNA fragments reflecting nuclease activity associated with apoptosis is not evident in control corpus luteum tissue excised before treatment with prostaglandin F$_{2\alpha}$a, but is discernible within 1 hour after induction of apoptosis and is pronounced by 24 hours after induction of apoptosis; (FIG. 19). DNA laddering reflecting apoptosis is also evident when corpora lutea are excised 15 minuets after treatment with prostaglandin F$_{2\alpha}$, and maintained for 6 hours under in vitro conditions in EBSS (Gibco) (FIG. 20). Nuclease activity associated with apoptosis is also evident from more extensive end-labelling of genomic DNA (FIGS. 20 and 19).

EXAMPLE 2

RNA Isolation

Total RNA was isolated from corpus luteum tissue removed from rats at various times after $PGF_{2\alpha}$ induction of apoptosis. Briefly, the tissue (5 g) was ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of Miracloth and centrifuged at 10,000×g at 4° C. for 30 minutes. The supernatant was then subjected to cesium chloride density gradient centrifugation at 11,200 g for 20 hours. The pelleted RNA was rinsed with 75% ethanol, resuspended in 600 µl DEPC-treated water and the RNA precipitated at −70° C. with 1.5 ml 95% ethanol and 60 µl of 3M NaOAc. Twenty µg of RNA were fractionated on a 1.2% denaturing formaldehyde agarose gel and transferred to a nylon membrane. Randomly primed 32P-dCTP-labeled full length eIF-5A cDNA (SEQ ID NO:1) or partial length DHS cDNA (SEQ ID NO. 6) were used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to X-ray film overnight at −70° C.

Genomic DNA Isolation and Laddering

Genomic DNA was isolated from extracted corpus luteum tissue or dispersed corpus luteal cells using the QIAamp DNA Blood Kit (Qiagen) according to the manufacturer's instructions. The DNA was end-labeled by incubating 500 ng of DNA with 0.2 µCi [α-$^{32}$P]dCTP, 1 mM Tris, 0.5 mM EDTA, 3 units of Klenow enzyme, and 0.2 pM each of dATP, dGTP, and dTTP, at room temperature for 30 minutes. Unincorporated nucleotides were removed by passing the sample through a 1-ml Sephadex G-50 column according to the method described by Maniatis et al. The samples were then resolved by Tris-acetate-EDTA (2%) gel electrophoresis. The gel was dried for 30 minutes at room temperature under vacuum and exposed to x-ray film at −80° C. for 24 hours.

Plasmid DNA Isolation, DNA Sequencing

The alkaline lysis method described by Sambrook et al., (Supra) was used to isolate plasmid DNA. The full length positive cDNA clone was sequenced using the dideoxy sequencing method. Sanger, et al., Proc. Natl. Acad. Sci. USA, 74:5463–5467. The open reading frame was compiled and analyzed using BLAST search (GenBank, Bethesda, Md.) and sequence alignment was achieved using a BCM Search Launcher: Multiple Sequence Alignments Pattern-Induced Multiple Alignment Method (See F. Corpet, Nuc. Acids Res., 16:10881–10890, (1987). Sequences and sequence alignments are shown in FIGS. 3 through 11, 15 and 18.

Northern Blot Hybridizations of Rat Corpus Luteum RNA

Twenty µg of total RNA isolated from rat corpus luteum at various stages of apoptosis were separated on 1% denatured formaldehyde agarose gels and immobilized on nylon membranes. The full length rat apoptosis-induced eIF-5A cDNA labeled with $^{32}$P-dCTP using a random primer kit (Boereinger) was used to probe the membranes (7×10$^7$ cpm). Alternatively, full length rat apoptosis-induced DHS cDNA labeled with $^{32}$p-dCTP using a random primer kit (Boreinger) was used to probe the membranes (7×10$^7$ cpm). The membranes were washed once with 1×SSC, 0.1% SDS at room temperature and three times with 0.2×SSC, 0.1% SDS at 65° C. The membranes were dried and exposed to X-ray film overnight at −70° C. The results are shown in FIGS. 14 and 17. As can be seen, eIF-5A and DHS are both upregulated in apoptosing corpus luteum tissue.

Example 3

Generation of an Apoptosing Rat Corpus Luteum RT-PCR Product Using Primers Based on Yeast, Fungal and Human eIF-5A sequences A partial-length apoptosis-induced eIF-5A sequence (SEQ ID NO. 111) corresponding to the 3' end of the gene was generated from apoptosing rat corpus luteum RNA template by RT-PCR using a pair of oligonucleotide primers designed from yeast, fungal and human eIF-5A sequences. The upstream primer used to isolate the 3'end of the rat eIF-5A gene is a 20 nucleotide degenerate primer: 5'TCSAARACHGGNAAGCAYGG 3' (SEQ ID NO. 9), wherein S is selected from C and G; R is selected from A and G; H is selected from A, T, and C; Y is selected from C and T; and N is any nucleic acid.

The downstream primer used to isolate the 3'end of the rat eIF-5A gene contains 42 nucleotides: GCGAAGCTTC-CATGGCTCGAGTTTTTTTTTTTTTTTTT 3' (SEQ ID NO. 10). A reverse transcriptase-polymerase chain reaction (RT-PCR) was carried out as follows: Using 5 µg of the downstream primer, a first strand of cDNA was synthesized.

Reaction Components:

| | |
|---|---|
| RNA (5 µg) | 10.5 µl |
| Poly(T) primer(5 µg) | 1.0 µl |
| 5X buffer | 4.0 µl |
| dNTP(10 mM) | 2.0 µl |
| RNase Inhibitor(4 U/µl) | 0.5 µl |
| MMLV(20 U/µl) | 2.0 µl |
| Reaction volume | 20.0 µl |

Reaction Parameters:
37° C. for 1 hour

The first strand was then used as a template in a RT-PCR using both the upstream and downstream primers.

Reaction Components:

| | |
|---|---|
| cDNA | 2.00 µl |
| H$_2$O | 32.75 µl |
| 10X buffer | 5.00 µl |
| MgCl$_2$(15 mM) | 5.00 µl |
| dNTP(10 mM) | 1.00 µl |
| Primer 1 and 2(15 µM each) | 2.00 µl each |
| Tsg polymerase | 0.25 µl |
| Reaction volume | 50.00 µl |

Reaction Parameters:
94° C. for 5 min 94° C. for 1 min, 48° C. for 1 min. 72° C. for 2 min, for 45 cycles 72° C. for 15 min.

A partial-length apoptosis-induced eIF-5A sequence (SEQ ID NO. 15) corresponding to the 5' end of the gene and overlapping with the 3' end was generated from apoptosing rat corpus luteum RNA template by RT-PCR. The 5' primer is a 24-mer having the sequence, 5'CAGGTCTAGAGTTG-GAATCGAAGC 3' (SEQ ID NO. 13), that was designed from human eIF-5A sequences. The 3' primer is a 30 mer having the sequence, 5' ATATCTCGAGCCTTGATTG-CAACAGCTGCC 3' (SEQ ID NO. 14) that was designed according to the 3' end RT-PCR fragment. A reverse transcriptase-polymerase chain reaction (RT-PCR) was carried out as follows:

Using 5 µg of the downstream primer, a first strand of cDNA was synthesized.

Reaction Components:

| | |
|---|---|
| RNA(5 μg) | 10.5 μl |
| Poly(T) primer(5 μg) | 1.0 μl |
| 5X buffer | 4.0 μl |
| dNTP(10 mM) | 2.0 μl |
| RNase Inhibitor(4 U/μl) | 0.5 μl |
| MMLV (20 U/μl) | 2.0 μl |
| Reaction volume | 20.0 μl |

Reaction Parameters:
37° C. for 1 hour
The first strand was then used as a template in a RT-PCR using both the upstream and downstream primers.
Reaction Components:

| | |
|---|---|
| cDNA | 2.00 μl |
| H₂O | 32.75 μl |
| 10X buffer | 5.00 μl |
| MgCl₂(15 mM) | 5.00 μl |
| dNTP(10 mM) | 1.00 μl |
| Primer 1 and 2(15 μM each) | 2.00 μl each |
| Tsg polymerase | 0.25 μl |
| Reaction volume | 50.00 μl |

Reaction Parameters:
94° C. for 5 min 94° C. for 1 min, 48° C. for 1 min, 72° C. for 2 min, for 45 cycles 72° C. for 15 min.

The nucleotide sequence (SEQ ID NO. 1) for the full length cDNA of the rat apoptosis-induced corpus luteum eIF-5A gene obtained by RT-PCR and the corresponding derived amino acid sequence (SEQ ID NO.9) are depicted in FIG. 5.

Generation of an Apoptosing Rat Corpus Luteum RT-PCR Product Using Primers Based on a Human DHS Sequence A partial-length apoptosis-induced DHS sequence (SEQ ID NO. 6) corresponding to the 3' end of the gene was generated from apoptosing rat corpus luteum RNA template by RT-PCR using a pair of oligonucleotide primers designed from a human DHS sequence. The 5' primer is a 20-mer having the sequence, 5' GTCTGTGTATTATTGGGCCC 3' (SEQ ID NO. 17); the 3' primer is a 42-mer having the sequence, 5'GCGAAGCTTCCATGGCTC-GAGTTTTTTTTTTTTTTTTTTT 3' (SEQ ID NO. 18). A reverse transcriptase-polymerase chain reaction (RT-PCR) was carried out as follows:
Using 5 μg of the downstream primer, a first strand of cDNA was synthesized.
Reaction Components:

| | |
|---|---|
| RNA(5 μg) | 10.5 μl |
| Poly(T) primer(5 μg) | 1.0 μl |
| 5X buffer | 4.0 μl |
| dNTP(10 mM) | 2.0 μl |
| RNase Inhibitor(4 U/μl) | 0.5 μl |
| MMLV(20 U/μl) | 2.0 μl |
| Reaction volume | 20.0 μl |

Reaction Parameters:
37° C. for 1 hour
The first strand was then used as a template in a RT-PCR using both the upstream and downstream primers.
Reaction Components:

| | |
|---|---|
| cDNA | 2.00 μl |
| H₂O | 32.75 μl |
| 10X buffer | 5.00 μl |
| MgCl₂(15 mM) | 5.00 μl |
| dNTP(10 mM) | 1.00 μl |
| Primer 1 and 2(15 μM each) | 2.00 μl each |
| Tsg polymerase | 0.25 μl |
| Reaction volume | 50.00 μl |

Reaction Parameters:
94° C. for 5 min 94° C. for 1 min. 48° C. for 1 min, 72° C. for 2 min, for 5 cycles 72° C. for 15 min.

The nucleotide sequence (SEQ ID NO. 6) for the partial length cDNA of the rat apoptosis-induced corpus luteum DHS gene obtained by RT-PCR and the corresponding derived amino acid sequence (SEQ ID NO.7) are depicted in FIG. 15.

EXAMPLE 4
Isolation of Genomic DNA and Southern Analysis

Genomic DNA for southern blotting was isolated from excised rat ovaries. Approximately 100 mg of ovary tissue was divided into small pieces and placed into a 15 ml tube. The tissue was washed twice with 1 ml of PBS by gently shaking the tissue suspension and then removing the PBS using a pipette. The tissue was resuspended in 2.06 ml of DNA-buffer (0.2 M Tris-HCl pH 8.0 and 0.1 mM EDTA) and 240 μl of 10% SDS and 100 μl of proteinase K (Boehringer Manheim; 10 mg/ml) was added. The tissue was placed in a shaking water bath at 45° C. overnight. The following day another 100 μl of proteinase K (10 mg/ml) was added and the tissue suspension was incubated in a waterbath at 45° C. for an additional 4 hours. After the incubation the tissue suspension was extracted once with an equal volume of phenol:chloroform:iso-amyl alcohol (25:24:1) and once with an equal volume of chloroform:iso-amyl alcohol (24:1). Following the extractions ¹⁄₁₀th volume of 3 M sodium acetate (pH 5.2) and 2 volumes of ethanol were added. A glass pipette sealed and formed into a hook using a Bunsen burner was used to pull the DNA threads out of solution and to transfer the DNA into a clean microcentrifuge tube. The DNA was washed once in 70% ethanol and air-dried for 10 minutes. The DNA pellet was dissolved in 500 μl of 10 mM Tris-HCl (pH 8.0), 10 μl of RNase A (10 mg/ml) was added, and the DNA was incubated for 1 hour at 37° C. The DNA was extracted once with phenol:chloroform:iso-amyl alcohol (25:24:1) and the DNA was precipitated by adding ¹⁄₁₀th volume of 3 M sodium acetate (pH 5.2) and 2 volumes of ethanol. The DNA was pelleted by centrifugation for 10 minutes at 13,000×g at 4° C. The DNA pellet was washed once in 70% ethanol and dissolved in 200 μl 10 mM Tris-HCl (pH 8.0) by rotating the DNA at 4° C. overnight.

Figure 21:
FIG. 21 is a Southern blot of rat genomic DNA probed with $^{32}$P-dCTP-labeled partial-length rat corpus luteum apoptosis-induced DHS cDNA. The genomic DNA was cut with EcoRV, a restriction enzyme which does not cut the partial-length cDNA used as a probe. Two restriction fragments are evident indicating that there are two copies of the gene or that the gene contains an intron with an EcoRV site.

For Southern blot analysis, genomic DNA isolated from rat ovaries was digested with various restriction enzymes which either do not cut in the endogenous gene or cut only once. To achieve this, 10 μg genomic DNA, 20 μl 10× reaction buffer and 100 U restriction enzyme were reacted for five to six hours in a total reaction volume of 200 μl. Digested DNA was loaded onto a 0.7% agarose gel and subjected to electrophoresis for 6 hours at 40 volts or overnight at 15 volts. After electrophoresis, the gel was depurinated for 10 minutes in 0.2 N HCl followed by two 15 minute washes in denaturing solution (0.5 M NaOH, 1.5 M NaCl) and two 15 minute washes in neutralizing buffer (1.5 M NaCl, 0.5 M Tris-HCl pH 7.4). The DNA was transferred to a nylon membrane, and the membrane was prehybridized in hybridization solution (40% formamide, 6×SSC, 5× Denhart's, solution (1× Denhart's solution is 0.02% Ficoll, 0.02% PVP, and 0.02% BSA), 0.5% SDS, and 1.5 mg of denatured salmon sperm DNA)). A 700 bp PCR fragment of the 3' UTR of rat eIF-5A cDNA (650 bp of 3' UTR and 50 bp of coding) was labeled with $[\alpha\text{-}^{32}P]$-dCTP by random priming and added to the membrane at $1\times10^6$ cpm/ml. Similarly, a 606 bp PCR fragment of the rat DHS cDNA (450 bp coding and 156 bp 3' UTR) was random prime labeled with $[\alpha\text{-}^{32}P]$-dCTP and added at $1\times10^6$ cpm/ml to a second identical membrane. The blots were hybridized overnight at 42° C. and then washed twice with 2×SSC and 0.1% SDS at 42° C. and twice with 1×SSC and 0.1% SDS at 42° C. The blots were then exposed to film for 3–10 days. The results are shown in FIGS. 13 and 21.

EXAMPLE 5
Inhibition of Apoptosis

Apoptosis is inhibited when corpus luteal cells are treated with spermidine, a compound that inhibits the activation of eIF-5A by DHS. Six to nine days after superovulation, rats were treated with 500 ug of prostaglandin F 2α subcutaneously. Control rats were treated with an equivalent volume of saline solution. Fifteen to thirty minutes later, the ovaries were removed from 4 to 8 superovulated rats, placed in EBSS Gibco) on ice, blotted dry and weighed. Connective tissue was trimmed away, and the ovaries were minced finely with a razor blade and washed twice with EBSS 2×. Collagenase solution was prepared by vortexing 6.5 mg of collagenase (Sigma) in 5 ml of EBSS. Minced tissue from 8 ovaries was added to 5 ml of collagenase in EBSS in a 50 ml Erlenmeyer flask and agitated gently by withdrawing several times into a Diamed pipette. The flask with minced tissue was then placed in a water bath at 57° C. for 20 minutes with gentle shaking under 95% air: 5% $CO_2$. Following this incubation, the flask was placed on ice, and the suspension was transferred to a Nitex filter fitted with Swiss Nitex Nylon Monofilament (75 $\mu$) using a plastic transfer pipet. The filtrate was collected into a 15 ml Falcon test tube. An aliquot (2.5 ml) of collagenase solution was added to the minced tissue retained in the filter, and the suspension was transferred to a 50 ml Erlenmeyer flask and agitated gently using a pipette, incubated and filtered as above The two filtrates were combined, mixed with 27.5 ml of MEM (Sigma) and 1.5 ml of 10 mM glutamine and filtered again through Nitex. The dispersed cells in the filtrate were sedimented in Falcon tubes by centrifugation using a clinical centrifuge for 5 minutes. All but 2 mls of the supernatant was removed with a pipette, and the sedimented cells were gently resuspended in the remaining 2 ml supernatant. The cells were washed twice in 5 mls MEM by centrifugation and resuspension as above and finally resuspended in 30 mls of MEM with glutamine and with or without 10 mM spermidine (Amersham Life Science), and incubated for 1 hour without shaking at 37 C under 95% air: 5% $CO_2$ The cells were then sedimented by centrifugation as above and resuspended in MEM with glutamine. The concentration of dispersed cells was determined using a hemocytometer, and viability was assessed using trypan blue dye. Aliquots of 2 to $5\times10^5$ cells were placed in 12×75 mm test tubes and incubated without shaking for 5 hours at 37 C with or without 1 mM spermidine under 95% air: 5% $CO_2$. Following the incubation, the cells were sedimented by centrifugation, the supernatant was removed, and the pelleted cells were frozen at −80° C. prior to DNA isolation.

The degree of apoptosis in each sample was determined by DNA laddering and degree of end labelling, both of which reflect nuclease activity. In brief, DNA was isolated from the ovaries, labeled with $[\alpha\text{-}^{32}P]$-dCTP using Klenow enzyme, separated on a 1.8% agarose gel, and exposed to film. The sample from control rats injected with saline and incubated without spermidine in both incubation steps showed no evidence of laddering or increased end-labeling (FIG. 1, lane 1). The sample from rats injected with prostaglandin $F_{2\alpha}$ and incubated with 10 mM spermidine for the 1 hour incubation and without spermidine in the 5 hour incubation (FIG. 1, lane 2) showed more end labeling reflecting apoptosis-associated nuclease activity than the sample that was additionally treated with 1 mM spermidine during the 5 hour incubation (FIG. 1 lane 3).

EXAMPLE 6
In vivo Inhibition of Apoptosis by Spermidine

Apoptosis of the corpus luteum, as determined by DNA laddering and DNA end labelling, is inhibited when superovulated rats are injected with spermidine prior to exposure to prostaglandin $F_{2\alpha}$. Six days after superovulation, rats received three subcutaneous injections of 0.333 mg of spermidine/100 g rat body weight (for a total dose of 1 mg/100 g rat body weight) 24 hours, 12 hours, and 2 hours prior to injection with 500 $\mu$g of prostaglandin $F_{2\alpha}$, subcutaneously. Control rats received either no injections (FIG. 2, lane 1), were injected three times with spermidine but received no prostaglandin $F_{2\alpha}$. (FIG. 2, lane 2) or were injected three times with an equivalent volume of saline prior to an injection with prostaglandin $F_{2\alpha}$ (FIG. 2, lane 3l). The rats were sacrificed and the ovaries removed either one hour and thirty five minutes or three hours and forty-five minutes after injection with prostaglandin $F_{2\alpha}$. The degree of apoptosis was determined by DNA end-labeling. In brief, DNA was isolated from the ovaries, labeled with $[\alpha\text{-}^{32}P]$-dCTP using Klenow enzyme, separated on a 1.8% agarose gel, and exposed to film. The DNA isolated from control rats which received no injections (FIG. 2, lane 1) and the DNA from rats treated with saline and prostaglandin Fα (FIG. 2, lane 3) showed a much higher degree of end-labeling reflecting apoptosis-related nuclease activity than DNA from rats treated with either spermidine alone or spermidine followed by prostaglandin $F_{2\alpha}$ (FIG. 2, lanes 2, 4, 5, 6, 7). In particular, endogenous treatment of rats with spermidine inhibits apoptosis whether it is initiated in situ without exogenous prostaglandin $F_{2\alpha}$ (FIG. 2, lanes 1 and 2) or by treatment with exogenous prostaglandin $F_{2\alpha}$ (FIG. 2, lanes 3 and 4).

EXAMPLE 7
Design of Antisense Oligonucleotides

Mfold version 3.1 by Zuker and Turner was used to predict the secondary structure of the mRNA of the full-length rat eIF-5A. Oligonucleotides against accessible regions of 14 base pairs or longer that were not base-paired and that existed at all three of the lowest energy conformations based on a folding temperature of 37° C. were designed (Antisense Oligo 1 and Antisense Oligo 2). An oligo spanning the translation start site was also designed, although it was not predicted to be accessible (Antisense Oligo 3).

Antisense Oligo I: bp 618 to 635 of full-length sequence
(18 bp) 5' TTG AAG GGG TGA GGA AAA 3
Antisense Oligo 2: bp 845 to 859 of full-length sequence
(15 bp) 5' TTG AGT GGG ATA AAG 3'
Antisense Oligo 3: spanning ATG start (−5 to +13)
(18 bp) 5' AAT CAT CTG CCA TTT TAA 3'

For additional description of mfold version 3.1 software, see, e.g., Zuker M., et al. "Algorithms and Thermodynamics for RNA Secondary Structure Prediction: A Practical Guide In RNA Biochemistry and Biotechnology, 11–43, J. Barciszewski and B. F. C. Clark, eds., NATO ASI Series, Kluwer Academic Publishers (1999); Mathews DH, et al., "Expanded Sequence Dependence of Thermodynamic Parameters Improves Prediction of RNA Secondary Structure," J. Mol. Biol. 288: 91140 (1999).

We claim:

1. A method for inhibiting or delaying apoptosis in vitro in a cell or cells of a mammalian corpus luteum, comprising administering to said cell or cells an agent that is capable of inhibiting an apoptosis-induced DHS catalyzed chemical reaction, wherein the agent is selected from the group consisting of spermidine, 1,3-Diamino-propane, 1,4-Diamino-butane (putrescine), 1,7-Diamino-heptane, and 1,8-Diamino-octane;

and wherein said inhibiting apoptosis-induced DHS catalyzed chemical reaction reduces levels of activated apoptosis-induced eIF-5A or inhibits activation of apoptosis-induced eIF-5A; and wherein said reduction of apoptosis-induced eIF-5A or inhibition of activation of apoptosis-induced eIF-5A inhibits or delays apoptosis.

2. A method for inhibiting or suppressing activation of apoptosis-induced eIF-5A in a cell or cells of a mammalian corpus luteum comprising administering an agent to the cell or cells that is capable of inhibiting DHS catalyzed chemical reactions, wherein the agent is selected from the group consisting of exogenous spermidine, 1,3-Diamino-propane, 1,4-Diamino-butane (putrescine), 1,7-Diamino-heptane, and 1,8-Diamino-octane, and wherein the agent is not administered at toxic levels; and wherein the inhibiting apoptosis-induced DHS catalyzed chemical reactions inhibit or reduce an apoptosis cascade, said cascade comprising transferring a 4-aminobutyl residue from an endogenous spermidine to a ε-amino group of a conserved lysine on an inactive apoptosis-induced eIF-5A, said transferring converting the lysine to a deoxyhypusine, and wherein a deoxyhypusine hydroxylase converts the deoxyhypusine to hypusine, and wherein inhibition or reduction of said apoptosis cascade reduces an amount of activated apoptosis-induced eIF-5 or inhibits activation of apoptosis-induced eIF-5A in the cell.

3. A method for inhibiting or delaying apoptosis in a cell or cells of a mammalian corpus luteum, comprising administering to said cell or cells an agent that is capable of inhibiting an apoptosis-induced DHS catalyzed chemical reaction, wherein the agent is spermidine, 1,3-Diamino-propane, 1,4-Diamino-butane (putrescine), 1,7-Diamino-heptane, and 1,8-Diamino-octane, and wherein the agent is not administered at toxic levels, and wherein said inhibiting apoptosis-induced DHS catalyzed chemical reaction reduces levels of activated apoptosis-induced eIF-5A or inhibits activation of apoptosis-induced eIF-5A, and wherein said reduction of apoptosis-induced eIF-5A or inhibition of activation of apoptosis-induced eIF-5A inhibits or delays apoptosis in said cell.

4. A method for inhibiting or delaying apoptosis in a cell or cells of a mammalian corpus luteum, comprising administering to said cell spermidine, wherein the spermidine inhibits an apoptosis-induced DHS catalyzed chemical reaction to reduce levels of activated apoptosis-induced eIF-5A or to inhibit activation of apoptosis-induced eIF-5A; and wherein said reduction of apoptosis-induced eIF-5A or inhibition of activation of apoptosis-induced eIF-5A inhibits or delays apoptosis.

* * * * *

SEQUENCE LISTING

<160> NUMBER OF SEQ ID NOS: 21

<210> SEQ ID NO 1
<211> LENGTH: 1139
<212> TYPE: DNA
<213> ORGANISM: Rodent
<220> FEATURE:
<221> NAME/KEY: CDS
<222> LOCATION: (33)...(497)

<400> SEQUENCE: 1

```
caggtctaga gttggaatcg aagcctctta aa atg gca gat gat ttg gac ttc        53
                                   Met Ala Asp Asp Leu Asp Phe
                                    1               5 gag aca gga gat gca ggg gcc tca gcc acc ttc cca atg cag tgc tca       101
Glu Thr Gly Asp Ala Gly Ala Ser Ala Thr Phe Pro Met Gln Cys Ser
            10                  15                  20 gca tta cgt aag aat ggt ttt gtg gtg ctc aag ggc cgg cca tgt aag       149
Ala Leu Arg Lys Asn Gly Phe Val Val Leu Lys Gly Arg Pro Cys Lys
    25                  30                  35 atc gtc gag atg tct act tcg aag act ggc aag cat ggc cat gcc aag       197
Ile Val Glu Met Ser Thr Ser Lys Thr Gly Lys His Gly His Ala Lys
 40                  45                  50                  55 gtc cat ctg gtt ggt att gat att ttt act ggg aag aaa tat gaa gat       245
Val His Leu Val Gly Ile Asp Ile Phe Thr Gly Lys Lys Tyr Glu Asp
                60                  65                  70 atc tgc ccg tcg act cat aac atg gat gtc ccc aac atc aaa agg aat       293
Ile Cys Pro Ser Thr His Asn Met Asp Val Pro Asn Ile Lys Arg Asn
            75                  80                  85 gat ttc cag ctg att ggc atc cag gat ggg tac cta tcc ctg ctc cag       341
Asp Phe Gln Leu Ile Gly Ile Gln Asp Gly Tyr Leu Ser Leu Leu Gln
         90                  95                 100 gac agt ggg gag gta cga gag gac ctt cgt ctg cct gag gga gac ctt       389
Asp Ser Gly Glu Val Arg Glu Asp Leu Arg Leu Pro Glu Gly Asp Leu
105                 110                 115 ggc aag gag att gag cag aag tat gac tgt gga gaa gag atc ctg atc       437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gcc       485
Thr Val Leu Ser Ala Met Thr Glu Glu Ala Ala Val Ala Ile Lys Ala
                140                 145                 150 atg gca aaa taa ctggcttcca gggtggcggt ggtggcagca gtgatccatg           537
Met Ala Lys * agcctacaga ggcccctccc ccagctctgg ctgggccctt ggctggactc ctatccaatt    597
tatttgacgt tttattttgg ttttcctcac cccttcaaac tgtcggggag accctgccct    657
tcacctagct cccttggcca ggcatgaggg agccatggcc ttggtgaagc tacctgcctc    717
ttctctcgca gccctgatgg gggaaaggga gtgggtactg cctgtggttt aggttcccct    777 ctccctttttt cttttttaatt caatttggaa tcagaaagct gtggattctg gcaaatggtc  837
ttgtgtcctt tatcccactc aaacccatct ggtcccctgt tctccatagt ccttcacccc    897
caagcaccac tgacagactg gggaccagcc cccttccctg cctgtgtctc ttcccaaacc    957
cctctatagg ggtgacaaga agaggagggg gggagggac acgatccctc ctcaggcatc    1017
```

```
tgggaaggcc ttgcccccat gggctttacc ctttcctgtg ggctttctcc ctgacacatt    1077
tgttaaaaat caaacctgaa taaaactaca agtttaatat gaaaaaaaaa aaaaaaaaaa    1137
aa                                                                  1139
```

<210> SEQ ID NO 2
<211> LENGTH: 154
<212> TYPE: PRT
<213> ORGANISM: Rodent

<400> SEQUENCE: 2

```
Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150
```

<210> SEQ ID NO 3
<211> LENGTH: 462
<212> TYPE: DNA
<213> ORGANISM: Rodent

<400> SEQUENCE: 3

```
atggcagatg acttggactt cgagacagga gatgcagggg cctcagccac cttcccaatg     60
cagtgctcag cattacgtaa gaatggcttt gtggtgctca aaggccggcc atgtaagatc    120
gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga agagatcc tgatcacggt gctgtctgcc    420
atgacagagg aggcagctgt tgcaatcaag gccatggcaa aa                      462
```

<210> SEQ ID NO 4
<211> LENGTH: 462
<212> TYPE: DNA
<213> ORGANISM: Rodent
<220> FEATURE:
<221> NAME/KEY: misc_feature
<222> LOCATION: (1)...(462)
<223> OTHER INFORMATION: n = A,T,C or G

<400> SEQUENCE: 4

```
atggcagacg aaattgattt cactactgga gatgccgggg cttccagcac ttaccctatg      60
cagtgctcgg ccttgcgcaa aaacggcttc gtggtgctca aggacgacc atgcaaaata     120 gtggagatgt caacttccaa aactggaaag catggtcatg ccaaggttca ccttgttgga    180
attgatattt tcacgggcaa aaaatatgaa gatatttgtc cttctactca caacatggat    240
gttccaaata ttaagagaaa tgattatcaa ctgatatgca ttcaagatgg ttacctttcc    300
ctgctgacag aaactggtga agttcgtgag gatcttaaac tgccagaagg tgaactaggc    360
aaagaaatag agggaaaata caatgcaggt gaagatgtac aggtgtctgt catgtgtgca    420
atgagtgaag aatatgctgt agccataaaa ccctnngcaa at                      462

<210> SEQ ID NO 5
<211> LENGTH: 462
<212> TYPE: DNA
<213> ORGANISM: Rodent

<400> SEQUENCE: 5
atggcagatg atttggactt cgagacagga gatgcagggg cctcagccac cttcccaatg    60
cagtgctcag cattacgtaa gaatggtttt gtggtgctca aggccggcc atgtaagatc    120 gtcgagatgt ctacttcgaa gactggcaag catggccatg ccaaggtcca tctggttggc    180
attgacattt ttactgggaa gaaatatgaa gatatctgcc cgtcgactca taatatggat    240
gtccccaaca tcaaacggaa tgacttccag ctgattggca tccaggatgg gtacctatcc    300
ctgctccagg acagtgggga ggtacgagag gaccttcgtc tgcctgaagg agaccttggc    360
aaggagattg agcagaagta tgactgtgga gaagagatcc tgatcacagt gctgtctgcc    420
atgacagagg aggcagctgt tgcaatcaag gccatggcaa aa                      462

<210> SEQ ID NO 6
<211> LENGTH: 606
<212> TYPE: DNA
<213> ORGANISM: Rodent
<220> FEATURE:
<221> NAME/KEY: CDS
<222> LOCATION: (1)...(456)

<400> SEQUENCE: 6 gct gtg tat tat tgg gcc cat aag aac cac ata cct gtg ctg agt cct      48
Ala Val Tyr Tyr Trp Ala His Lys Asn His Ile Pro Val Leu Ser Pro
 1               5                  10                  15 gca ctc aca gac ggc tca ctg ggt gac atg atc ttt ttc cat tcc tat      96
Ala Leu Thr Asp Gly Ser Leu Gly Asp Met Ile Phe Phe His Ser Tyr
             20                  25                  30 aaa aac cca ggc ttg gtc ctg gac atc gtt gaa gac ctg cgg ctc atc     144
Lys Asn Pro Gly Leu Val Leu Asp Ile Val Glu Asp Leu Arg Leu Ile
         35                  40                  45 aac atg cag gcc att ttc gcc aag cgc act ggg atg atc atc ctg ggt     192
Asn Met Gln Ala Ile Phe Ala Lys Arg Thr Gly Met Ile Ile Leu Gly
     50                  55                  60 gga ggc gtg gtc aag cac cac atc gcc aat gct aac ctc atg cgg aat     240
Gly Gly Val Val Lys His His Ile Ala Asn Ala Asn Leu Met Arg Asn
 65                  70                  75                  80 gga gct gac tac gct gtt tat atc aac aca gcc cag gag ttt gat ggc     288
Gly Ala Asp Tyr Ala Val Tyr Ile Asn Thr Ala Gln Glu Phe Asp Gly
                 85                  90                  95 tca gac tca gga gcc cgg cca gat gag gct gtc tcc tgg ggc aag atc     336
Ser Asp Ser Gly Ala Arg Pro Asp Glu Ala Val Ser Trp Gly Lys Ile
            100                 105                 110
```

```
cgg atg gat gca cag cca gta aag gtc tat gct gat gca tct ctg gtt      384
Arg Met Asp Ala Gln Pro Val Lys Val Tyr Ala Asp Ala Ser Leu Val
            115                 120                 125 ttc ccc ttg ctg gtg gct gag aca ttc gcc caa aag gca gat gcc ttc      432
Phe Pro Leu Leu Val Ala Glu Thr Phe Ala Gln Lys Ala Asp Ala Phe
        130                 135                 140 aga gct gag aag aat gag gac tga gcagatgggt aaagacggag gcttctgcca     486
Arg Ala Glu Lys Asn Glu Asp  *
145                 150 cacctttatt tattatttgc ataccaaccc ctcctgggcc ctctccttgg tcagcagcat    546
cttgagaata aatggccttt tgttggtttt ctgtaaaaaa aggactttaa aaaaaaaaaa    606

<210> SEQ ID NO 7
<211> LENGTH: 151
<212> TYPE: PRT
<213> ORGANISM: Rodent

<400> SEQUENCE: 7

Ala Val Tyr Tyr Trp Ala His Lys Asn His Ile Pro Val Leu Ser Pro
1               5                   10                  15

Ala Leu Thr Asp Gly Ser Leu Gly Asp Met Ile Phe Phe His Ser Tyr
            20                  25                  30

Lys Asn Pro Gly Leu Val Leu Asp Ile Val Glu Asp Leu Arg Leu Ile
        35                  40                  45

Asn Met Gln Ala Ile Phe Ala Lys Arg Thr Gly Met Ile Ile Leu Gly
    50                  55                  60

Gly Gly Val Val Lys His His Ile Ala Asn Ala Asn Leu Met Arg Asn
65                  70                  75                  80

Gly Ala Asp Tyr Ala Val Tyr Ile Asn Thr Ala Gln Glu Phe Asp Gly
                85                  90                  95

Ser Asp Ser Gly Ala Arg Pro Asp Glu Ala Val Ser Trp Gly Lys Ile
            100                 105                 110

Arg Met Asp Ala Gln Pro Val Lys Val Tyr Ala Asp Ala Ser Leu Val
        115                 120                 125

Phe Pro Leu Leu Val Ala Glu Thr Phe Ala Gln Lys Ala Asp Ala Phe
    130                 135                 140

Arg Ala Glu Lys Asn Glu Asp
145                 150

<210> SEQ ID NO 8
<211> LENGTH: 453
<212> TYPE: DNA
<213> ORGANISM: Rodent

<400> SEQUENCE: 8
tccgtgtatt actgggccca gaagaaccac atccctgtgt ttagtcccgc acttacagac     60
ggctcgctgg gcgacatgat cttcttccat tcctacaaga cccgggcct ggtcctggac     120 atcgttgagg acctgaggct catcaacaca caggccatct tgccaagtg cactgggatg     180 atcattctgg gcgggggcgt ggtcaagcac acattgcca atgccaacct catgcggaac     240
ggggccgact acgctgttta catcaacaca gcccaggagt tgatggctc tgactcaggt     300 gcccgaccag acgaggctgt ctcctgggc aagatccggg tggatgcaca gcccgtcaag     360
gtctatgctg acgcctccct ggtcttcccc ctgcttgtgg ctgaaacctt tgcccagaag     420
atggatgcct tcatgcatga aagaacgag gac                                  453
```

```
<210> SEQ ID NO 9
<211> LENGTH: 20
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(20)
<223> OTHER INFORMATION: n = A,T,C or G

<400> SEQUENCE: 9
tcsaarachg gnaagcaygg                                                      20

<210> SEQ ID NO 10
<211> LENGTH: 42
<212> TYPE: DNA
<213> ORGANISM: Rodent
<220> FEATURE:
<223> OTHER INFORMATION: Primer

<400> SEQUENCE: 10
gcgaagcttc catggctcga gttttttttt tttttttttt tt                             42

<210> SEQ ID NO 11
<211> LENGTH: 972
<212> TYPE: DNA
<213> ORGANISM: Rodent
<220> FEATURE:
<221> NAME/KEY: CDS
<222> LOCATION: (1)...(330)

<400> SEQUENCE: 11 tcg aag acc ggt aag cac ggc cat gcc aag gtc cat ctg gtt ggt att            48
Ser Lys Thr Gly Lys His Gly His Ala Lys Val His Leu Val Gly Ile
 1               5                  10                  15 gat att ttt act ggg aag aaa tat gaa gat atc tgc ccg tcg act cat            96
Asp Ile Phe Thr Gly Lys Lys Tyr Glu Asp Ile Cys Pro Ser Thr His
             20                  25                  30 aac atg gat gtc ccc aac atc aaa agg aat gat ttc cag ctg att ggc           144
Asn Met Asp Val Pro Asn Ile Lys Arg Asn Asp Phe Gln Leu Ile Gly
         35                  40                  45 atc cag gat ggg tac cta tcc ctg ctc cag gac agt ggg gag gta cga           192
Ile Gln Asp Gly Tyr Leu Ser Leu Leu Gln Asp Ser Gly Glu Val Arg
     50                  55                  60 gag gac ctt cgt ctg cct gag gga gac ctt ggc aag gag att gag cag           240
Glu Asp Leu Arg Leu Pro Glu Gly Asp Leu Gly Lys Glu Ile Glu Gln
 65                  70                  75                  80 aag tat gac tgt gga gaa gag atc ctg atc aca gtg ctg tcc gcc atg           288
Lys Tyr Asp Cys Gly Glu Glu Ile Leu Ile Thr Val Leu Ser Ala Met
                 85                  90                  95 aca gag gag gca gct gtt gca atc aag gcc atg gca aaa taa                   330
Thr Glu Glu Ala Ala Val Ala Ile Lys Ala Met Ala Lys *
                100                 105 ctggcttcca gggtggcggt ggtggcagca gtgatccatg agcctacaga ggcccctccc         390
ccagctctgg ctgggccctt ggctggactc tatccaatt  tatttgacgt tttattttgg         450
ttttcctcac cccttcaaac tgtcgggag  accctgccct tcacctagct cccttggcca         510
ggcatgaggg agccatggcc ttggtgaagc tacctgcctc ttctctcgca gccctgatgg         570
gggaaaggga gtgggtactg cctgtggttt aggttcccct ctcccttttt cttttttaatt        630 caatttggaa tcagaaagct gtggattctg gcaaatggtc ttgtgtcctt tatcccactc         690
aaacccatct ggtcccctgt tctccatagt ccttcacccc caagcaccac tgacagactg         750
```

```
gggaccagcc cccttccctg cctgtgtctc ttcccaaacc cctctatagg ggtgacaaga      810
agaggagggg gggagggggac acgatccctc ctcaggcatc tgggaaggcc ttgcccccat      870
gggctttacc ctttcctgtg ggctttctcc ctgacacatt tgttaaaaat caaacctgaa      930
taaaactaca agtttaatat gaaaaaaaaa aaaaaaaaa aa                            972
```

```
<210> SEQ ID NO 12
<211> LENGTH: 109
<212> TYPE: PRT
<213> ORGANISM: Rodent

<400> SEQUENCE: 12
```

```
Ser Lys Thr Gly Lys His Gly His Ala Lys Val His Leu Val Gly Ile
  1               5                  10                  15

Asp Ile Phe Thr Gly Lys Lys Tyr Glu Asp Ile Cys Pro Ser Thr His
             20                  25                  30

Asn Met Asp Val Pro Asn Ile Lys Arg Asn Asp Phe Gln Leu Ile Gly
         35                  40                  45

Ile Gln Asp Gly Tyr Leu Ser Leu Leu Gln Asp Ser Gly Glu Val Arg
 50                  55                  60

Glu Asp Leu Arg Leu Pro Glu Gly Asp Leu Gly Lys Glu Ile Glu Gln
65                  70                  75                  80

Lys Tyr Asp Cys Gly Glu Glu Ile Leu Ile Thr Val Leu Ser Ala Met
                 85                  90                  95

Thr Glu Glu Ala Ala Val Ala Ile Lys Ala Met Ala Lys
            100                 105
```

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
caggtctaga gttggaatcg aagc                                               24
```

```
<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
atatctcgag ccttgattgc aacagctgcc                                         30
```

```
<210> SEQ ID NO 15
<211> LENGTH: 489
<212> TYPE: DNA
<213> ORGANISM: Rodent
<220> FEATURE:
<221> NAME/KEY: CDS
<222> LOCATION: (33)...(485)

<400> SEQUENCE: 15
caggtctaga gttggaatcg aagcctctta aa atg gca gat gat ttg gac ttc          53
                                     Met Ala Asp Asp Leu Asp Phe
                                       1               5 gag aca gga gat gca ggg gcc tca gcc acc ttc cca atg cag tgc tca         101
Glu Thr Gly Asp Ala Gly Ala Ser Ala Thr Phe Pro Met Gln Cys Ser
```

```
                        10                  15                  20
gca  tta  cgt  aag  aat  ggt  ttt  gtg  gtg  ctc  aag  ggc  cgg  cca  tgt  aag        149
Ala  Leu  Arg  Lys  Asn  Gly  Phe  Val  Val  Leu  Lys  Gly  Arg  Pro  Cys  Lys
      25                  30                       35 atc  gtc  gag  atg  tct  act  tcg  aag  act  ggc  aag  cat  ggc  cat  gcc  aag        197
Ile  Val  Glu  Met  Ser  Thr  Ser  Lys  Thr  Gly  Lys  His  Gly  His  Ala  Lys
 40                       45                       50                       55 gtc  cat  ctg  gtt  ggt  att  gat  att  ttt  act  ggg  aag  aaa  tat  gaa  gat        245
Val  His  Leu  Val  Gly  Ile  Asp  Ile  Phe  Thr  Gly  Lys  Lys  Tyr  Glu  Asp
                60                       65                       70 atc  tgc  ccg  tcg  act  cat  aac  atg  gat  gtc  ccc  aac  atc  aaa  agg  aat        293
Ile  Cys  Pro  Ser  Thr  His  Asn  Met  Asp  Val  Pro  Asn  Ile  Lys  Arg  Asn
           75                       80                       85 gat  ttc  cag  ctg  att  ggc  atc  cag  gat  ggg  tac  cta  tcc  ctg  ctc  cag        341
Asp  Phe  Gln  Leu  Ile  Gly  Ile  Gln  Asp  Gly  Tyr  Leu  Ser  Leu  Leu  Gln
                90                       95                      100 gac  agt  ggg  gag  gta  cga  gag  gac  ctt  cgt  ctg  cct  gag  gga  gac  ctt        389
Asp  Ser  Gly  Glu  Val  Arg  Glu  Asp  Leu  Arg  Leu  Pro  Glu  Gly  Asp  Leu
          105                      110                      115 ggc  aag  gag  att  gag  cag  aag  tat  gac  tgt  gga  gaa  gag  atc  ctg  atc        437
Gly  Lys  Glu  Ile  Glu  Gln  Lys  Tyr  Asp  Cys  Gly  Glu  Glu  Ile  Leu  Ile
120                      125                      130                      135 aca  gtg  ctg  tcc  gcc  atg  aca  gag  gag  gca  gct  gtt  gca  atc  aag  gct        485
Thr  Val  Leu  Ser  Ala  Met  Thr  Glu  Glu  Ala  Ala  Val  Ala  Ile  Lys  Ala
               140                      145                      150 cgag                                                                                    489
```

<210> SEQ ID NO 16
<211> LENGTH: 151
<212> TYPE: PRT
<213> ORGANISM: Rodent

<400> SEQUENCE: 16

```
Met  Ala  Asp  Asp  Leu  Asp  Phe  Glu  Thr  Gly  Asp  Ala  Gly  Ala  Ser  Ala
 1                   5                   10                  15

Thr  Phe  Pro  Met  Gln  Cys  Ser  Ala  Leu  Arg  Lys  Asn  Gly  Phe  Val  Val
                20                  25                  30

Leu  Lys  Gly  Arg  Pro  Cys  Lys  Ile  Val  Glu  Met  Ser  Thr  Ser  Lys  Thr
            35                  40                  45

Gly  Lys  His  Gly  His  Ala  Lys  Val  His  Leu  Val  Gly  Ile  Asp  Ile  Phe
        50                  55                  60

Thr  Gly  Lys  Lys  Tyr  Glu  Asp  Ile  Cys  Pro  Ser  Thr  His  Asn  Met  Asp
65                  70                  75                  80

Val  Pro  Asn  Ile  Lys  Arg  Asn  Asp  Phe  Gln  Leu  Ile  Gly  Ile  Gln  Asp
                85                  90                  95

Gly  Tyr  Leu  Ser  Leu  Leu  Gln  Asp  Ser  Gly  Glu  Val  Arg  Glu  Asp  Leu
            100                 105                 110

Arg  Leu  Pro  Glu  Gly  Asp  Leu  Gly  Lys  Glu  Ile  Glu  Gln  Lys  Tyr  Asp
        115                 120                 125

Cys  Gly  Glu  Glu  Ile  Leu  Ile  Thr  Val  Leu  Ser  Ala  Met  Thr  Glu  Glu
130                 135                 140

Ala  Ala  Val  Ala  Ile  Lys  Ala
145                 150
```

<210> SEQ ID NO 17
<211> LENGTH: 20
<212> TYPE: DNA
<213> ORGANISM: Artificial Sequence -continued

```
<220> FEATURE:
<223> OTHER INFORMATION: Primer

<400> SEQUENCE: 17
gtctgtgtat tattgggccc                                                    20

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
gcgaagcttc catggctcga gtttttttttt tttttttttt tt                          42

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
ttgaaggggt gaggaaaa                                                      18

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ttgagtggga taaag                                                         15

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
aatcatctgc cattttaa                                                      18
```